US009175018B2

(12) United States Patent
Elliott et al.

(10) Patent No.: US 9,175,018 B2
(45) Date of Patent: Nov. 3, 2015

(54) BORONATE ESTER COMPOUNDS AND PHARMACEUTICAL COMPOSITIONS THEREOF

(71) Applicant: Millennium Pharmaceuticals, Inc., Cambridge, MA (US)

(72) Inventors: Eric L. Elliott, Brighton, MA (US); Abu J. Ferdous, Winchester, MA (US); Michael J. Kaufman, Lexington, MA (US); Sonja A. Komar, Belmont, MA (US); Debra L. Mazaik, Holliston, MA (US); Quentin J. Mccubbin, Belmont, MA (US); Phuong M. Nguyen, Cambridge, MA (US); Vaithianathan Palaniappan, Andover, MA (US); Raymond D. Skwierczynski, Andover, MA (US); Nobel T. Truong, Milford, MA (US); Csanad M. Varga, Newton, MA (US); Peter N. Zawaneh, Cambridge, MA (US)

( * ) Notice: Subject to any disclaimer, the term of this patent is extended or adjusted under 35 U.S.C. 154(b) by 0 days.

(21) Appl. No.: 14/449,328

(22) Filed: Aug. 1, 2014

(65) Prior Publication Data

US 2014/0343314 A1    Nov. 20, 2014

Related U.S. Application Data

(60) Division of application No. 13/667,164, filed on Nov. 2, 2012, now Pat. No. 8,859,504, which is a continuation of application No. 12/485,344, filed on Jun. 16, 2009, now abandoned.

(60) Provisional application No. 61/211,499, filed on Mar. 31, 2009, provisional application No. 61/132,244, filed on Jun. 17, 2008.

(51) Int. Cl.

| C07F 5/04 | (2006.01) |
|---|---|
| C07F 5/02 | (2006.01) |
| C07K 5/078 | (2006.01) |
| C07K 5/06 | (2006.01) |
| C07C 233/83 | (2006.01) |
| A61K 31/198 | (2006.01) |
| A61K 31/454 | (2006.01) |
| A61K 31/69 | (2006.01) |

(52) U.S. Cl.
CPC .............. *C07F 5/04* (2013.01); *A61K 31/198* (2013.01); *A61K 31/454* (2013.01); *A61K 31/69* (2013.01); *C07C 233/83* (2013.01); *C07F 5/025* (2013.01); *C07K 5/06139* (2013.01); *C07K 5/06191* (2013.01)

(58) Field of Classification Search
USPC ....................................................... 558/288
See application file for complete search history.

(56) References Cited

U.S. PATENT DOCUMENTS

| 4,499,082 | A | 2/1985 | Shenvi et al. |
|---|---|---|---|
| 5,106,948 | A | 4/1992 | Kinder et al. |
| 5,159,060 | A | 10/1992 | Kinder et al. |
| 5,169,841 | A | 12/1992 | Kleeman et al. |
| 5,187,157 | A | 2/1993 | Kettner et al. |
| 5,242,904 | A | 9/1993 | Kettner et al. |
| 5,250,720 | A | 10/1993 | Kettner et al. |
| 5,492,900 | A | 2/1996 | LaHann |
| 5,574,017 | A | 11/1996 | Gutheil |
| 5,580,486 | A | 12/1996 | Labeque et al. |
| 5,780,454 | A | 7/1998 | Adams et al. |
| 5,834,487 | A | 11/1998 | Lum et al. |
| 5,837,531 | A | 11/1998 | Dedieu et al. |
| 5,935,944 | A | 8/1999 | LaHann |
| 5,990,083 | A | 11/1999 | Iqbal et al. |
| 6,060,462 | A | 5/2000 | Galemmo, Jr. et al. |
| 6,066,730 | A | 5/2000 | Adams et al. |
| 6,083,903 | A | 7/2000 | Adams et al. |
| 6,169,076 | B1 | 1/2001 | Shull et al. |
| 6,297,217 | B1 | 10/2001 | Adams et al. |
| 6,699,835 | B2 | 3/2004 | Plamondon et al. |
| 6,713,446 | B2 | 3/2004 | Gupta |
| 6,781,000 | B1 | 8/2004 | Wang et al. |
| 6,846,806 | B2 | 1/2005 | Priestley |
| 6,958,319 | B2 | 10/2005 | Gupta |
| 7,109,323 | B2 | 9/2006 | Plamondon et al. |
| 7,223,745 | B2 | 5/2007 | Chatterjee et al. |
| 7,442,830 | B1 | 10/2008 | Olhava et al. |
| 7,687,662 | B2 | 3/2010 | Olhava et al. |
| 8,003,819 | B2 | 8/2011 | Olhava et al. |
| 8,859,504 | B2 * | 10/2014 | Elliott et al. ................ 514/19.3 |
| 2002/0188100 | A1 | 12/2002 | Plamondon et al. |

(Continued)

FOREIGN PATENT DOCUMENTS

| AU | 3951389 A | 3/1990 |
|---|---|---|
| EP | 0092999 B1 | 4/1992 |
| EP | 2 178 888 B1 | 4/2012 |
| JP | 2002145848 A | 5/2002 |
| WO | WO 96/13266 A1 | 5/1996 |
| WO | WO 96/14857 A1 | 5/1996 |
| WO | WO 98/35691 A1 | 8/1998 |
| WO | WO 99/15183 A1 | 4/1999 |
| WO | WO 99/30707 A1 | 6/1999 |
| WO | WO 00/57887 A1 | 10/2000 |

(Continued)

OTHER PUBLICATIONS

Berge. et al., J. Pharm. Sci., 1977, vol. 66, 1-19.

(Continued)

*Primary Examiner* — Rei-Tsang Shiao
(74) *Attorney, Agent, or Firm* — Honigman Miller Schwartz and Cohn LLP; Lucy X. Yang; Jonathan P. O'Brien

(57) ABSTRACT

The present invention provides novel compounds useful as proteasome inhibitors. The invention also provides pharmaceutical compositions comprising the compounds of the invention and methods of using the compositions in the treatment of various diseases.

40 Claims, 8 Drawing Sheets

(56) References Cited

U.S. PATENT DOCUMENTS

| | | |
|---|---|---|
| 2004/0171556 A1 | 9/2004 | Purandare et al. |
| 2005/0107307 A1 | 5/2005 | Bernadini et al. |
| 2005/0282742 A1 | 12/2005 | Plamondon et al. |
| 2006/0084592 A1 | 4/2006 | Boucher |
| 2006/0252740 A1 | 11/2006 | Johnson, Jr. et al. |
| 2010/0081633 A1 | 4/2010 | Fleming et al. |
| 2010/0204180 A1 | 8/2010 | Olhava et al. |
| 2011/0245203 A1 | 10/2011 | Fleming et al. |
| 2012/0041196 A1 | 2/2012 | Bernardini |

FOREIGN PATENT DOCUMENTS

| | | |
|---|---|---|
| WO | WO 01/02424 A2 | 1/2001 |
| WO | 0205923 | 1/2002 |
| WO | WO 02/059130 A1 | 8/2002 |
| WO | WO 02/059131 A1 | 8/2002 |
| WO | 03033507 | 4/2003 |
| WO | WO 03/059898 A2 | 7/2003 |
| WO | 2005016859 | 2/2005 |
| WO | WO 2005/021558 A2 | 3/2005 |
| WO | WO 2005/097809 A2 | 10/2005 |
| WO | 2005111008 | 11/2005 |
| WO | 2006052733 | 5/2006 |
| WO | WO 2007/005991 A1 | 1/2007 |
| WO | 2007089618 | 8/2007 |
| WO | 2009006473 | 1/2009 |
| WO | WO 2009/020448 A1 | 2/2009 |
| WO | WO 2010/036357 A1 | 4/2010 |
| WO | WO 2011/123502 A1 | 10/2011 |

OTHER PUBLICATIONS

Cancer (online), Retrieved on Jul. 6, 2007: MedlinePlus, a service of Medicine and the National Institutes of Health, Retrieved from the Internet, URL: http://www.nlm.nih.gov/medlineplus/cancer.html, 10 pages.

Capitulo 28: Iiotilizacion, Farmacotecnia: teoria y practicatomo 3. 1982. MX, pp. 1038-1041.

Dick. L.R., et al., "Building on bortezomib: second-generation proteasome inhibitors as anti-cancer therapy", Elsevier, Drug Discovery Today, vol. 15, No. 5. Mar. 6, 2010, pp. 243-249.

EP1880607 Opposition. Jan. 11, 2013, Proprietor's Submission, 10 pages.

EP2178888 Opposition. Oct. 17, 2011, Summons to Attend Oral Proceedings with Annex, 3 pages.

EP2178888 Opposition, Dec. 30, 2011, Annex to Proprietor's Letter dated Dec. 30, 2011, 3 pages.

EP2178888 Opposition. Dec. 30, 2011, Proprietor's Submission. 3 pages.

EP2178888 Opposition, Apr. 4, 2013, Opponent's Submission, 25 pages.

Golub, T.R., et al., "Molecular Classification of Cancer: Class Discovery and Class Prediction by Gene Expression Monitoring," Science, vol. 288, pp. 531-537 (Oct. 15, 1999).

http://goldbook.iupac.org/A00228.html. Retrieved from IUPAC, Compendium of Chemical Terminology, 2nd ed. (the "Gold Book"). Compiled by A. D. McNaught and A. Wilkinson, Blackwell Scientific Publications. Oxford (1997), XML on-line corrected version: http://goldbook.iupac.org (2006-) created by M. Nic, J. Jirat, B. Kosata; updates compiled by A. Jenkins. I SBN 0-9678550-9-8. doi:10.1351/goldbook, 1 page.

Lala, P.K. et al., "Role of Nitric Oxide in Tumor Progression: Lessons from Experimental Tumors," Cancer and Metastasis Reviews, vol. 17, pp. 91-106 (1998).

Lieberman, H., et al., "Tablet formulation and design." Pharmaceutical Dosage Forms: tablets vol. 1,1989, US, pp. 91-127.

Matteson, D.S., et al., "99% Chirally Selective Syntheses via Pinanediol Boronic Esters: Insect Pheromones, Diols, and an Amino Alcohol," Journal of American Chemical Society, vol. 108, No. 4, 1986, pp. 810-819.

Mullard, A., "Next-generation proteasome blockers promise safer cancer therapy", Nature Medicine, vol. 18 No. 1, Jan. 2012, p. 7.

Pachnis, V., et al., "The structure and expression of a novel gene activated in early mouse embryogenesis," The EMBO Journal, Mar. 1988, vol. 7, No. 3, pp. 673-681.

Ruggeri, B., "The Development and Pharmacology of Proteasome Inhibitors for the Management and Treatment of Cancer," Advances in Pharmacology, vol. 57, 2009, pp. 91-135.

Yoo-Warren, H. et al., "Two regulatory Domains Flank the Mouse H19 Gene", Molecular and Cellular Biology, vol. 8, No. 11, 1988, pp. 4707-4715.

Zhang, Y. et al., "Imprinting of human H19: allele-spedfic CpG methylation, loss of the active allele in Wilms tumor, and potential for somatic allele switching", Am. J. Hum. Genet., vol. 53, 1993, pp. 113-124.

Opponent's Notice of Opposition in EP1660507 Opposition (European Patent Office Date: May 4, 2010).

Proprietor's Response to the Notice of Opposition with Amended Claims in EP1660507 Opposition (European Patent Office Date: Jan. 17, 2011).

Summons to Attend Oral Proceedings with Annex in EP1680507 Opposition (European Patent Office Date: Apr. 1, 2011).

Proprietor's Submissions and Amendments in EP1660507 Opposition (European Patent Office Date: Sep. 7, 2011).

Opponent's Reply to Proprietor's Sep. 5, 2011 Submission in EP1660507 Opposition (European Patent Office Date: Sep. 19, 2011).

Proprietor's Letters Regarding Oral Proceedings in EP1680507 Opposition (European Patent Office Date: Sep. 21, 2011).

Oral Proceedings Minutes and Results in EP1660507 Opposition (European Patent Office Date: Nov. 2, 2011).

Opponent's Request for Correction of Minutes of Oral Proceedings in EP1660507 Opposition (European Patent Office Date: Nov. 10, 2011).

Proprietor's Request Regarding Minutes of Oral Proceedings in EP1660507 Opposition (European Patent Office Date: Nov. 29, 2011).

Correction of Minutes of Oral Proceedings in EP1660507 Opposition (European Patent Office Date: Dec. 5, 2011).

Opponent's Letter Further to Proprietor's Representative's Letter Dated Nov. 29, 2011 in EP1660507 Opposition (European Patent Office Date: Dec. 7, 2011).

Annex to Opposition Letter Dated Nov. 2, 2011 in EP1660507 Opposition (European Patent Office Date: Dec. 7, 2011).

Interlocutory Decision in Opposition Proceedings in EP1660507 Opposition (European Patent Office Date: Dec. 14, 2011).

Proprietor's Notice of Appeal Against Decision of the Opposition Division in EP1660507 Opposition (European Patent Office Date: Feb. 23, 2012).

Opponent's Notice of Appeal Against Decision of the Opposition Division in EP1660507 Opposition (European Patent Office Date: Feb. 23, 2012).

Opponent's Statement of Grounds of Appeal in EP1660507 Opposition (European Patent Office Date: Apr. 23, 2012).

Proprietor's Submissions and Amendments in EP1680507 Opposition (European Patent Office Date: Apr. 24, 2012).

Opponent's Reply to Proprietor's Grounds of Appeal of Apr. 24, 2012 in EP1660507 Opposition (European Patent Office Date: Sep. 12, 2012).

Proprietor's Response to Opponent's Grounds of Appeal in EP1660507 Opposition (European Patent Office Date: Sep. 12, 2012).

U.S. Office Action Mailed Mar. 7, 2012 in U.S. Appl. No. 13/249,738.

Response Filed Jul. 9, 2012 to Mar. 7, 2012 Office Action in U.S. Appl. No. 13/249,739.

U.S. Office Action (made final) Mailed Sep. 7, 2012 in U.S. Appl. No. 13/249,738.

International Search Report dated Jan. 19, 2010 in International Application No. PCT/US2009/005324 which corresponds with U.S. Appl. No. 12/586,650.

(56) References Cited

OTHER PUBLICATIONS

International Search Report dated Jun. 7, 2011 in International Application No. PCT/US2011/30455 which corresponds with U.S. Appl. No. 13/075,306.
Andersen, Marc W. et al., "*E-* and *Z-*Pentenyiboronates, Reagents for Simple Diasteroselection on Addition to Aldehydes," *Chemische Berichte*, vol. 122 (1989), pp. 1777-1782.
Armstrong, Terri et al., "Central Nervous System Toxicity from Cancer Treatment," *Current Oncology Reports*, vol. 5 (2004), pp. 11-19.
Groll, Michael et al., "Structure of 20S Proteasome from Yeast at 2.4A Resolution," *Nature*, vol. 386 (Apr. 3, 1997), pp. 463-471.
Gross, Erhard et al., "The Peptides: Analysis, Synthesis, Biology," *Protection of Functional Groups in Peptide Synthesis*, vol. 3, (Academic Press New York) (1981), pp. 3-88.
Harris, Jennifer L. et al., "Substrate Specificity of the Human Proteasome," *Chemistry and Biology*, vol. 8 (2001), pp. 1131-1141.
Hoffmann, Reinhard W. et al., "Towards an Understanding of Cram/*anti*-Cram Selectivity on Addition of Crotylboronates to α-Methylbutyraldehyde," *Chemische Berichte*, vol. 123 (1990), pp. 2387-2394.
Kettner, Charles A. et al., "Inhibition of the Serine Proteases Leukocyte Elastase, Pancreatic Elastase, Cathepsin G, and Chymotrypsin by Peptide Boronic Acids," *The Journal of Biological Chemistry*, vol. 259, No. 24 (Dec. 25, 1984), pp. 15106-15114.
King, Randall W. et el., "How Proteolysls Drives the Cell Cycle," *Science*, vol. 274 (Dec. 6, 1996), pp. 1652-1659.
Kupperman, Erik et al., "Evaluation of the Proteasome Inhibitor MLN9708 in Preclinical Models of Human Cancer," *Cancer Research*, vol. 70, No. 5 (Mar. 1, 2010), pp. 1970-1980.
Palombella, Vito J. et al., "The Ubiquitin-Proteasome Pathway Is Required for Processing the NF-κB1, Precursor Protein and the Activation of NF-κB," *Cell*, vol. 78, (Sep. 9. 1994), pp. 773-785.
Protective Groups in Organic Synthesis, $3^{rd}$ edition, edited by Theodora W. Greene and Peter G.M. Wuts, (A Wiley-Interscience Publication—John Wiley & Sons, Inc.) (1999), pp. 531-537.
Wallace, Richard H. et al., "Preparation and 1-Carbon Homologation of Boronic Ester Substituted $\Delta^2$-isoxazolines: The 1,3 Dipolar Cycloadditon of Nitrile Oxides to Vinyl Boronic Esters," *Tetrahedron Letters*, vol. 33, No. 46 (1992), pp. 6941-6944.
Zenk, Roland et al., "Organic Boronic Acids and Boronic Acid Esters in Industrial Synthesis," *Chimica Oggi (Chemistry Today)* (May 2003), pp. 70-73.
International Search Report and Written Opinion of the International Searching Authority dated Oct. 5, 2009 issued in International Application No. PCT/US09/003602, which corresponds to U.S. Appl. No. 12/485,344.
International Search Report and Written Opinion of the International Searching Authority dated Dec. 3, 2007 issued in International Application No. PCT/US07/017440, which corresponds to U.S. Appl. No. 11/890,412.
Ciechanover, Aaron, "The ubiquitin-proteasome proteolytic pathway," *Cell*, vol. 79 (Oct. 7, 1994) pp. 13-21.
Gardner, Robert C., et al., "Characterization of peptidyl boronic acid Inhibitors of mammalian 20 S and 26 S proteasomes and their Inhibition of proteasomes in cultured cells," *Biochemistry Journal*, vol. 346 (2000) pp. 447-454.
Gennaro, Algonso R. (editor), "Remington: The science and practice of pharmacy," $20^{th}$ Edition, Chapter 42, Lippincott Williams & Wilkins (publishers), Baltimore, MD (2000) pp. 802-803.
Kataoka, Kazunori, et al., "Totally synthetic polymer gels responding to external glucose concentration: their preparation and application to on-off regulation of insulin release," *Journal of the American Chemical Society*, vol. 120 (1998) pp. 12694-12695.
Kibbe, Arthur H. (editor), "Handbook of Pharmaceutical Excipients," $3^{rd}$ Edition, American Pharmaceutical Association (publishers), Washington, D.C. (2000) pp. 324-328.

Kinder, David H., et al., "Acylamino boronic acids and difuoroborane analogues of amino acids: potent inhibitors of chymotrypsin and elastase," *Journal of Medicinal Chemistry*, vol. 28, No. 12 (1985) pp. 1917-1925.
Kisselev, Alexei F., et al., "Proteasome inhibitors: from research tools to drug candidates," *Chemistry & Biology*, vol. 8, No. 8 (2001) pp. 739-758.
Korcek, S., et al., "Absolute rate constants for the autoxidation of organometallic compounds. Part II. Benzylboranes and 1-phenylethylboranes," *Journal of the Chemical Society, Perkin Transaction 2*, (1972) pp. 242-248.
Loidl, Gunther, et al., "Bifunctional inhibitors of the trypsin-like activity of eukaryotic proteasomes," *Chemistry & Biology*, vol. 6, No. 4 (1999) pp. 197-204.
Richardson, Paul G., et al., "A phase 2 study of bortezomib in relapsed, refractory myeloma," *The New England Journal of Medicine*, vol. 348, No. 26 (Jun. 28, 2003) pp. 2609-2617.
Snyder, H.R., et al., "Aryl botanic acids. II. Aryl boronic anhydrides and their amine complexes," *Journal of the American Chemical Society*, vol. 80 (Jul. 20, 1958) pp. 3611-3615.
Stella, V.J., et al., "Development of parenteral formulations of experimental cytotoxic agents. I. Rhizoxin (NSC-332598)," *International Journal of Pharmaceutics*, vol. 43 (1988) pp. 191-199.
Tran, Thuy, et al., "Synthesis and structure-activity relationship of N-acyl-Gly-, N-acyl-Sar- and N-blocked-boroPro Inhibitors of FAP, DPP4, and POP," *Bioorganic & Medicinal Chemistry Letters*, vol. 17 (2007) pp. 1438-1442.
Williams, N. Adeyinka, et al., "The effects of cooling rate on solid phase transitions and associated vial breakage occurring in frozen mannitol solutions," *Journal of Parenteral Science & Technology*, vol. 40, No. 4 (Jul.-Aug. 1986) pp. 135-141.
Williams, N. Adeyinka, et al., "Vial breakage by frozen mannitol solutions: correlation with thermal characteristics and effect of stereoisomerism, additives, and vial configuration," *Journal of Parenteral Science & Technology*, vol. 45, No. 2 (Mar.-Apr. 1991) pp. 94-100.
Houston, Todd A., et al., "Boric acid catalyzed chemoselective esterification of α-hydroxycarboxylic acids" *Organic Letters*, vol. 6, No. 5 (2004) pp. 679-681.
Meilend, Marcel, et al., "Seven-membered ring boronates at *trans*-diol moieties of carbohydrates," *Tetrahedron Letters*, vol. 50 (2009) pp. 469-472.
Lorand, John P., et al., "Polyol complexes and structure of the benzeneboronate ion," *Journal of Organic Chemistry*, vol. 24 (1958) pp. 769-774.
Scheibe, Edmund, "The borocitrates and their preparation," *The Pharmaceutical Journal and Transactions*, Third Series, No. 542 (Nov. 18, 1880) p. 389.
Prasad Sarju, et al., "Studies on the formation of some borocitrates" *Journal of the Indian Chemistry Society*, vol. 44, No. 3 (1967) pp. 219-220.
Bartusek, M., et al., "Boron chelates with citrate," *Scripta-Chemistry*, vol. 21 (1991) pp. 63-67.
Gray, Charles W., "Boronic acid receptors for α-hydroxycarboxylates: high affinity of Shinkai's glucose receptor for tartrate," *Journal of Organic Chemistry*, vol. 67, No. 15 (2002) pp. 5426-5428.
Van Duin, M., et al., "Studies on borate esters I," *Tetrahedron*, vol. 40, No. 15 (1984) pp. 2901-2911.
Van Duin, M., et al., "Studies on borate esters II," *Tetrahedron*, vol. 41, No. 16 (1986) pp. 3411-3421.
Communication pursuant to Article 94(3) EPC (Examination Report) dated Oct. 25, 2011 from corresponding European patent application 09 767 050.9-2117.

\* cited by examiner

BORONATE ESTER COMPOUNDS AND PHARMACEUTICAL COMPOSITIONS THEREOF

PRIORITY

This application is a divisional of U.S. Utility patent application Ser. No. 13/667,164, filed Nov. 2, 2012, which is a continuation of U.S. utility patent application Ser. No. 12/485,344, filed Jun. 16, 2009, which claims priority from U.S. Provisional Patent Application Ser. No. 61/132,244, filed Jun. 17, 2008, and U.S. Provisional Patent Application Ser. No. 61/211,499, filed Mar. 31, 2009; both which are hereby incorporated by reference in their entirety.

FIELD OF THE INVENTION

The present invention relates to boronate ester compounds useful as proteasome inhibitors. The invention also provides pharmaceutical compositions comprising the compounds of the invention, and methods of using the compositions in the treatment of various diseases.

BACKGROUND OF THE INVENTION

Boronic acid and boronate ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993), U.S. Pat. No. 5,242,904 (1993), and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain boronic acid compounds inhibit the growth of cancer cells. Magde et al., WO 04/022070 discloses peptide boronic acid compounds that inhibit thrombin. Boucher, U.S. Patent Application Pub. No. 20060084592 discloses various basic addition salts of peptide boronic acid compounds. Bachovchin et al., WO 07/005991, discloses peptide boronic acid compounds that inhibit fibroblast activating protein.

Boronic acid and ester compounds hold particular promise as inhibitors of the proteasome, a multicatalytic protease responsible for the majority of intracellular protein turnover. Adams et al., U.S. Pat. No. 5,780,454 (1998), describes peptide boronic ester and acid compounds useful as proteasome inhibitors. The reference also describes the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, and to inhibit NF-κB dependent cell adhesion. Furet et al., WO 02/096933, Chatterjee et al., WO 05/016859, and Bernadini et al, WO 05/021558 and WO 06/08660, disclose additional boronic ester and acid compounds that are reported to have proteasome inhibitory activity.

Ciechanover, Cell, 79:13-21 (1994), discloses that the proteasome is the proteolytic component of the ubiquitin-proteasome pathway, in which proteins are targeted for degradation by conjugation to multiple molecules of ubiquitin. Ciechanover also discloses that the ubiquitin-proteasome pathway plays a key role in a variety of important physiological processes. Rivett et al., Biochem. J. 291:1 (1993) discloses that the proteasome displays tryptic-, chymotryptic-, and peptidylglutamyl-peptidase activities. Constituting the catalytic core of the 26S proteasome is the 20S proteasome. McCormack et al., Biochemistry 37:7792 (1998), teaches that a variety of peptide substrates, including Suc-Leu-Leu-Val-Tyr-AMC, Z-Leu-Leu-Arg-AMC, and Z-Leu-Leu-Glu-2NA, wherein Suc is N-succinyl, AMC is 7-amino-4-methylcoumarin, and 2NA is 2-naphthylamine, are cleaved by the 20S proteasome.

Proteasome inhibition represents an important new strategy in cancer treatment. King et al., Science 274:1652-1659 (1996), describes an essential role for the ubiquitin-proteasome pathway in regulating cell cycle, neoplastic growth and metastasis. The authors teach that a number of key regulatory proteins, including, cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis.

Furthermore, the ubiquitin-proteasome pathway is required for transcriptional regulation. Palombella et al., Cell, 78:773 (1994), teaches that the activation of the transcription factor NF-κB is regulated by proteasome-mediated degradation of the inhibitor protein IκB. In turn, NF-κB plays a central role in the regulation of genes involved in the immune and inflammatory responses. Read et al., Immunity 2:493-506 (1995), teaches that the ubiquitin-proteasome pathway is required for expression of cell adhesion molecules, such as E-selectin, ICAM-1, and VCAM-1. Zetter, Seminars in Cancer Biology 4:219-229 (1993), teaches that cell adhesion molecules are involved in tumor metastasis and angiogenesis in vivo, by directing the adhesion and extravastation of tumor cells to and from the vasculature to distant tissue sites within the body. Moreover, Beg and Baltimore, Science 274:782 (1996), teaches that NF-κB is an anti-apoptotic controlling factor, and inhibition of NF-κB activation makes cells more sensitive to environmental stress and cytotoxic agents.

The proteasome inhibitor VELCADE® (bortezomib; N-2-pyrazinecarbonyl-L-phenylalanine-L-leucineboronic acid) is the first proteasome inhibitor to achieve regulatory approval. Mitsiades et al., Current Drug Targets, 7:1341 (2006), reviews the clinical studies leading to the approval of bortezomib for the treatment of multiple myeloma patients who have received at least one prior therapy. Fisher et al., J. Clin. Oncol., 30:4867 (2006), describes an international multi-center Phase II study confirming the activity of bortezomib in patients with relapsed or refractory mantle cell lymphoma. Ishii et al., Anti-Cancer Agents in Medicinal Chemistry, 7:359 (2007), and Roccaro et al., Curr. Pharm. Biotech., 7:1341 (2006), discuss a number of molecular mechanisms that may contribute to the antitumor activities of bortezomib.

Structural analysis reported by Voges et al., Annu. Rev. Biochem., 68:1015 (1999) reveals that the 20S proteasome comprises 28 subunits, with the catalytic subunits β1, β2, and β5 being responsible for peptidylglutamyl, tryptic, and chymotryptic peptidase activity, respectively. Rivett et al., Curr. Protein Pept. Sci., 5:153 (2004) discloses that when the proteasome is exposed to certain cytokines, including IFN-γ and TNF-α, the β1, β2, and β5 subunits are replaced with alternate catalytic subunits, β1i, β2i, and β5i, to form a variant form of the proteasome known as the immunoproteasome.

Orlowski, Hematology (Am. Soc. Hematol. Educ. Program) 220 (2005), discloses that the immunoproteasome also is expressed constitutively in some cells derived from hematopoietic precursors. The author suggests that inhibitors specific for the immunoproteasome may allow for targeted therapy against cancers arising from hematologic origins, thereby potentially sparing normal tissues, such as gastrointestinal and neurological tissues, from side effects.

Unfortunately, boronic acid compounds are relatively difficult to obtain in analytically pure form. For example, Snyder et al., *J. Am. Chem. Soc.* 80: 3611 (1958), teaches that arylboronic acid compounds readily form cyclic trimeric anhydrides under dehydrating conditions. Also, alkylboronic acids and their boroxines are often air-sensitive. Korcek et al., *J. Chem. Soc., Perkin Trans.* 2 242 (1972), teaches that butylboronic acid is readily oxidized by air to generate 1-butanol and boric acid. These difficulties limit the pharmaceutical utility of boronic acid compounds, complicating the characterization of pharmaceutical agents comprising boronic acid compounds and limiting their shelf-life.

Plamondon et al., WO 02/059131 discloses stable, pharmaceutically acceptable compositions prepared from boronic acid compounds and sugars. There remains a need for additional stable formulations of boronic acid compounds.

DESCRIPTION OF THE INVENTION

Figure 1:
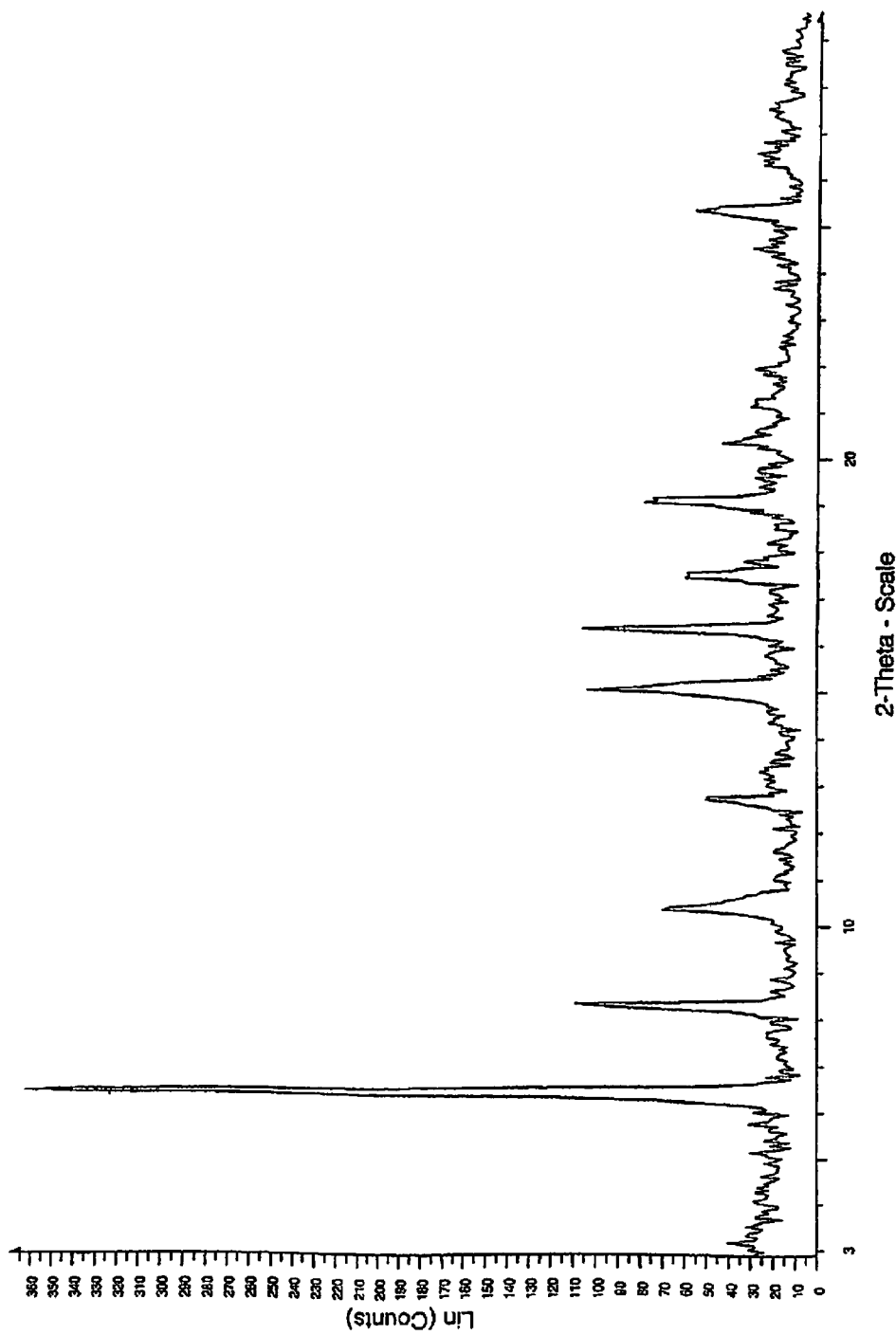
FIG. 1 is a powder X-ray diffractogram of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 1.

The present invention provides novel boronate ester compounds and stable pharmaceutically acceptable compositions comprising them. These compounds and compositions are useful for inhibiting proteasome activity in vitro and in vivo, and are especially useful for the treatment of various cell proliferative diseases.

In one aspect, the invention provides compounds of the general formula (I):

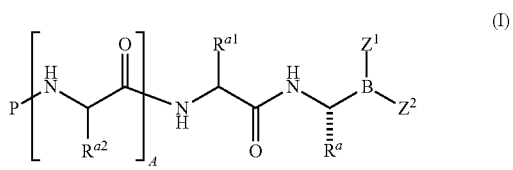

or a pharmaceutically acceptable salt or thereof, wherein:
A is 0, 1, or 2;
P is hydrogen or an amino-group-blocking moiety;
$R^a$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$;
$R^{a1}$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$;
each $R^{a2}$ independently is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$;
each $R^B$ independently is a substituted or unsubstituted mono- or bicyclic ring system;
each $R^4$ independently is hydrogen or a substituted or unsubstituted aliphatic, aryl, heteroaryl, or heterocyclyl group; or two $R^4$ on the same nitrogen atom, taken together with the nitrogen atom, form a substituted or unsubstituted 4- to 8-membered heterocyclyl ring having, in addition to the nitrogen atom, 0-2 ring heteroatoms independently selected from the group consisting of N, O, and S;
each $R^5$ independently is hydrogen or a substituted or unsubstituted aliphatic, aryl, heteroaryl, or heterocyclyl group;
each $R^{5a}$ independently is hydrogen or a substituted or unsubstituted aliphatic, aryl, heteroaryl, or heterocyclyl group;
each $R^{5b}$ independently is hydrogen or a substituted or unsubstituted aliphatic, aryl, heteroaryl, or heterocyclyl group;
each $R^6$ independently is a substituted or unsubstituted aliphatic, aryl, or heteroaryl group;
Y is hydrogen, —CN, or —NO$_2$;
m is 0, 1, or 2; and
$Z^1$ and $Z^2$ together form a moiety derived from an alpha-hydroxy carboxylic acid, wherein the atom attached to boron in each case is an oxygen atom; or $Z^1$ and $Z^2$ together form a moiety derived from a beta-hydroxy carboxylic acid, wherein the atom attached to boron in each case is an oxygen atom.

In another aspect, the present invention provides pharmaceutical compositions comprising the compound of formula (I), or a crystalline form thereof, and additional excipients described herein, suitable for the production of an oral pharmaceutical dosage form.

In another aspect, the invention provides a pharmaceutical composition comprising the compound of formula (I), or a crystalline form thereof, and additional excipients described herein, suitable for the production of a lyophilized powder pharmaceutical dosage form.

In another aspect, the invention provides a pharmaceutical composition comprising the compound of formula (I), or a crystalline form thereof, and additional excipients described herein, suitable for the production of a liquid pharmaceutical dosage form.

In another aspect, the invention provides a pharmaceutical composition, comprising the compound of formula (I), or a crystalline form thereof, a filler, and optionally a lubricant.

In another aspect, the invention provides a pharmaceutical composition, comprising the compound of formula (I), or a crystalline form thereof, a filler, optionally a lubricant, optionally a flow-aid, and optionally a buffer.

In another aspect, the invention provides a pharmaceutical composition, comprising the compound of formula (I), or a crystalline form thereof, a bulking agent, and a buffer.

In another aspect, the invention provides processes for the production of the pharmaceutical compositions of the invention.

In another aspect, the invention provides methods for the use of the pharmaceutical compositions of the invention, for treating a patient having, or at risk of developing or experiencing a recurrence of, a proteasome-mediated disorder.

In another aspect, the invention provides methods for the use of the pharmaceutical compositions of the invention for the treatment of cancer.

DEFINITIONS

Unless otherwise explicitly stated, the term "proteasome" is intended to refer to both constitutive proteasome and immunoproteasome.

The term "aliphatic" or "aliphatic group", as used herein, means a substituted or unsubstituted straight-chain, branched, or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight or branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aryl ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$ alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, radicals derived from thiophene, furan, pyrrole, imidazole, pyrazole, triazole, tetrazole, oxazole, isoxazole, oxadiazole, thiazole, isothiazole, thiadiazole, pyridine, pyridazine, pyrimidine, pyrazine, indolizine, naphthyridine, pteridine, pyrrolopyridine, imidazopyridine, oxazolopyridine, thiazolopyridine, triazolopyridine, pyrrolopyrimidine, purine, and triazolopyrimidine. As used herein, the phrase "radical derived from" means a monovalent radical produced by removal of a hydrogen radical from the parent heteroaromatic ring system. The radical (i.e., the point of attachment of the heteroaryl to the rest of the molecule) may be created at any substitutable position on any ring of the parent heteroaryl ring system.

In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from the group consisting of oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., —(CH$_2$)$_y$—, wherein y is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)C(=NR$^+$)—N(R$^+$)—, —N(R$^+$)—C(=NR$^+$)—, —N(R$^+$)CO$_2$—, —N(R$^+$)SO$_2$—, —N(R$^+$)SO$_2$N(R$^+$)—, —OC(O)—, —OC(O)O—, —OC(O)N(R$^+$)—, —C(O)—, —CO$_2$—, —C(O)N(R$^+$)—, —C(O)—C(O)—, —C(=NR$^+$)—N(R$^+$)—, —C(NR$^+$)=N—, —C(=NR$^+$)—O—, —C(OR*)=N—, —C(R°)=N—O—, or —N(R$^+$)—N(R$^+$)—. Each R$^+$ independently is hydrogen or an optionally substituted aliphatic, aryl, heteroaryl, or heterocyclyl group, or two R⁺ on the same nitrogen atom, taken together with the nitrogen atom, form a 5-8 membered aromatic or non-aromatic ring having, in addition to the nitrogen atom, 0-2 ring heteroatoms selected from the group consisting of N, O, and S. Each R* independently is hydrogen or an optionally substituted aliphatic, aryl, heteroaryl, or heterocyclyl group. Each R° independently is an optionally substituted aliphatic, aryl, or heteroaryl group.

Examples of $C_{3-6}$ alkylene chains that have been "interrupted" with —O— include —CH$_2$OCH$_2$—, —CH$_2$O(CH$_2$)$_2$—, —CH$_2$O(CH$_2$)$_3$—, —CH$_2$O(CH$_2$)$_4$—, —(CH$_2$)$_2$OCH$_2$—, —(CH$_2$)$_2$O(CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$Z*CH$_2$—, —CH$_2$Z*(CH$_2$)$_2$—, —CH$_2$Z*(CH$_2$)$_3$—, —CH$_2$Z*(CH$_2$)$_4$—, —(CH$_2$)$_2$Z*CH$_2$—, —(CH$_2$)$_2$Z*(CH$_2$)$_2$—, —(CH$_2$)$_2$Z*(CH$_2$)$_3$—, —(CH$_2$)$_3$Z*(CH$_2$)—, —(CH$_2$)$_3$Z*(CH$_2$)$_2$—, and —(CH$_2$)$_4$Z*(CH$_2$)—, wherein Z* is one of the "interrupting" functional groups listed above.

One of ordinary skill in the art will recognize that when an alkylene chain having an interruption is attached to a functional group, certain combinations would not be sufficiently stable for pharmaceutical use. Only stable or chemically feasible compounds are within the scope of the present invention. A stable or chemically feasible compound is one which maintains its integrity long enough to be useful for therapeutic or prophylactic administration to a patient. Preferably, the chemical structure is not substantially altered when kept at a temperature below −70° C., below −50° C., below −20° C., below 0° C., or below 20° C., in the absence of moisture or other chemically reactive conditions for at least a week.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the terms "independently" or "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —C≡C—R*, —OR*, —SR°, —S(O)R°, —SO$_2$R°, —SO$_3$R*, —SO$_2$N(R⁺)$_2$, —N(R⁺)$_2$, —NR⁺C(O)R*, —NR⁺C(O)N(R⁺)$_2$, —N(R⁺)—C(=NR⁺)—N(R⁺)$_2$, —N(R⁺)C(=NR⁺)—R°, —NR⁺CO$_2$R°, —NR⁺SO$_2$R°, —NR⁺SO$_2$N(R⁺)$_2$, —O—C(O)R*, —O—CO$_2$R*, —OC(O)N(R⁺)$_2$, —C(O)R*, —CO$_2$R*, —C(O)—C(O)R*, —C(O)N(R⁺)$_2$, —C(O)N(R⁺)—OR*, —C(O)N(R⁺)C(=NR⁺)—N(R⁺)$_2$, —N(R⁺)C(=NR⁺)—N(R⁺)—C(O)R*, —C(=NR⁴)—N(R⁺)$_2$, —C(=NR⁺)—OR*, —N(R⁺)—N(R⁺)$_2$, —C(=NR⁺)—N(R⁺)—OR*, —C(R°)=N—OR*, —P(O)(R*)$_2$, —P(O)(OR*)$_2$, —O—P(O)—OR*, and —P(O)(NR⁺)—N(R⁺)$_2$, wherein R°, R⁺, and R* are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, —N—NHC(O)R*, =N—NHCO$_2$R°, =N—NHSO$_2$R°, or =N—R*, where each R* and R° is as defined above.

Suitable substituents on a substitutable nitrogen atom of a heteroaryl or non-aromatic heterocyclic ring include —R*, —N(R*)$_2$, —C(O)R*, —CO$_2$R*, —C(O)—C(O)R* —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above. A ring nitrogen atom of a heteroaryl or non-aromatic heterocyclic ring also may be oxidized to form the corresponding N-hydroxy or N-oxide compound. A non-limiting example of such a heteroaryl having an oxidized ring nitrogen atom is N-oxidopyridyl.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all geometric (or conformational) isomers, i.e., (Z) and (E) double bond isomers and (Z) and (E) conformational isomers, as well as all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one stereoisomer relative to another stereoisomer, the mixture may contain, for example, an enantiomeric excess of at least 50%, 75%, 90%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used herein, the term "seeding" is used to refer to the addition of a crystalline material to initiate crystallization or recrystallization.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

As used herein, the term "solvate or solvated" means a physical association of a compound with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, hydrates, ethanolates, or methanolates. The physical properties of a solvate typically differ from other solvates, and from unsolvated forms of the compound. Because the chemical composition also differs between solvates these forms are referred to as "pseudo-polymorphs".

As used herein, the term "hydrate" is a solvate wherein the solvent molecule is $H_2O$ that is present in a defined stoichiometric amount, and may, for example, include hemihydrate, monohydrate, dihydrate, or trihydrate. As used herein, the term "anhydrate" is a compound of the invention that contains no $H_2O$ incorporated in its crystal lattice.

As used herein, "crystalline" refers to a solid having a highly regular chemical structure. In particular, a crystalline compound may be produced as one or more single crystalline forms of the compound. For the purposes of this application, the terms "single crystalline form" or "crystalline form" are used interchangeably and distinguish between crystals that have different properties (e.g., different XRPD patterns, different DSC scan results). Thus, each distinct polymorph and pseudopolymorph of a compound is considered to be a distinct single crystalline form herein.

"Substantially crystalline" refers to a compound that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to compounds that are at least 70% crystalline. In other embodiments, substantially crystalline refers to compounds that are at least 90% crystalline.

"Substantially pure" refers to a compound that may be at least a particular weight percent of the compound. Particular weight percentages are about 80%, about 85%, about 90%, about 91%, about 92%, about 93%, about 94%, about 95%, about 96%, about 97%, about 98%, about 99%, or about 99.5%.

Unless otherwise explicitly stated, structures depicted herein are meant to include all hydrates, anhydrates, solvates and polymorphs thereof.

As used herein, the terms "compound (I-1)" and "4-(R,S)-(carboxymethyl)-2-((R)-1-(2-(2,5-dichlorobenzamido)acetamido)-3-methylbutyl)-6-oxo-1,3,2-dioxaborinane-4-carboxylic acid" are used interchangeably, and include all crystalline forms. Both terms refer to the compounds produced in Example 1 and Example 1A in the Examples below including both Form 1 and Form 2.

As used herein, the terms "compound (I-1) Form 2" and "4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2" are used interchangeably. Both terms refer to the crystalline form 2 produced in Example 1 Form 2 and Example 1A Form 2 in the Examples below.

As used herein, the terms "compound of formula (VIII-1)", and "(R)-1-((2,5-dichlorobenzamido)acetamido)-3-methylbutylboronic acid" are used interchangeably. The compound of formula (VIII-1) is disclosed in U.S. Pat. No. 7,442,830 and WO 09/020448.

As used herein, the terms "compound of formula (I-15)", "compound (I-15)" and "(I-15)" are used interchangeably and are used to refer to the citrate ester of the compound (VIII-15), and the compound produced in Example 15 of the Examples below.

As used herein, the term "anhydride" used in reference to a boronic acid such as the compound of formula (VIII), refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of the invention are illustrated below:

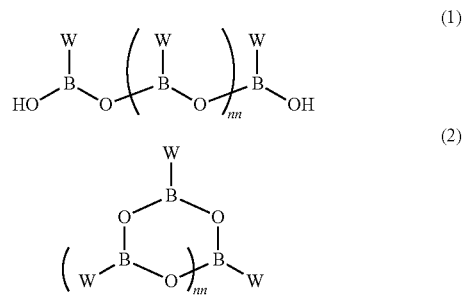

In formula (1) and (2), the variable nn is an integer from 0 to about 10, preferably 0, 1, 2, 3, or 4. In some embodiments, the boronic acid anhydride compound comprises a cyclic trimer ("boroxine") of formula (2), wherein nn is 1. The variable W has the formula (3):

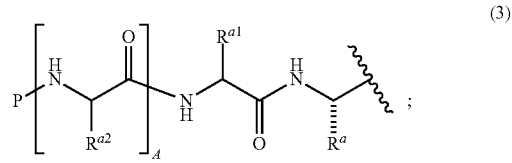

wherein P, $R^{a2}$, A, $R^{a1}$ and $R^{a}$ are as defined herein.

As used herein, the total weight of a single oral pharmaceutical dosage form is determined by adding all the weights of the components in the oral pharmaceutical dosage form, and does not include the weight of any coatings which may be optionally applied to the oral pharmaceutical dosage form after it is formed. The total weight of a single oral pharmaceutical dosage form is used as the basis for calculating the weight percentage of each of the components that comprise the oral pharmaceutical dosage form.

As used herein, "low-moisture" used in reference to an excipient such as a filler, refers to an excipient that has a water content of about 0.5% to about 4%. The term "low-moisture" may be used interchangeably with the term "low-water".

As used herein, the term "lyophilized powder", "cake", or "lyophilized cake" refers to any solid material obtained by lyophilization of an aqueous mixture.

As used herein, the term "tonicity modifier" refers to agents which contribute to the osmolality of a liquid or solution.

As used herein, the terms "boronate ester" and "boronic ester" are used interchangeably and refer to a chemical compound containing a —B($Z^1$)($Z^2$) moiety, wherein $Z^1$ and $Z^2$ together form a moiety where the atom attached to boron in each case is an oxygen atom.

In some embodiments, the boronate ester moiety is a 5-membered ring. In some other embodiments, the boronate ester moiety is a 6-membered ring. In some other embodiments, the boronate ester moiety is a mixture of a 5-membered ring and a 6-membered ring.

As used herein, the term "alpha-hydroxy carboxylic acid" refers to a compound that contains a hydroxyl group directly attached to a carbon atom in an alpha position relative to a carboxylic acid group. As used herein, the term "alpha-hydroxy carboxylic acid" is not intended to be limited to compounds having only one hydroxyl group and one carboxylic acid group.

As used herein, the term "beta-hydroxy carboxylic acid" refers to a compound that contains a hydroxyl group directly attached to a carbon atom in a beta position relative to a carboxylic acid group. As used herein, the term "beta-hydroxy carboxylic acid" is not intended to be limited to compounds having only one hydroxyl group and one carboxylic acid group.

As used herein, the term "moiety derived from an alpha-hydroxy carboxylic acid" refers to a moiety formed by removing a hydrogen atom from a carboxylic acid within an alpha-hydroxy carboxylic acid and by removing a hydrogen atom from a hydroxyl group directly attached to a carbon atom in an alpha position relative to the carboxylic acid group. As used herein, the term "moiety derived from a beta-hydroxy carboxylic acid" refers to a moiety formed by removing a hydrogen atom from a carboxylic acid within a beta-hydroxy carboxylic acid and by removing a hydrogen atom from a hydroxyl group directly attached to a carbon atom in a beta position relative to the carboxylic acid group.

DETAILED DESCRIPTION OF THE INVENTION

In some embodiments the alpha-hydroxy acid is characterized by formula (V):

(V)

wherein each of $R^{b3}$ and $R^{b4}$ independently is hydrogen, —$CO_2H$, or a substituted or unsubstituted aliphatic, aryl, heteroaryl or heterocyclyl group.

In some embodiments, each of $R^{b3}$ and $R^{b4}$ independently is hydrogen, $C_{1-6}$ aliphatic, or —$(CH_2)_p$—$CO_2H$, and p is 0, 1 or 2. In some embodiments, each of $R^{b3}$ and $R^{b4}$ independently is hydrogen or $C_{1-6}$ aliphatic. In certain such embodiments, each of $R^{b3}$ and $R^{b4}$ independently is selected from the group consisting of hydrogen, methyl, ethyl, isopropyl, isobutyl, tert-butyl, and cyclohexyl. In some other embodiments, each of $R^{b3}$ and $R^{b4}$ independently is hydrogen or —$(CH_2)_p$—$CO_2H$. In some such embodiments, p is 1. In certain other embodiments, each of $R^{b3}$ and $R^{b4}$ independently is —$(CH_2)_p$—$CO_2H$. In certain such embodiments, p is 1.

In some embodiments, the alpha-hydroxy carboxylic acid is selected from the group consisting of glycolic acid, malic acid, hexahydromandelic acid, citric acid, 2-hydroxyisobutyric acid, mandelic acid, lactic acid, 2-hydroxy-3,3-dimethylbutyric acid, 2-hydroxy-3-methylbutyric acid, 2-hydroxyisocaproic acid, and benzilic acid. In some other embodiments, the alpha-hydroxy carboxylic acid is selected from the group consisting of glycolic acid, malic acid, hexahydromandelic acid, citric acid, 2-hydroxyisobutyric acid, mandelic acid, lactic acid, 2-hydroxy-3,3-dimethylbutyric acid, 2-hydroxy-3-methylbutyric acid, 2-hydroxyisocaproic acid, tartaric acid, and benzilic acid. In certain embodiments, the alpha-hydroxy carboxylic acid is citric acid. Some other non-limiting examples of alpha-hydroxy carboxylic acids include glucoheptonic acid, maltonic acid, lactobionic acid, and galactaric acid.

In some embodiments the beta-hydroxy acid is characterized by formula (VI):

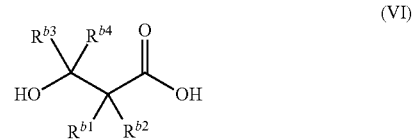

(VI)

wherein each of $R^{b1}$ and $R^{b2}$ independently is hydrogen, —$CO_2H$, —OH, or a substituted or unsubstituted aliphatic, aryl, heteroaryl or heterocyclyl group; each of $R^{b3}$ and e independently is hydrogen, —$CO_2H$, or a substituted or unsubstituted aliphatic, aryl, heteroaryl or heterocyclyl group;

or $R^{b2}$ and $R^{b4}$ are each independently hydrogen, and $R^{b1}$ and $R^{b3}$, taken together with the carbon atoms to which they are attached, form an unsubstituted or substituted 4- to 8-membered non-aromatic ring having 0-3 ring heteroatoms selected from the group consisting of O, N, and S, wherein said ring may optionally be fused to an unsubstituted or substituted 4- to 8-membered non-aromatic ring or 5- to 6-membered aromatic ring having 0-3 ring heteroatoms selected from the group consisting of O, N, and S;

or $R^{b2}$ and $R^{b4}$ are absent, and $R^{b1}$ and $R^{b3}$, taken together with the carbon atoms to which they are attached, form an unsubstituted or substituted 5- to 6-membered aromatic ring having 0-3 ring heteroatoms selected from the group consisting of O, N, and S, wherein said ring may optionally be fused to an unsubstituted or substituted 4- to 8-membered non-aromatic ring, or 5- to 6-membered aromatic ring having 0-3 ring heteroatoms selected from the group consisting of O, N, and S.

In some embodiments each of $R^{b1}$ and $R^{b2}$ independently is hydrogen, $C_{1-6}$ aliphatic, —$(CH_2)_p$—OH, or —$(CH_2)_p$—$CO_2H$, and p is 0, 1 or 2. In some such embodiments, each of $R^{b1}$ and $R^{b2}$ is hydrogen. In some other such embodiments, $R^{b1}$ is OH and $R^{b2}$ is hydrogen.

In some embodiments each of $R^{b3}$ and $R^{b4}$ independently is hydrogen, $C_{1-6}$ aliphatic, or —$(CH_2)_p$—$CO_2H$, and p is 0, 1 or 2. In some embodiments, each of $R^{b3}$ and $R^{b4}$ independently is hydrogen or $C_{1-6}$ aliphatic. In certain such embodiments, each of $R^{b3}$ and e independently is selected from the group consisting of hydrogen, methyl, ethyl, isopropyl, isobutyl, tert-butyl, and cyclohexyl. In certain other embodiments, each of $R^{b3}$ and $R^{b4}$ independently is —$(CH_2)_p$—$CO_2H$, and p is 0 or 1.

The variable p is 0, 1, or 2. In some embodiments, p is 0 or 1. In certain embodiments, p is 0. In other certain embodiments, p is 1.

In some embodiments, $R^{b2}$ and $R^{b4}$ are absent and $R^{b1}$ and $R^{b3}$ taken together with the carbon atoms to which they are attached, form a substituted or unsubstituted phenyl ring.

In some embodiments, the beta-hydroxy carboxylic acid is selected from the group consisting of malic acid, citric acid, 3-hydroxybutyric acid, beta-hydroxyisovaleric acid, and salicylic acid. In some other embodiments, the beta-hydroxy carboxylic acid is selected from the group consisting of malic acid, citric acid, 3-hydroxybutyric acid, beta-hydroxyisovaleric acid, tartaric acid, and salicylic acid. In certain embodiments, the beta-hydroxy carboxylic acid is citric acid. Some other non-limiting examples of beta-hydroxy carboxylic acids include glucoheptonic acid, maltonic acid, lactobionic acid, and galactaric acid. Some other non-limiting examples of beta-hydroxy carboxylic acids include embonic acid, 1-hydroxy-2-naphthoic acid and 3-hydroxy-2-naphthoic acid.

In some embodiments, the alpha-hydroxy acid or beta-hydroxy acid is selected from the group consisting of glycolic acid, malic acid, hexahydromandelic acid, 2-hydroxyisobutyric acid, citric acid, mandelic acid, lactic acid, 3-hydroxybutyric acid, beta-hydroxyisovaleric acid, 2-hydroxy-3,3-dimethylbutyric acid, 2-hydroxy-3-methylbutyric acid, 2-hydroxyisocaproic acid, tartaric acid, salicylic acid, and benzilic acid.

In some embodiments, compounds of general formula (I) are characterized by formula (II):

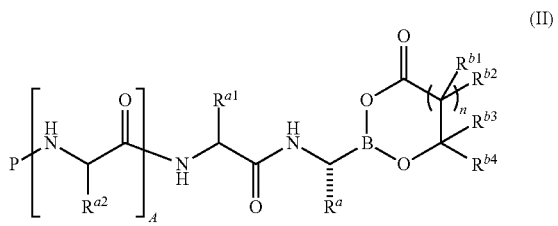

wherein:

the variables P, A, $R^a$, $R^{a1}$, $R^{a2}$, and n have the values described below and the variables $R^{b1}$, $R^{b2}$, $R^{b3}$ and $R^{b4}$ have the values described above.

In some embodiments, any one of $R^{b1}$, $R^{b2}$, $R^{b3}$ and $R^{b4}$ may contain a functional group that can form a further bond with the boron atom. In certain embodiments, the functional group is a carboxylic acid. In other certain embodiments, the functional group is a hydroxyl group.

In some embodiments, wherein the alpha-hydroxy carboxylic acid or beta-hydroxy carboxylic acid is citric acid, the compound of general formula (I) is characterized by formula (III) or (IV):

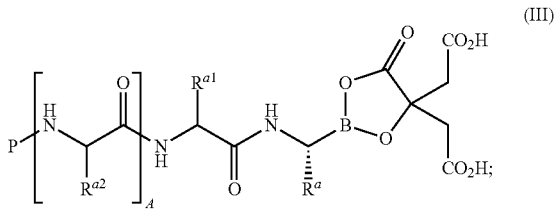

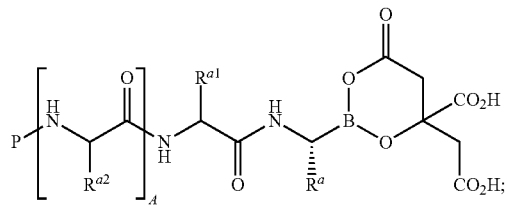

or a mixture thereof, wherein the variables P, A, $R^a$, $R^{a1}$, and $R^{a2}$ have the values described below.

In some other embodiments, wherein the alpha-hydroxy carboxylic acid or beta-hydroxy carboxylic acid is citric acid, a further bond can be formed between the carboxylic acid in formula (III) or (IV) and the boron atom. Without being limited by any chemical bonding theory, in such embodiments, the compound of general formula (I) may be represented by formula (IIIa) or (IVa):

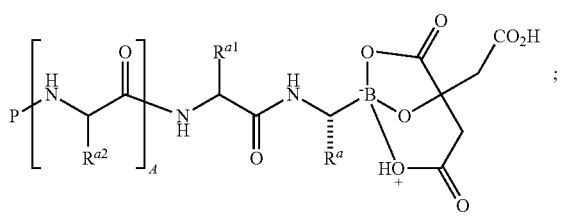

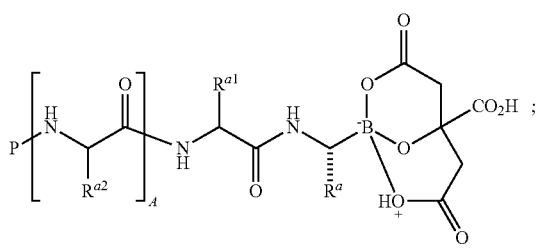

or a mixture thereof, wherein the variables P, A, $R^a$, $R^{a1}$, and $R^{a2}$ have the values described below.

It is recognized that, without being limited by any chemical bonding theory, there are other representations that could be used to depict this further bonding of the carboxylic acid with the boron atom in formulas (IIIa) and (IVa).

The following values are described for the variables in any of formulas (I), (II), (III), (IIIa), (IV), or (IVa).

The variable P is hydrogen or an amino-group-blocking moiety. Non-limiting examples of amino-group-blocking moieties can be found in P. G. M. Wuts and T. W. Greene, *Greene's Protective Groups in Organic Synthesis* (4$^{th}$ ed.), John Wiley & Sons, NJ (2007), and include, e.g., acyl, sulfonyl, oxyacyl, and aminoacyl groups.

In some embodiments, P is $R^c$—C(O)—, $R^c$—O—C(O)—, $R^c$—N($R^{4c}$)—C(O)—, $R^c$—S(O)$_2$—, or $R^c$—N($R^{4c}$)—S(O)$_2$—, where $R^c$ is selected from the group consisting of $C_{1-6}$ aliphatic, $C_{1-6}$ fluoroaliphatic, —$R^D$, -$T^1$-$R^D$, and -$T^1$-$R^{2c}$, and the variables $T^1$, $R^D$, $R^{2c}$, and $R^{4c}$ have the values described below.

The variable $R^{4c}$ is hydrogen, $C_{1-4}$ alkyl, $C_{1-4}$ fluoroalkyl, or $C_{6-10}$ ar($C_{1-4}$ alkyl), the aryl portion of which is substituted or unsubstituted. In some embodiments, $R^{4c}$ is hydrogen or $C_{1-4}$ alkyl. In certain embodiments, $R^{4c}$ is hydrogen.

The variable $T^1$ is a $C_{1-6}$ alkylene chain substituted with 0-2 independently selected $R^{3a}$ or $R^{3b}$, wherein the alkylene chain optionally is interrupted by —C($R^5$)=C($R^5$)—, —C≡C—, or —O—. Each $R^{3a}$ independently is selected from the group consisting of —F, —OH, —O($C_{1-4}$ alkyl), —CN, —N($R^4$)$_2$, —C(O)—($C_{1-4}$ alkyl), —CO$_2$H, —CO$_2$ ($C_{1-4}$ alkyl), —C(O)NH$_2$, and —C(O)—NH($C_{1-4}$ alkyl). Each $R^{3b}$ independently is a $C_{1-3}$ aliphatic optionally substituted with $R^{3a}$ or $R^7$; or two substituents $R^{3b}$ on the same carbon atom, taken together with the carbon atom to which they are attached, form a 3- to 6-membered cycloaliphatic ring. Each $R^7$ is a substituted or unsubstituted aromatic group. In some embodiments, $T^1$ is a $C_{1-4}$ alkylene chain.

The variable $R^{2c}$ is halo, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, or —C(O)N(R$^4$)$_2$, where:

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from the group consisting of N, O, and S;

each $R^5$ independently is hydrogen or an optionally substituted aliphatic, aryl, heteroaryl, or heterocyclyl group; and each $R^6$ independently is an optionally substituted aliphatic, aryl, or heteroaryl group.

The variable $R^D$ is a substituted or unsubstituted aromatic, heterocyclyl, or cycloaliphatic ring, any of which is optionally fused to a substituted or unsubstituted aromatic, heterocyclyl or cycloaliphatic ring. In some embodiments, $R^D$ is substituted on substitutable ring carbon atoms with 0-2 $R^d$ and 0-2 $R^{8d}$, and each substitutable ring nitrogen atom in $R^D$ is unsubstituted or is substituted with —C(O)R$^5$, —C(O)N(R$^4$)$_2$, —CO$_2$R$^6$, —SO$_2$R$^6$, —SO$_2$N(R$^4$)$_2$, $C_{1-4}$ aliphatic, a substituted or unsubstituted $C_{6-10}$ aryl, or a $C_{6-10}$ ar($C_{1-4}$) alkyl, the aryl portion of which is substituted or unsubstituted. The variables $R^4$, $R^5$, and $R^6$ have the values described above. Each $R^d$ independently is selected from the group consisting of $C_{1-6}$ aliphatic, $C_{1-6}$ fluoroaliphatic, halo, —R$^{1d}$, —R$^{2d}$, -T$^2$-R$^{1d}$, and -T$^2$-R$^{2d}$, where the variables $T^2$, $R^{1d}$, $R^{2d}$, and $R^{8d}$ have the values described below. In some embodiments, each $R^d$ independently is selected from the group consisting of $C_{1-6}$ aliphatic, $C_{1-6}$ fluoroaliphatic and halo.

$T^2$ is a $C_{1-6}$ alkylene chain substituted with 0-2 independently selected $R^{3a}$ or $R^{3b}$, wherein the alkylene chain optionally is interrupted by C($R^5$)=C($R^5$)—, —C≡C—, or —O—. The variables $R^{3a}$, $R^{3b}$, and $R^5$ have the values described above.

Each $R^{1d}$ independently is a substituted or unsubstituted aryl, heteroaryl, heterocyclyl, or cycloaliphatic ring.

Each $R^{2d}$ independently is —NO$_2$, —CN, C($R^5$)=C($R^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, or —C(=NR$^4$)—N(R$^4$)$_2$. The variables $R^4$, $R^5$, and $R^6$ have the values described above.

Each $R^{8d}$ independently is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$. In some embodiments, each $R^{8d}$ independently is $C_{1-4}$ aliphatic, $C_{1-4}$ fluoroaliphatic or halo.

In some embodiments, $R^D$ is a substituted or unsubstituted mono- or bicyclic ring system. In some embodiments $R^D$ is a substituted or unsubstituted mono- or bicyclic ring system selected from the group consisting of furanyl, thienyl, pyrrolyl, isoxazolyl, oxazolyl, thiazolyl, isothiazolyl, imidazolyl, pyrazolyl, oxadiazolyl, thiadiazolyl, phenyl, pyridinyl, pyridazinyl, pyrimidinyl, pyrazinyl, benzofuranyl, benzothiophenyl, indolyl, benzoxazolyl, benzisoxazolyl, benzimidazolyl, indazolyl, purinyl, naphthyl, quinolinyl, isoquinolinyl, cinnolinyl, quinazolinyl, quinoxalinyl, phthalazinyl, naphthyridinyl, tetrahydroquinolinyl, tetrahydroisoquinolinyl, tetrahydroquinoxalinyl, and dihydrobenzoxazinyl. In some embodiments, $R^D$ is a substituted or unsubstituted mono- or bicyclic ring system selected from the group consisting of phenyl, pyridinyl, pyrimidinyl, pyrazinyl, naphthyl, benzimidazolyl, quinolinyl, isoquinolinyl, quinoxalinyl, tetrahydroquinolinyl, tetrahydroisoquinolinyl, tetrahydroquinoxalinyl, and dihydrobenzoxazinyl.

In some embodiments, the substitutable ring carbon atoms in $R^D$ are substituted on substitutable carbon atoms with 0-1 $R^d$ and 0-2 $R^{8d}$; wherein:

each $R^d$ independently is $C_{1-6}$ aliphatic, $C_{1-6}$ fluoroaliphatic or halo; and each $R^{8d}$ independently is $C_{1-4}$ aliphatic, $C_{1-4}$ fluoroaliphatic or halo.

In some embodiments, the substitutable ring carbon atoms in $R^D$ are substituted with 0-1 $R^d$ and 0-2 $R^{8d}$, wherein:

$T^1$ is a $C_{1-3}$ alkylene chain that is unsubstituted or is substituted with $R^{3a}$ or $R^{3b}$;

each $R^{1d}$ independently is a substituted or unsubstituted aryl, heteroaryl, heterocyclyl, or cycloaliphatic ring; and each $R^{2d}$ independently is —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —O—C(O)R$^5$, —OC(O)N(R$^4$)$_2$, —C(O)R$^5$, —CO$_2$R$^5$, or —C(O)N(R$^4$)$_2$. The variables $R^4$, $R^5$, and $R^6$ have the values described above.

In some embodiments, the variable $R^d$ has the formula -Q-R$^E$, where Q is —O—, —NH—, or —CH$_2$—, and $R^E$ is a substituted or unsubstituted aryl, heteroaryl, heterocyclyl, or cycloaliphatic ring. In some embodiments, $R^E$ is a substituted or unsubstituted phenyl, pyridinyl, pyrimidinyl, pyrazinyl, piperidinyl, piperazinyl, or morpholinyl ring.

In some embodiments, P has the formula R$^c$—C(O)—, where is $C_{1-4}$ alkyl, $C_{1-4}$ fluoroalkyl, or $C_{6-10}$ ar($C_{1-4}$) alkyl, the aryl portion of which is substituted or unsubstituted. In certain such embodiments, P is selected from the group consisting of acetyl, trifluoroacetyl, and phenylacetyl.

In some other embodiments, P has the formula $R^D$—C(O)—, where $R^D$ is a substituted or unsubstituted phenyl, pyridinyl, pyrazinyl, pyrimidinyl, quinolinyl, or quinoxalinyl. In yet some other embodiments, P has the formula $R^D$—C(O), where $R^D$ is a phenyl, pyridinyl, pyrazinyl, pyrimidinyl, naphthyl, quinolinyl, quinoxalinyl, benzimidazolyl, or dihydrobenzoxazinyl substituted with 0-1 $R^d$ and 0-2 $R^{8d}$.

In certain embodiments, P has the formula $R^D$—C(O)—, where $R^D$ is 2-pyrazinyl. In other certain embodiments, P has the formula $R^D$—C(O)—, where $R^D$ is 2,5-dichlorophenyl. In yet other certain embodiments, P has the formula $R^D$—C(O)—, where $R^D$ is 6-phenyl-2-pyridinyl.

In some other embodiments, P has the formula $R^c$—SO$_2$—, where $R^c$ is —R$^D$ or -T$^1$-R$^D$, where $T^1$ is $C_{1-4}$ alkylene and $R^D$ is a phenyl, pyridinyl, pyrazinyl, pyrimidinyl, naphthyl, quinolinyl, quinoxalinyl, benzimidazolyl, or dihydrobenzoxazinyl substituted with 0-1 $R^d$ and 0-2 $R^{8d}$.

The variable $R^a$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$, where the variables $R^4$, $R^5$, and $R^6$ have the values described above, and the variables $R^{5a}$, $R^{5b}$, $R^B$, Y, and m have the values described below.

In some embodiments, $R^a$ is hydrogen, $C_{1-6}$ aliphatic, $C_{1-6}$ fluoroaliphatic, or —$(CH_2)_m$—$CH_2$—$R^B$. In some other embodiments, $R^a$ is $C_{1-6}$ aliphatic, or —$(CH_2)_m$—$CH_2$—$R^B$. In some further embodiments, $R^a$ is $C_{1-6}$ aliphatic. In yet other further embodiments, $R^a$ is isobutyl, 1-naphthylmethyl, 2-naphthylmethyl, benzyl, 4-fluorobenzyl, 4-hydroxybenzyl, 4-(benzyloxy)benzyl, benzylnapththylmethyl or phenethyl. In certain embodiments, $R^a$ is isobutyl.

The variable $R^{a1}$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$, where the variables $R^4$, $R^5$, and $R^6$ have the values described above, and the variables $R^{5a}$, $R^{5b}$, $R^B$, Y, and m have the values described below.

In some embodiments, $R^{a1}$ is hydrogen, $C_{1-6}$ aliphatic, $C_{1-6}$ fluoroaliphatic, —$(CH_2)_m$—$CH_2$—$R^B$, or —$(CH_2)_m$—CH(R$^{5a}$)—OR$^{5b}$. In some other embodiments, $R^{a1}$ is hydrogen, —$(CH_2)_m$—$CH_2$—$R^B$, or —$(CH_2)_m$—CH(R$^{5a}$)—OR$^{5b}$. In yet some other embodiments, $R^{a1}$ is isobutyl, 1-naphthylmethyl, 2-naphthylmethyl, benzyl, 4-fluorobenzyl, 4-hydroxybenzyl, 4-(benzyloxy)benzyl, benzylnaphthylmethyl or phenethyl.

In certain embodiments, $R^{a1}$ is —$CH_2$—$R^B$. In other certain embodiments, $R^{a1}$ is —CH(R$^{5a}$)—OR$^{5b}$. In yet other certain embodiments, $R^{a1}$ is hydrogen.

The variable $R^{a2}$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=NR$^4$)NH—Y, —$(CH_2)_m$—$CH_2$—CON(R$^4$)$_2$, —$(CH_2)_m$—$CH_2$—N(R$^4$)CON(R$^4$)$_2$, —$(CH_2)_m$—CH(R$^6$)N(R$^4$)$_2$, —$(CH_2)_m$—CH(R$^{5a}$)—OR$^{5b}$, or —$(CH_2)_m$—CH(R$^5$)—SR$^5$, where the variables $R^4$, $R^5$, and $R^6$ have the values described above, and the variables $R^B$, $R^{5a}$, $R^{5b}$, Y, and m have the values described below.

In some embodiments, $R^{a2}$ is hydrogen, $C_{1-6}$ aliphatic, $C_{1-6}$ fluoroaliphatic, —$(CH_2)_m$—$CH_2$—$R^B$, or —$(CH_2)_m$—CH(R$^{5a}$)—OR$^{5b}$. In some other embodiments, $R^{a2}$ is isobutyl, 1-naphthylmethyl, 2-naphthylmethyl, benzyl, 4-fluorobenzyl, 4-hydroxybenzyl, 4-(benzyloxy)benzyl, benzylnaphthylmethyl or phenethyl.

Each $R^B$, independently, is a substituted or unsubstituted mono- or bicyclic ring system. In some embodiments, each $R^B$ independently is a substituted or unsubstituted phenyl, pyridyl, indolyl, benzimidazolyl, naphthyl, quinolinyl, quinoxalinyl, or isoquinolinyl ring. In certain embodiments, $R^B$ is a substituted or unsubstituted phenyl ring.

The variable Y is hydrogen, —CN, or —NO$_2$. In some embodiments, Y is —NO$_2$.

The variable $R^{5a}$ is hydrogen or a substituted or unsubstituted aliphatic, aryl, heteroaryl, or heterocyclyl group. In some embodiments, $R^{5a}$ is hydrogen or a substituted or unsubstituted aliphatic group. In some other embodiments, $R^{5a}$ is hydrogen or $C_{1-6}$ aliphatic. In such embodiments, $R^{5a}$ is selected from the group consisting of hydrogen, methyl, ethyl, isopropyl and isobutyl. In certain such embodiments, $R^{5a}$ is methyl.

The variable $R^{5b}$ is hydrogen or a substituted or unsubstituted aliphatic, aryl, heteroaryl, or heterocyclyl group. In some embodiments, $R^{5b}$ is hydrogen or a substituted or unsubstituted aliphatic group. In some other embodiments, $R^{5b}$ is hydrogen or $C_{1-6}$ aliphatic. In such embodiments, $R^{5b}$ is selected from the group consisting of hydrogen, methyl, ethyl, isopropyl and isobutyl. In certain such embodiments, $R^{5b}$ is hydrogen.

The variable m is 0, 1, or 2. In some embodiments, m is 0 or 1. In certain embodiments, m is 0. In other certain embodiments, m is 1.

The variable A is 0, 1, or 2. In some embodiments, A is 0 or 1. In certain embodiments, A is 0.

The variable n is 0, or 1. In certain embodiments, n is 0. In other certain embodiments, n is 1.

In some embodiments, A is 0; $R^a$ is hydrogen, $C_{1-6}$ aliphatic, $C_{1-6}$ fluoroaliphatic, or —$(CH_2)_m$—$CH_2$—$R^B$; $R^{a1}$ is hydrogen, $C_{1-6}$ aliphatic, $C_{1-6}$ fluoroaliphatic, —$(CH_2)_m$—$CH_2$—$R^B$, or —$(CH_2)_m$—CH(R$^{5a}$)—OR$^{5b}$; P is $R^c$—C(O)— or $R^c$—S(O)$_2$—; $R^c$ is —$R^D$; and m is 0 or 1.

In some other embodiments, A is 0; $R^a$ is $C_{1-6}$ aliphatic or —$(CH_2)_m$—$CH_2$—$R^B$; $R^{a1}$ is hydrogen, —$(CH_2)_m$—$CH_2$—$R^B$, or —$(CH_2)_m$—CH(R$^{5a}$)—OR$^{5b}$; P is $R^c$—C(O)— or $R^c$—S(O)$_2$—; $R^c$ is —$R^D$; and m is 0 or 1.

In some other embodiments, A is 0; $R^a$ is $C_{1-6}$ aliphatic; $R^{a1}$ is hydrogen, —$(CH_2)_m$—$CH_2$—$R^B$, or —$(CH_2)_m$—CH(R$^{5a}$)—OR$^{5b}$; P is $R^c$—C(O); $R^c$ is —$R^D$; and m is 0 or 1.

In some other embodiments, A is 0; $R^a$ is isobutyl; $R^{a1}$ is hydrogen, $C_{1-6}$ aliphatic, $C_{1-6}$ fluoroaliphatic, —$(CH_2)_m$—$CH_2$—$R^B$, or —$(CH_2)_m$—CH(R$^{5a}$)—OR$^{5b}$; P is $R^c$—C(O)—; $R^c$ is —$R^D$; and m is 0 or 1.

In yet some other embodiments, A is 0; $R^a$ is isobutyl; $R^{a1}$ is hydrogen, $C_{1-6}$ aliphatic, —$(CH_2)_m$—$CH_2$—$R^B$, or —$(CH_2)_m$—CH(R$^{5a}$)—OR$^{5b}$; P is $R^c$—C(O)—; $R^c$ is —$R^D$; and m is 0 or 1.

In still yet some other embodiments, A is 0; $R^a$ is isobutyl; $R^{a1}$ is hydrogen, —$(CH_2)_m$—$CH_2$—$R^B$, or —$(CH_2)_m$—CH(R$^{5a}$)—OR$^{5b}$; P is $R^c$—C(O)—; $R^c$ is —$R^D$; and m is 0 or 1.

In certain embodiments, A is 0; $R^a$ is isobutyl; $R^{a1}$ is CH$_2$—$R^B$, and $R^B$ is phenyl; P is $R^c$—C(O)—; Re is —$R^D$; and $R^D$ is 2-pyrazinyl.

In other certain embodiments, A is 0; $R^a$ is isobutyl; $R^{a1}$ is hydrogen; P is $R^c$—C(O)—; $R^c$ is —$R^D$; and $R^D$ is 2,5-dichlorophenyl.

In yet other certain embodiments, A is 0; $R^a$ is isobutyl; $R^{a1}$ is —CH(R$^{5a}$)—OR$^{5b}$; $R^{5a}$ is $C_{1-6}$ aliphatic; $R^{5b}$ is hydrogen; P is $R^c$—C(O)—; Re is —$R^D$; and $R^D$ is 6-phenyl-2-pyridinyl-.

In some embodiments, the compound of formula (I) is characterized by formula (I-1):

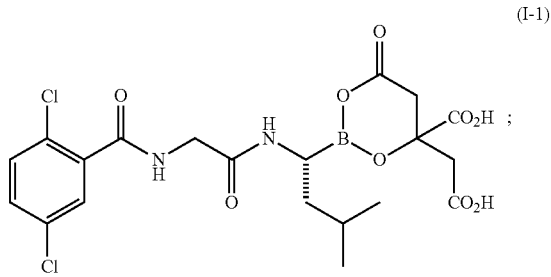 [SMILES: CC(C)C[C@H](NC(=O)CNC(=O)c1cc(Cl)ccc1Cl)B1OC(=O)CC(CC(=O)O)(C(=O)O)O1]

(I-1)

or a crystalline form thereof.

In some other embodiments, the compound of formula (I) is characterized by formula (I-15):

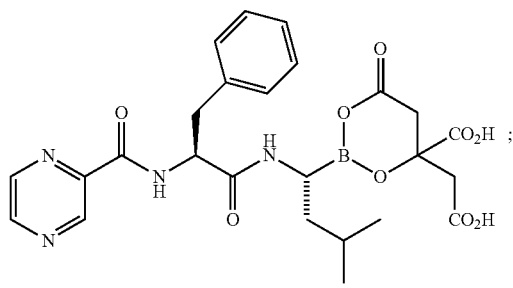

(I-15)

or a crystalline form thereof.

In yet some other embodiments, the compound of formula (I) is characterized by formula (I-18):

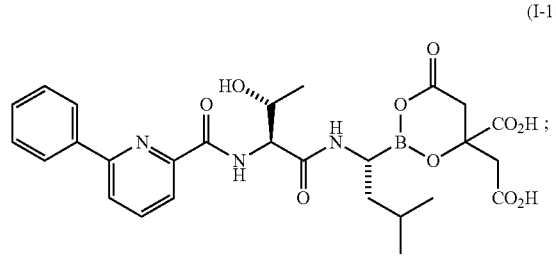

(I-18)

or a crystalline form thereof.

General Synthetic Methodology

The compounds of formula (I) can be prepared by esterification of corresponding boronic acids. Such boronic acid compounds can be prepared from methods known to one of ordinary skill in the art. See, e.g., Adams et. al., U.S. Pat. No. 5,780,454; Pickersgill et al., International Patent Publication WO 2005/097809. An exemplary synthetic route is set forth in Scheme 1 below.

Coupling of compound i with an N-protected amino acid ii, followed by N-terminal deprotection, provides compound iii or a salt thereof. Examples of suitable protecting groups (PG) include, without limitation, acyl protecting groups, e.g., formyl, acetyl (Ac), succinyl (Suc), and methoxysuccinyl; and urethane protecting groups, e.g., tert-butoxycarbonyl (Boc), benzyloxycarbonyl (Cbz), and fluorenylmethoxycarbonyl (Fmoc). Optionally, PG is hydrogen and deprotection is not necessary. The peptide coupling reaction can be conducted by prior conversion of the carboxylic acid moiety of compound ii to an activated ester or acid halide, e.g., an O—(N-hydroxysuccinnimide) ester, followed by treatment with compound i. Alternatively, the activated ester can be generated in situ by contacting the carboxylic acid with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., (benzotriazol-1-yloxy)tris(dimethylamino)phosphonium hexafluorophosphate (BOP); and uronium reagents, e.g., O-(1H-benzotriazol-1-yl)-N,N,N',N'-tetramethyluronium tetrafluoroborate (TBTU).

Compound iii is then coupled with an amino-group blocking moiety, to afford compound iv. The peptide coupling conditions described above for the coupling of compounds i and ii are also suitable for coupling compound iii with the amino-group blocking moiety. Deprotection of the boronic acid moiety then affords compound v. The deprotection step preferably is accomplished by transesterification in a biphasic mixture comprising the boronic ester compound iv, an organic boronic acid acceptor, a lower alkanol, a $C_{5-8}$ hydrocarbon solvent, and aqueous mineral acid. Other reagents that can be used for deprotection of the boronic acid moiety include, without limitation, $BCl_3$, lithium aluminium hydride and $NaIO_4$.

Scheme 1:

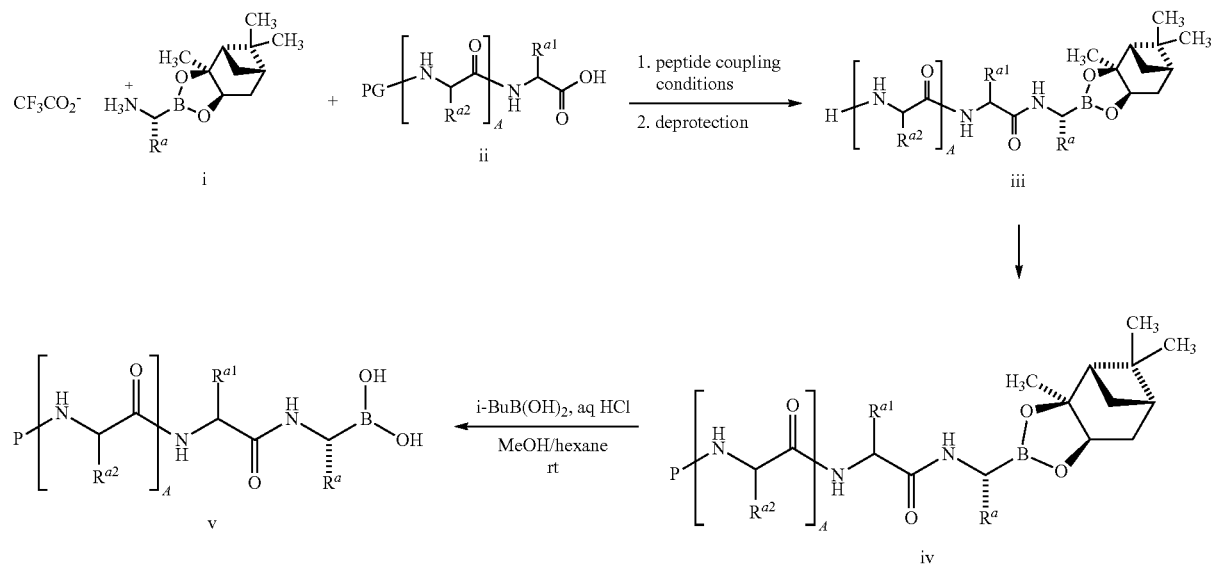

Scheme 2:

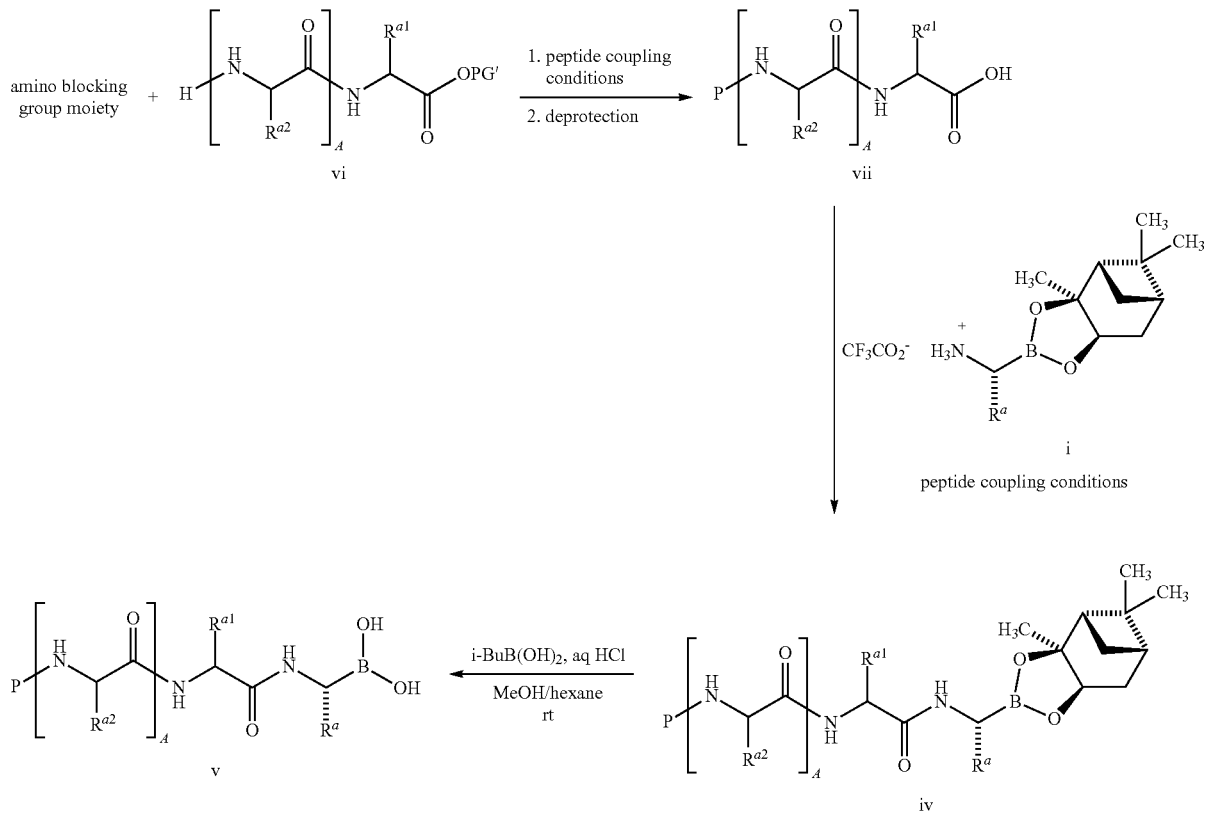

Alternatively, the order of coupling reactions can be reversed, as shown in Scheme 2. Thus, an O-protected amino acid vi is first coupled with an amino-group blocking moiety, followed by ester hydrolysis, to form compound vii. Optionally, PG' is H and ester hydrolysis is not needed, leading directly to compound vii. Coupling with compound i and boronic acid deprotection are then accomplished as described above for Scheme 1 to afford compound v.

Compound v is reacted with the appropriate alpha-hydroxy carboxylic acid or beta-hydroxy carboxylic acid to afford the compound of formula (I) as shown in Scheme 3.

The conversion of v to the compound of formula (I) can be accomplished under esterification conditions employing approximately a molar equivalent of the alpha-hydroxy carboxylic acid or beta-hydroxy carboxylic acid in a solvent such as ethyl acetate at a temperature of between about 40° C. and about 80° C. The conversion of v to the compound of formula (I) can also be accomplished as described above employing a molar excess of the alpha-hydroxy carboxylic acid or beta-hydroxy carboxylic acid. Examples of other suitable solvents for this conversion include, but are not limited to, methyl isobutyl ketone, acetone, acetonitrile, 2-methyltetrahydrofuran, anisole, isopropyl acetate, dimethoxyethane, tetrahydro- Scheme 3:

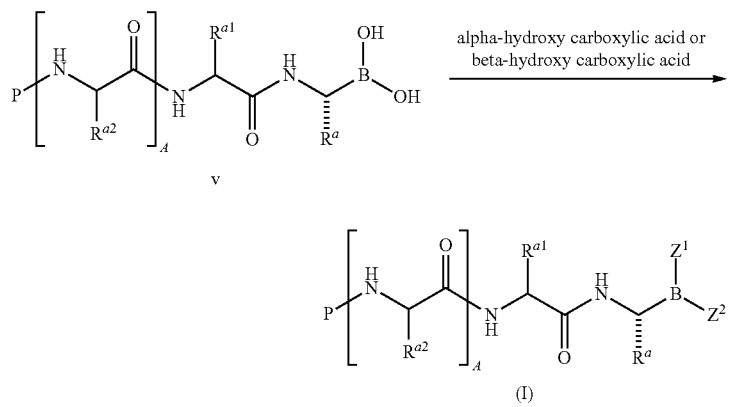

furan, dioxane, dichloromethane, toluene, heptane, methylcyclohexane, tert-butylmethyl ether, and mixtures thereof. The choice of the solvent will depend partly on the solubility of the alpha-hydroxy carboxylic acid or beta-hydroxy carboxylic acid used. The temperature selected for the conversion of v to the compound of formula (I) will depend partly on the boiling point of the solvent or solvent mixture used.

The conversion of v to the compound of formula (I) may be catalyzed by an organic amine base such as, but not limited to, triethylamine, triethylenediamine, pyridine, collidine, 2,6-lutidine, 4-dimethylaminopyridine, di-tertbutylpyridine, N-methylmorpholine, N-methylpiperidine, tetramethylguanidine, diazabicyclo[5.4.0]undec-7-ene (DBU), 1,4-diazabicyclo[2.2.2]octane, 1,5-diazabicycle[4.3.0]non-5-ene, N,N'diisopropylethylamine, or a mixture thereof.

The compound of formula v and the alpha-hydroxy carboxylic acid or beta-hydroxy carboxylic acid are heated together in the solvent of choice for a period of time. Following this period of time, the reaction mixture is allowed to cool for a period of time and the compound of formula (I) which precipitates upon cooling is collected by filtration. The cooling may be uncontrolled or may be controlled by the use of a cooling apparatus. The reaction mixture may be stirred during this cooling period. Alternatively, the compound of formula (I) can also be isolated from the reaction mixture by cooling followed by evaporation of the solvent. The reaction mixture may be seeded with crystals of the compound of formula (I) in order to effect precipitation.

A co-solvent such as, but not limited to, heptane, methylcyclohexane, toluene, tert-butylmethyl ether, ethyl acetate, or a mixture thereof, may be added during the cooling period. Following the addition of the co-solvent, the reaction mixture can be cooled further leading to the precipitation of the compound of formula (I). Alternatively, once the co-solvent is added, the reaction mixture can then be heated again to generate a homogenous solution, which is then cooled leading to the precipitation of the compound of formula (I). The reaction mixture may be seeded with crystals of the compound of formula (I) in order to effect precipitation.

In other embodiments, the compound of formula (I) is isolated in substantially pure form. In such embodiments, the purity is about 80%, about 85%, about 90%, about 91%, about 92%, about 93%, about 94%, about 95%, about 96%, about 97%, about 98%, about 99%, or about 99.5%.

In some embodiments, the compound of formula (I) is isolated in crystalline form. In some embodiments, the compound of formula (I) is isolated in substantially crystalline form. In some other embodiments, the compound of formula (I) is isolated in amorphous form.

The compound of formula (I) can also be generated by the co-lyophilization of compound v and the alpha-hydroxy carboxylic acid or beta-hydroxy carboxylic acid. This is accomplished by subjecting an aqueous solution comprising the compound of formula v and a molar excess of the alpha-hydroxy carboxylic acid or beta-hydroxy carboxylic acid to a lyophilization procedure. In some embodiments, the aqueous solution additionally comprises a water-miscible co-solvent. Examples of suitable co-solvents include, but are not limited to, tert-butyl alcohol, methanol, ethanol, and mixtures thereof. The co-lyophilization results in a composition that contains the compound of formula (I) and the excess alpha-hydroxy carboxylic acid or beta-hydroxy carboxylic acid.

Uses, Formulation, and Administration

The present invention provides compounds that are potent inhibitors of the proteasome. The compounds can be assayed in vitro or in vivo for their ability to inhibit proteasome-mediated peptide hydrolysis or protein degradation.

In another aspect, therefore, the invention provides a method for inhibiting one or more peptidase activities of a proteasome in a cell, comprising contacting a cell in which proteasome inhibition is desired with a compound described herein, or a pharmaceutically acceptable salt, boronic ester, or boronic acid anhydride thereof.

The invention also provides a method for inhibiting cell proliferation, comprising contacting a cell in which such inhibition is desired with a compound described herein. The phrase "inhibiting cell proliferation" is used to denote the ability of a compound of the invention to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compared to non-contacted cells. Thus, a proteasome inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I), or a pharmaceutically acceptable salt thereof, and a pharmaceutically acceptable carrier.

In some embodiments, the composition also comprises the free alpha-hydroxy carboxylic acid or a salt thereof or the beta-hydroxy carboxylic acid or a salt thereof. In such embodiments, the alpha-hydroxy carboxylic acid or a salt thereof or beta-hydroxy carboxylic acid or a salt thereof and the compound of formula (I) are present in a molar ratio ranging from about 2:1 to about 200:1. In various embodiments, the alpha hydroxy carboxylic acid or a salt thereof or beta-hydroxy carboxylic acid or a salt thereof and the compound of formula (I) are present in a ratio ranging from about 2:1 to about 200:1, from about 15:1 to about 80:1, or from about 20:1 to about 40:1.

If a pharmaceutically acceptable salt of the compound of the invention is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy,* 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as lithium, sodium and potassium salts; alkaline earth metal salts, such as calcium and magnesium salts; other multivalent metal salts, such as zinc salts; salts with organic bases, such as dicyclohexylamine, N-methyl-D-glucamine, t-butylamine, ethylene diamine, ethanolamine, and choline; and salts with amino acids such as arginine, lysine, and so forth.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "excipient" or "vehicle" are used interchangeably herein, and include any and all solvents, diluents, and other liquid vehicles, dispersion or suspension aids, surface active agents, pH modifiers, isotonic agents, thickening or emulsifying agents, preservatives, solid binders, lubricants and the like, as suited to the particular dosage form desired. *Remington: The Science and Practice of Pharmacy*, 20th Ed., ed. A. Gennaro, Lippincott Williams & Wilkins, 2000 discloses various carriers used in formulating pharmaceutically acceptable compositions and known techniques for the preparation thereof. Strickley, *Pharmaceutical Research*, 21(2) 201-230 (2004) reviews pharmaceutically acceptable excipients used in commercial products to solubilize compounds for oral or parenteral administration. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, carbonates, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, and mannitol, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins such as hydroxypropyl β-cyclodextrin and sulfobutylether β-cyclodextrin, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, cellulose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, crospovidone, cellulose, croscaramellose sodium, sodium starch glycolate, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, sodium stearyl fumarate, stearic acid, solid polyethylene glycols, sodium lauryl sulfate, glyceryl behenate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. In some embodiments, the excipients or carriers may include, but are not limited to sodium stearyl fumarate, carboxymethylcellulose, magnesium stearate, crospovidone, ethylcellulose, talc, and silicified microcrystalline cellulose.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the present invention provides pharmaceutical compositions comprising the compound of formula (I), and additional excipients described herein. In some other embodiments, the present invention provides pharmaceutical compositions comprising the compound of formula (II), and additional excipients described herein. In yet some other embodiments, the present invention provides pharmaceutical compositions comprising the compound of formula (III) or (IV), and additional excipients described herein.

In further embodiments, the present invention provides pharmaceutical compositions comprising the citrate ester of compound (VIII-1), and additional excipients described herein. In other further embodiments, the present invention provides pharmaceutical compositions comprising the citrate ester of compound (VIII-15), and additional excipients described herein. In further embodiments, the present invention provides pharmaceutical compositions comprising the citrate ester of (VIII-18) and additional excipients described herein.

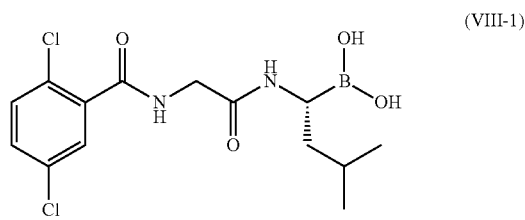

(VIII-1)

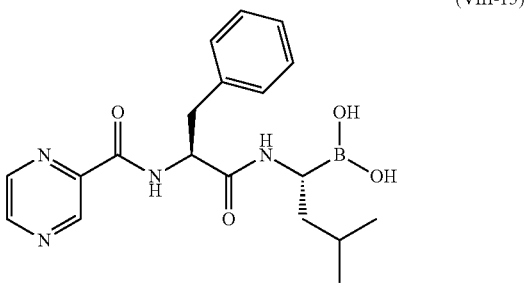

(VIII-15)

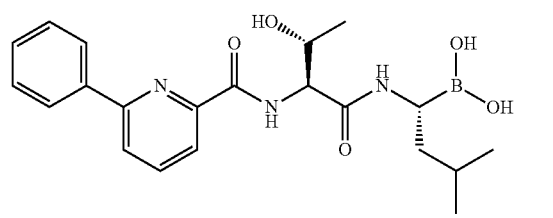

(VIII-18)

In further embodiments, the present invention provides pharmaceutical compositions comprising the compound (I-1), or a crystalline form thereof. In still yet further embodiments, the present invention provides pharmaceutical compositions comprising the compound (I-15), or a crystalline form thereof. In still yet some further embodiments, the present invention provides pharmaceutical compositions comprising the compound (I-18), or a crystalline form thereof.

The following description of pharmaceutical compositions and methods for preparation of said pharmaceutical compositions are applicable to the compounds of formulas (I), (II), (III), (IIIa), (IV), or (IVa) and various embodiments of these formulas as described herein. The following description of pharmaceutical compositions and methods for preparation of said pharmaceutical compositions are also applicable to the compounds (I-1), (I-15), or (I-18).

In one embodiment, the pharmaceutical composition comprises the compound of formula (I), wherein the compound of formula (I) is substantially crystalline. In another embodiment, the compound of formula (I) in the pharmaceutical composition is at least about 95%, 96%, 97%, 98%, 99%, 99.5%, 99.9% of a crystalline form. In yet another embodiment, the compound of formula (I) in the pharmaceutical composition is a crystalline form.

In some embodiments, the pharmaceutical formulations of the invention provide stable solid oral dosage forms of active compound, by using excipients having low water or low-moisture content, and manufactured using dry or non-aqueous formulation processes.

In one embodiment, the pharmaceutical composition is an oral pharmaceutical dosage form, selected from the group consisting of capsules, tablets, pills, powders, and granules. In another embodiment, the oral pharmaceutical dosage form is a capsule, wherein the capsule is a polymer-based capsule selected from the group consisting of gelatin, hydroxypropylmethyl cellulose (HPMC), fish gelatin, and pullulan. In yet another embodiment, the polymer-based capsule is selected from the group consisting of gelatin, and hydroxypropylmethyl cellulose. In still yet another embodiment, the polymer-based capsule is a hard gelatin capsule.

In one embodiment, the pharmaceutical composition comprises the compound of formula (I), or a crystalline form thereof, a filler, and optionally a lubricant. In another embodiment, the pharmaceutical composition comprises about 0.2% to about 3% of the compound of formula (I), or a crystalline form thereof; about 97% to about 99.8% of a filler; and optionally up to about 1.5% of a lubricant. In yet another embodiment, the pharmaceutical composition comprises about 0.25% to about 2% of the compound of formula (I), or a crystalline form thereof; and about 98% to about 99.75% of a filler.

In another embodiment, the pharmaceutical composition further comprises an optional flow-aid, and an optional buffer. In yet another embodiment, the pharmaceutical composition comprises about 0.2% to about 3% of the compound of formula (I), or a crystalline form thereof, about 86.5% to about 99.8% of a filler, optionally up to about 1.5% of a lubricant, optionally up to about 5% of a flow-aid, and optionally up to about 5% of a buffer, by weight as a percentage of total weight.

In another embodiment, the pharmaceutical composition comprises about 0.2% to about 12% of the compound of formula (I), or a crystalline form thereof, about 76.5% to about 99.8% of a filler, optionally up to about 1.5% of a lubricant, optionally up to about 5% of a flow-aid, and optionally up to about 5% of a buffer, by weight as a percentage of total weight.

In some embodiments, the compound of formula (I), or a crystalline form thereof, is present in the pharmaceutical composition in an amount of about 0.2% to about 3%, by weight as a percentage of total weight. In some other embodiments, the compound of formula (I), or a crystalline form thereof, is present in the pharmaceutical composition, in an amount of about 0.25% to about 2%, by weight as a percentage of total weight.

Suitable fillers include, but are not limited to, powdered cellulose, microcrystalline cellulose, silicified microcrystalline cellulose, high density microcrystalline cellulose, low-moisture microcrystalline cellulose, pregeletanized starch, sodium starch glycolate, and mixtures thereof. In some other embodiments, the filler is selected from the group consisting of powdered cellulose, microcrystalline cellulose, silicified microcrystalline cellulose, low-moisture microcrystalline cellulose, and mixtures thereof. In yet some other embodiments, the filler is low-moisture microcrystalline cellulose. In some further embodiments, the filler is selected from the group consisting of low-moisture microcrystalline cellulose, sodium starch glycolate, pregeletanized starch, and mixtures thereof.

In other embodiments, the filler is present in an amount of about 97% to about 99.8%, by weight as a percentage of total weight. In some other embodiments, the filler is present in an amount from about 98% to about 99.75%, by weight as a percentage of total weight. In yet some other embodiments, when a lubricant is present, the amount of filler is reduced by the corresponding percent amount of lubricant present. In some further embodiments, the filler is present in an amount of about 86.5% to about 99.8%, by weight as a percentage of total weight.

In some embodiments, the filler comprises a first filler and a second filler. The first filler is present in an amount of 0% to about 99.8%, by weight as a percentage of total weight, and the second filler is present in an amount of 0% to about 99.8% by weight as a percentage of total weight, as long as the total amount of filler is no greater than about 99.8%. In some embodiments, the first filler is present in an amount of about 40% to about 60%, by weight as a percentage of total weight, and the second filler is present in an amount of about 40% to about 60% by weight as a percentage of total weight, as long as the total amount of filler is not greater than about 99.8%, by weight as a percentage of total weight.

In some embodiments, the first filler is selected from the group consisting of low-moisture microcrystalline cellulose, sodium starch glycolate, pregeletanized starch, and mixtures thereof. In some embodiments, the second filler is selected from the group consisting of low-moisture microcrystalline cellulose, sodium starch glycolate, pregeletanized starch, and mixtures thereof.

Suitable lubricants include, but are not limited to, magnesium stearate, glyceryl behenate, hydrogenated vegetable oil, talc, zinc stearate, calcium stearate, sucrose stearate, sodium stearyl fumarate, and mixtures thereof. In some embodiments, the lubricant is magnesium stearate. In other embodiments, the lubricant is present in an amount of up to about 1.5%, by weight as a percentage of total weight. In yet some other embodiments, the lubricant is present in an amount of about 1%, by weight as a percentage of total weight.

Suitable flow-aids include, but are not limited to silicon dioxide, talc, and mixtures thereof. In some embodiments, the flow-aid is talc. In other embodiments, the flow-aid is present in an amount of up to about 5%, by weight as a percentage of total weight. In some other embodiments, the flow-aid is present in an amount of about 1%, by weight as a percentage of total weight. In yet some other embodiments, the flow-aid is present in an amount of about 2%, by weight as a percentage of total weight.

Suitable buffers include sodium citrate, citric acid, and mixtures thereof. In some embodiments, the buffer is sodium citrate. In some other embodiments, the buffer is present in an amount of up to about 5%, by weight as a percentage of total weight. In yet some other embodiments, the buffer is present in an amount of about 2%, by weight as a percentage of total weight.

In some embodiments, the pharmaceutical composition comprises the compound of formula (I), or a crystalline form thereof, a filler, and optionally a lubricant; wherein:
the alpha-hydroxy carboxylic acid or beta-hydroxy carboxylic acid is citric acid;
A is 0;
$R^a$ is isobutyl;
$R^{a1}$ is hydrogen, $C_{1-6}$ aliphatic, —$(CH_2)_m$—$CH_2$—$R^B$, or —$(CH_2)_m$—$CH(R^{5a})$—$OR^{5b}$;
P is $R^c$—C(O)—;
$R^c$ is —$R^D$;
M is 0 or 1;
the filler is selected from the group consisting of low-moisture microcrystalline cellulose, sodium starch glycolate, pregeletanized starch, and mixtures thereof; and
the lubricant, when present, is magnesium stearate.

In some embodiments, the pharmaceutical composition comprises the compound of formula (I), or a crystalline form thereof, a filler, and optionally a lubricant; wherein:
the compound of formula (I) is (I-1), (I-15) or (I-18);
the filler is selected from the group consisting of low-moisture microcrystalline cellulose, sodium starch glycolate, pregeletanized starch, and mixtures thereof; and
the lubricant, when present, is magnesium stearate.

In some embodiments, the pharmaceutical composition comprises about 0.25% to about 2% of the compound of formula (I), or a crystalline form thereof; and about 98% to about 99.75% of a filler; wherein:
the compound of formula (I) is (I-1), (I-15) or (I-18); and
the filler is selected from the group consisting of low-moisture microcrystalline cellulose, sodium starch glycolate, pregeletanized starch, and mixtures thereof.

In some embodiments, the pharmaceutical composition comprises the compound of formula (I), or a crystalline form thereof, a filler, optionally a lubricant; optionally a flow-aid; and optionally a buffer; wherein:
the alpha-hydroxy carboxylic acid or beta-hydroxy carboxylic acid is citric acid;
A is 0;
$R^a$ is isobutyl;
$R^{a1}$ is hydrogen, $C_{1-6}$ aliphatic, —$(CH_2)_m$—$CH_2$—$R^B$, or —$(CH_2)_m$—$CH(R^{5a})$—$OR^{5b}$;
P is $R^c$—C(O)—;
$R^c$ is —$R^D$;
m is 0 or 1;
the filler is selected from the group consisting of low-moisture microcrystalline cellulose, sodium starch glycolate, pregeletanized starch, and mixtures thereof;
the lubricant, when present, is magnesium stearate;
the flow-aid, when present, is talc; and
the buffer, when present, is sodium citrate.

In some embodiments, the pharmaceutical composition comprises the compound of formula (I), or a crystalline form thereof, a filler, optionally a lubricant; optionally a flow-aid; and optionally a buffer, wherein:
the compound of formula (I) is (I-1), (I-15) or (I-18);
the filler is selected from the group consisting of low-moisture microcrystalline cellulose, sodium starch glycolate, pregeletanized starch, and mixtures thereof;
the lubricant, when present, is magnesium stearate;
the flow-aid, when present, is talc; and
the buffer, when present, is sodium citrate.

In some embodiments, the pharmaceutical composition comprises about 0.2% to about 3% of the compound of formula (I), or a crystalline form thereof, about 86.5% to about 99.8% of a filler, optionally up to about 1.5% of a lubricant, optionally up to about 5% of a flow-aid, and optionally up to about 5% of a buffer, by weight as a percentage of total weight, wherein:
the compound of formula (I) is (I-1), (I-15) or (I-18);
the filler is selected from the group consisting of low-moisture microcrystalline cellulose, sodium starch glycolate, pregeletanized starch, and mixtures thereof;
the lubricant, when present, is magnesium stearate;
the flow-aid, when present, is talc; and
the buffer, when present, is sodium citrate.

In some embodiments, the pharmaceutical composition comprises the compound of formula (I), or a crystalline form thereof, a filler, and optionally a lubricant; wherein the compound of formula (I) is (I-1). In some other embodiments, the pharmaceutical composition comprises the compound of formula (I), or a crystalline form thereof, a filler, and optionally a lubricant; wherein the compound of formula (I) is (I-1); the filler is selected from the group consisting of low-moisture microcrystalline cellulose, sodium starch glycolate, pregeletanized starch, and mixtures thereof; and the lubricant, when present, is magnesium stearate.

In some embodiments, the pharmaceutical composition comprises the compound of formula (I), or a crystalline form thereof; wherein the compound of formula (I) is (I-1); and the crystalline form is Form 2.

In some embodiments, the pharmaceutical composition comprises the compound of formula (I-1) Form 2, and low-moisture microcrystalline cellulose. In some other embodiments, the pharmaceutical composition comprises the compound of formula (I-1) Form 2, and silicified microcrystalline cellulose. In yet some other embodiments, the pharmaceutical composition comprises the compound of formula (I-1) Form 2, low-moisture microcrystalline cellulose, and magnesium stearate. In still yet some further embodiments, the pharmaceutical composition comprises the compound of formula (I-1) Form 2, microcrystalline cellulose, and magnesium stearate.

In some embodiments, the pharmaceutical composition comprises the compound of formula (I-1) Form 2, low-moisture microcrystalline cellulose, and talc. In some other embodiments, the pharmaceutical composition comprises the compound of formula (I-1) Form 2, and pregeletanized starch. In yet some other embodiments, the pharmaceutical composition comprises the compound of formula (I-1) Form 2, pregeletanized starch, talc, and magnesium stearate. In still yet some other embodiments, the pharmaceutical composition comprises the compound of formula (I-1) Form 2, low-moisture microcrystalline cellulose, talc, and magnesium stearate. In some further embodiments, the pharmaceutical composition comprises the compound of formula (I-1) Form 2, low-moisture microcrystalline cellulose, talc, magnesium stearate, and sodium citrate. In some other further embodiments, the pharmaceutical composition comprises the compound of formula (I-1) Form 2, low-moisture microcrystalline cellulose, talc, magnesium stearate, and pregeletanized starch. In still yet some further embodiments, the pharmaceutical composition comprises the compound of formula (I-1) Form 2, low-moisture microcrystalline cellulose, talc, magnesium stearate, and sodium starch glycolate.

When the compound of formula (I) is subjected to hydrolytic conditions, the ester portion of the molecule is hydrolyzed to give the compound of formula (VIII) in a 1:1 molecular ratio.

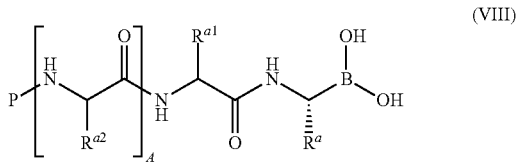

Using an analytical method that involves hydrolytic conditions for sample preparation, the amount of the compound of formula (VIII) present in a test sample is measured (see e.g. Analytical Test Method 1, below), by comparison to a reference standard of known purity. Using an analytical method that does not subject the sample to hydrolytic conditions, the amount of the compound of formula (VIII) present in the sample of the compound of formula (I) is measured by comparison to a reference standard of known purity (see e.g. Analytical Test Method 2 below). Therefore, the amount of the compound of formula (VIII) measured in Analytical Test Method 1 minus the amount of the compound of formula (VIII) measured in Analytical Test Method 2, gives the amount of the compound of formula (VIII) in the sample that is derived from hydrolysis of the compound of formula (I). Based on a 1:1 molecular ratio for the conversion of the compound of formula (I) to the compound of formula (VIII), a molecular weight conversion gives the amount of compound of formula (I) present in the test sample.

It will be recognized that such analytical methods as described directly above, and in the Experimental section below are applicable in a similar manner to any of the compounds of formulas (I), (II), (III), (IIIa), (IV), or (IVa) and various embodiments of these formula as described herein. Such analytical methods as described directly above and in the Experimental section below are applicable in a similar manner to the compounds (I-1), (I-15), or (I-18).

In some embodiments, the amount of the compound of formula (VIII) present in a pharmaceutical composition is determined by measuring the amount of the compound of formula (VIII) that is present after subjecting to the sample to conditions under which the compound of formula (I) is hydrolyzed to the compound of formula (VIII).

In some embodiments, the amount of the compound of formula (I-1), or a crystalline form thereof, present in a pharmaceutical composition is expressed as the equivalent amount on a molar weight basis of the compound of formula (VIII-1).

In some embodiments, the invention relates to a unit dose pharmaceutical composition comprising the compound of formula (I-1), or a crystalline form thereof.

In some other embodiments, the unit dose pharmaceutical composition comprises the compound of formula (I-1), or a crystalline form thereof, wherein the compound of formula (I-1) is present in an amount equivalent to a molar weight basis of about 0.1 mg to about 3.0 mg of the compound of formula (VIII-1). In yet some other embodiments, the unit dose pharmaceutical composition comprises the compound of formula (I-1), or a crystalline form thereof, wherein the compound of formula (I-1) is present in an amount equivalent to a molar weight basis of about 0.15 mg to about 2.2 mg of the compound of formula (VIII-1). In still yet some other embodiments, the unit dose pharmaceutical composition comprises the compound of formula (I-1), or a crystalline form thereof, wherein the compound of formula (I-1) is present in an amount equivalent to a molar weight basis of about 0.18 mg to about 0.22 mg of the compound of formula (VIII-1). In some further embodiments, the unit dose pharmaceutical composition comprises the compound of formula (I-1), or a crystalline form thereof, wherein the compound of formula (I-1) is present in an amount equivalent to a molar weight basis of about 0.46 mg to about 0.54 mg of the compound of formula (VIII-1). In still some further embodiments, the unit dose pharmaceutical composition comprises the compound of formula (I-1), or a crystalline form thereof, wherein the compound of formula (I-1) is present in an amount equivalent to a molar weight basis of about 1.80 mg to about 2.20 mg of the compound of formula (VIII-1).

In some embodiments, the amount of the compound of formula (I-1), or a crystalline form thereof, present in a pharmaceutical composition is expressed as the equivalent amount of the compound of formula (VIII-1), based on the relative molecular weights of the compound of formula (I-1) and the compound of formula (VIII-1).

In some embodiments, the unit dose pharmaceutical composition comprises about 0.143 mg to about 4.3 mg of the compound of formula (I-1), or a crystalline form thereof, measured as about 0.1 mg to about 3.0 mg of the compound of formula (VIII-1), on a weight for weight basis.

In some other embodiments, the unit dose pharmaceutical composition comprises about 0.214 mg to about 3.15 mg of the compound of formula (I-1), or a crystalline form thereof, measured as about 0.15 mg to about 2.2 mg of the compound of formula (VIII-1), on a weight for weight basis.

In yet some other embodiments, the unit dose pharmaceutical composition comprises about 0.258 mg to about 0.315 mg of the compound of formula (I-1), or a crystalline form thereof, measured as about 0.18 mg to about 0.22 mg of the compound of formula (VIII-1), on a weight for weight basis.

In still yet some other embodiments, the unit dose pharmaceutical composition comprises about 0.659 mg to about 0.773 mg of the compound of formula (I-1), or a crystalline form thereof, measured as about 0.46 mg to about 0.54 mg of the compound of formula (VIII-1), on a weight for weight basis.

In some further embodiments, the unit dose pharmaceutical composition comprises about 2.58 mg to about 3.15 mg of the compound of formula (I-1), or a crystalline form thereof, measured as about 1.80 mg to about 2.20 mg of the compound of formula (VIII-1), on a weight for weight basis.

In some embodiments, the invention provides a process for the production of an oral pharmaceutical dosage form of the compound of formula (I), or a crystalline form thereof, wherein the oral pharmaceutical dosage form is a capsule, comprising the steps of (a-1) mixing together screened filler and screened compound of formula (I), or a crystalline form thereof, in a bag;
(a-2) passing the resulting mixture from step (a-1) through a screen, then blending;
(a-3) screening additional filler through the same screen, passing it through the same bag, and blending in the same blending apparatus;
(a-4) repeating step (a-3) up to two times;
(a-5) taking the resulting mixture from step (a-4), and encapsulating it using a capsule-filling system; and
(a-6) weight-sorting the resulting capsules from step (a-5).

In some embodiments, step (a-3) may be repeated three or more times.

When a lubricant is present in the pharmaceutical composition, the invention provides a process for the production of an oral pharmaceutical dosage form of the compound of formula (I), or a crystalline form thereof, wherein the oral pharmaceutical dosage form is a capsule, comprising the steps of (b-1) mixing together screened filler, and screened compound of formula (I), or a crystalline form thereof, in a bag;
(b-2) passing the resulting mixture from step (b-1) through a screen, then blending;
(b-3) screening additional filler through the same screen, passing it through the same bag, and blending in the same blending apparatus;
(b-4) repeating step (b-3) up to two times;
(b-5) blending together the mixture from step (b-4), and screened lubricant;
(b-6) taking the resulting mixture from step (b-5), and encapsulating it using a capsule-filling system; and
(b-7) weight-sorting the resulting capsules from step (b-6).

In some embodiments, step (b-3) may be repeated three or more times. When additional components are present in the pharmaceutical composition, such as buffer, second filler, or flow-aid, they may be added in any of steps (b-1) or (b-3). The total amount of each component of the pharmaceutical composition may be added in one step or may be broken into several amounts, which may or may not be of equal weight, and added in individual occurrences of steps (b-1) or (b-3).

In some embodiments, the invention provides a process for the production of an oral pharmaceutical dosage form of the compound of formula (I), or a crystalline form thereof, wherein the oral pharmaceutical dosage form is a capsule, comprising the steps of
(c-1) passing filler through a screen, then placing in a high shear mixing apparatus;
(c-2) passing the compound of formula (I), or a crystalline form thereof, through a screen, then placing in the same high shear mixing apparatus;
(c-3) passing filler through a screen, then placing in the same high shear mixing apparatus;
(c-4) mixing using the same high shear mixing apparatus for less than 10 minutes;
(c-5) taking the resulting mixture from step (c-4), and encapsulating it using a capsule-filling system; and
(c-6) weight-sorting the resulting capsules from step (c-5).

In some embodiments, when using the high shear mixing apparatus, additional components that are present in the pharmaceutical composition may be added by repeating either step (c-1) or step (c-3).

In some embodiments, the compound of formula (I) used in the processes for preparation of solid oral dosage forms described above is selected from the group consisting of (I-1), (I-15), and (I-18). In some embodiments, the compound of formula (I) used in the processes for preparation of solid oral dosage forms described above is (I-1).

The process steps outlined above can take place using conventional apparatus and equipment. For a review, see e.g. *Remington: The Science and Practice of Pharmacy*, 21$^{st}$ Ed., Lippincott Williams & Wilkins, 2005.

The blending steps outlined above can take place in any conventional blending apparatus. In some embodiments, the blending time for each individual blending step is between about 1 minute and about 45 minutes. In some other embodiments, the blending time for each individual blending step is between about 1 minute and about 20 minutes. In yet some other embodiments, the blending time for each individual blending step is between about 2 minutes and about 15 minutes.

The mixing step outlined above can take place in any conventional polyethylene bag. In some embodiments, the mixing step takes between about 30 seconds and 5 minutes. In some embodiments, the mixing step outlined above can take place in a stainless steel container.

The mixing step using the high shear mixing apparatus can take place in any conventional high shear mixing apparatus. An example of such a high shear mixing apparatus is sold as Lab High Shear Granulator (Key International, Inc., Englishtown, N.J.). In some embodiments, the mixing is performed for less than about 10 minutes. In some other embodiments, the mixing is performed for less than about 5 minutes.

The capsule filling step outlined above can take place in any conventional capsule filling system or apparatus. In some embodiments, the capsule filling system is semi-automated, and can handle small batch sizes. An example of such a capsule filling system is sold as In-Cap (Isopak Limited, Lincolnshire, Stamford, United Kingdom). In some embodiments, the capsule filling system is manual. An example of such a capsule filling apparatus is sold as ProFill 100 (Torpac, Inc., Fairfield, N.J., USA).

In some embodiments, the capsules are hard gelatin capsules, sold as Coni-Snap® (Capsugel, Peapack, N.J.). One of skill in the art will be able to select the appropriate capsule size and color. In some embodiments, the capsules have a fill weight of 85 mg, 120 mg, or 150 mg.

The weight-sorting step outlined above can take place using any conventional weight-sorting apparatus or machine. An example of a weight-sorting apparatus or machine is sold as the SADE SP Bench Top Tablet and Capsule Weight Sorter (AC Compacting LLC, North Brunswick, N.J., USA).

In some embodiments, the capsules are packaged in bottles, foil pouches or blister packs. In some other embodiments, the capsules are packaged in heat-induction sealed high-density polyethylene (HDPE) bottles. In another embodiment, the capsules are packaged in air-tight sealed foil pouches. In yet another embodiment, the capsules are packaged in foil-foil blister packs. In some other embodiments, the capsules are packaged with a desiccant.

The physical and chemical stability of the oral pharmaceutical dosage form may be tested in a conventional manner, for example, the measurement of dissolution, disintegration time, assay for the compound of formula (I) degradation products, after storage at different temperatures for different lengths of time.

In some other embodiments, the invention provides pharmaceutical compositions for parenteral use. In yet some other embodiments, the invention provides liquid pharmaceutical compositions for parenteral or oral use.

In some embodiments, the compound of formula (I) is formulated as a lyophilized powder, in a manner analogous to that described in Plamondon et al., WO 02/059131, hereby incorporated by reference in its entirety. In such embodiments, an aqueous mixture comprising a alpha-hydroxy carboxylic acid or a beta-hydroxy carboxylic acid is lyophilized to form the compound of formula (I).

In some embodiments, the lyophilized powder also comprises free alpha-hydroxy carboxylic acid, or beta hydroxy carboxylic acid. Preferably, the free alpha-hydroxy carboxylic acid or beta hydroxy carboxylic acid compound and the compound of formula (I) are present in the mixture in a molar ratio ranging from about 0.5:1 to about 100:1, more preferably from about 5:1 to about 100:1. In various embodiments wherein the alpha-hydroxy carboxylic acid or beta-hydroxy carboxylic acid compound is citric acid, the lyophilized powder comprises free citric acid and the corresponding boronate ester in a molar ratio ranging from about 10:1 to about 100:1, from about 20:1 to about 100:1, or from about 40:1 to about 100:1.

In some embodiments, the lyophilized powder comprises citric acid and a compound of formula (I), substantially free of other components. However, the composition can further comprise one or more other pharmaceutically acceptable excipients, carriers, diluents, fillers, salts, buffers, bulking agents, stabilizers, solubilizers, and other materials well known in the art. The preparation of pharmaceutically acceptable formulations containing these materials is described in, e.g., *Remington: The Science and Practice of Pharmacy*, 20th Ed., ed. A. Gennaro, Lippincott Williams & Wilkins, 2000, or latest edition, and Strickley, *Pharmaceutical Research*, 21(2) 201-230 (2004).

Upon dissolution in aqueous medium, equilibrium is established between the boronate ester compound of formula (I) and the corresponding free boronic acid compound. In some embodiments, equilibrium is reached quickly, e.g., within 1-15 minutes, after the addition of aqueous medium. The relative concentrations of boronate ester, boronic acid, and any intermediate species present at equilibrium is dependent upon parameters such as, e.g., the pH of the solution, temperature, the nature of the alpha-hydroxy carboxylic acid or beta-hydroxy carboxylic acid, and the ratio of the alpha-hydroxy carboxylic acid or beta-hydroxy carboxylic acid to boronate ester compound of formula (I) present in the lyophilized powder.

In some embodiments, the pharmaceutical composition comprises the compound of formula (I), a bulking agent, and a buffer. In some other embodiments, the pharmaceutical composition comprises the compound of formula (I), a bulking agent, and a buffer in a lyophilized powder.

In some embodiments, the compound of formula (I) is pre-formed. In some other embodiments, the compound of formula (I) is formed in situ, from the corresponding boronic acid of formula (VIII). In yet some other embodiments, the compound (I-1) is pre-formed. In still yet some other embodiments, the compound (I-15) is formed in situ from compound (VIII-15).

Suitable bulking agents include glycine. In some embodiments, the amount of the bulking agent present is about 1% weight/volume (w/v) to about 5% w/v. In some other embodiments, the amount of the bulking agent present is about 3% w/v.

Suitable buffers include sodium citrate, citric acid, and mixtures thereof. In some embodiments, the buffer is sodium citrate, and citric acid.

In some embodiments, the buffer is present in a concentration of about 45 mM to about 65 mM. In some other embodiments, the buffer is present in a concentration of about 50 mM to about 60 mM.

In some embodiments, the ratio of the buffer to the compound of formula (I) is from about 50:1 to about 10:1. In some other embodiments, the ratio of the buffer to the compound of formula (I) is from about 30:1 to about 10:1. In yet some other embodiments, the ratio of the buffer to the compound of formula (I) is about 20:1.

In some embodiments, the pH of the pharmaceutical composition is between about pH 4.7 and pH 6.1. The pH of the pharmaceutical composition can be adjusted using any suitable inorganic acid or organic acid.

In some embodiments, the pharmaceutical composition comprises the compound of formula (I), a bulking agent, and a buffer; wherein:
the alpha-hydroxy carboxylic acid or beta-hydroxy carboxylic acid is citric acid;
A is 0;
$R^a$ is isobutyl;
$R^{a1}$ is hydrogen, $C_{1-6}$ aliphatic, $-(CH_2)_m-CH_2-R^B$, or $-(CH_2)_m-CH(R^{5a})-OR^{5b}$;
P is $R^c-C(O)-$;
$R^c$ is $-R^D$;
m is 0 or 1;
the bulking agent is glycine; and
the buffer is sodium citrate, and citric acid.

In some embodiments, the pharmaceutical composition comprises the compound of formula (I), a bulking agent, and a buffer; wherein:
the compound of formula (I) is represented by compounds (I-1), (I-15) or (I-18);
the bulking agent is glycine; and
the buffer is sodium citrate, and citric acid.

In some embodiments, the pharmaceutical composition comprises the compound of formula (I), a bulking agent, and a buffer in a lyophilized powder; wherein:
the alpha-hydroxy carboxylic acid or beta-hydroxy carboxylic acid is citric acid;
A is 0;
$R^a$ is isobutyl;
$R^{a1}$ is hydrogen, $C_{1-6}$ aliphatic, $-(CH_2)_m-CH_2-R^B$, or $-(CH_2)_m-CH(R^{5a})-OR^{5b}$;
P is $R^c-C(O)-$;
$R^c$ is $-R^D$;
m is 0 or 1;
the bulking agent is glycine; and
the buffer is sodium citrate and citric acid.

In some embodiments, the pharmaceutical composition comprises the compound of formula (I), a bulking agent, and a buffer in a lyophilized powder; wherein:
the compound of formula (I) is represented by compounds (I-1), (I-15) or (I-18);
the bulking agent is glycine; and
the buffer is sodium citrate and citric acid.

In some embodiments, the pharmaceutical composition comprises the compound (I-1) in a lyophilized powder. In some other embodiments, the pharmaceutical composition comprises the compound (I-1), glycine, sodium citrate, and citric acid in a lyophilized powder. In yet some other embodiments, the pharmaceutical composition comprises the compound (I-15) in a lyophilized powder. In still yet some other embodiments, the pharmaceutical composition comprises the compound (I-15), glycine, sodium citrate, and citric acid in a lyophilized powder.

In some embodiments, the invention provides a unit dose pharmaceutical composition comprising the compound of formula (I-1), a bulking agent, and a buffer in a lyophilized powder. In some embodiments, the unit dose pharmaceutical composition comprises the compound of formula (I-1), glycine, sodium citrate, and citric acid in a lyophilized powder.

In some embodiments, the compound of formula (I-1) is present in the unit dose pharmaceutical composition in an amount equivalent on a molar weight basis of about 1 mg to about 10 mg of the compound of formula (VIII-1). In some embodiments, the compound of formula (I-1) is present in the unit dose pharmaceutical composition in an amount equivalent on a molar weight basis of about 1 mg to about 5 mg of the compound of formula (VIII-1). In some embodiments, the compound of formula (I-1) is present in the unit dose pharmaceutical composition in an amount equivalent on a molar weight basis of about 1.0 mg, about 1.5 mg, about 2.0 mg, about 2.5 mg, about 3.5 mg, about 4.0 mg, about 4.5 mg, or about 5.0 mg of the compound of formula (VIII-1). In some embodiments, the compound of formula (I-1) is present in the unit dose pharmaceutical composition in an amount equivalent on a molar weight basis of about 3.5 mg of the compound of formula (VIII-1).

In some embodiments, the amount of glycine present in the unit dose pharmaceutical composition is about 0.01 g to about 0.50 g. In some embodiments, the amount of glycine present in the unit dose pharmaceutical composition is about 0.03 g to about 0.250 g. In some embodiments, the amount of glycine present in the unit dose pharmaceutical composition is about 0.06 g to about 0.125 g.

In some embodiments, the sodium citrate and citric acid is present in the unit dose pharmaceutical composition in an amount equivalent to about 0.005 g to about 0.250 g of citrate ion. In some embodiments, the sodium citrate and citric acid is present in the unit dose pharmaceutical composition in an amount equivalent to about 0.025 g to about 0.125 g of citrate ion.

In some embodiments, the invention provides a unit dose pharmaceutical composition comprising the compound of formula (I-15), a bulking agent, and a buffer in a lyophilized powder. In some embodiments, the unit dose pharmaceutical composition comprises the compound of formula (I-15), glycine, sodium citrate, and citric acid in a lyophilized powder.

In some embodiments, the compound of formula (I-15) is present in the unit dose pharmaceutical composition in an amount equivalent on a molar weight basis of about 1 mg to about 10 mg of the compound of formula (VIII-15). In some embodiments, the compound of formula (I-15) is present in the unit dose pharmaceutical composition in an amount equivalent on a molar weight basis of about 1 mg to about 5 mg of the compound of formula (VIII-15). In some embodiments, the compound of formula (I-15) is present in the unit dose pharmaceutical composition in an amount equivalent on a molar weight basis of about 1.0 mg, about 1.5 mg, about 2.0 mg, about 2.5 mg, about 3.5 mg, about 4.0 mg, about 4.5 mg, or about 5.0 mg of the compound of formula (VIII-15). In some embodiments, the compound of formula (I-15) is present in the unit dose pharmaceutical composition in an amount equivalent on a molar weight basis of about 3.5 mg of the compound of formula (VIII-15).

In some embodiments, the amount of glycine present in the unit dose pharmaceutical composition is about 0.01 g to about 0.50 g. In some embodiments, the amount of glycine present in the unit dose pharmaceutical composition is about 0.03 g to about 0.250 g. In some embodiments, the amount of glycine present in the unit dose pharmaceutical composition is about 0.06 g to about 0.125 g.

In some embodiments, the sodium citrate and citric acid is present in the unit dose pharmaceutical composition in an amount equivalent to about 0.005 g to about 0.250 g of citrate ion. In some embodiments, the sodium citrate and citric acid is present in the unit dose pharmaceutical composition in an amount equivalent to about 0.025 g to about 0.125 g of citrate ion.

In another aspect, the invention provides a method for preparing the compound of formula (I) as a lyophilized powder; the method comprising the steps:
(d-1) combining:
  i. an aqueous solvent mixture;
  ii. the compound of formula (I);
  iii. a bulking agent; and
  iv. a buffer; to form a mixture; and
(d-2) lyophilizing the mixture.

In some embodiments, the compound of formula (I) is formed in situ from the corresponding compound of formula (VIII). Thus, the invention also provides a method for preparing the compound of formula (I) as a lyophilized powder; the method comprising the steps:
(e-1) combining:
  i. an aqueous solvent mixture;
  ii. the compound of formula (VIII);
  iii. a bulking agent; and
  iv. an alpha-hydroxy carboxylic acid, or a salt thereof; or a beta-hydroxy carboxylic acid, or a salt thereof; or a combination thereof; to form a mixture; and
(e-2) lyophilizing the mixture.

In some embodiments, the aqueous solvent mixture comprises one or more co-solvents in addition to water. In some embodiments, the co-solvent is miscible with water. In some other embodiments, the co-solvent is an alcohol including, but not limited to, ethanol, tert-butyl alcohol and mixtures thereof. In some other embodiments, the co-solvent is tert-butyl alcohol.

In some embodiments, the aqueous solvent mixture comprises about 1% v/v to about 40% v/v alcohol. In some other embodiments, the aqueous solvent mixture comprises about 3% v/v to about 10% v/v alcohol. In some other embodiments, the aqueous solvent mixture comprises about 3% v/v to about 6% v/v alcohol. In yet some other embodiments, the solvent mixture comprises about 3% v/v to about 6% v/v tert-butyl alcohol. In still yet some other embodiments, the solvent mixture comprises about 5% v/v tert-butyl alcohol.

In some embodiments, a method is provided for preparing the compound (I-1) as a lyophilized powder, the method comprising the steps:
(f-1) combining:
  i. water;
  ii. the compound (I-1);
  iii. glycine;
  iv. sodium citrate; and
  v. citric acid; to form a mixture; and
(f-2) lyophilizing the mixture.

In some embodiments, a method is provided for preparing the compound (I-15) as a lyophilized powder, the method comprising the steps:
(g-1) combining:
  i. an aqueous solvent mixture comprising water and tert-butyl alcohol;
  ii. the compound (VIII-15);
  iii. glycine;
  iv. sodium citrate; and
  v. citric acid; to form a mixture; and
(g-2) lyophilizing the mixture.

In some other embodiments, for the method described directly above, the amount of tert-butyl alcohol present in the aqueous solvent mixture is about 3% v/v to about 6% v/v.

The lyophilization or freeze-drying can be performed using any conventional lyophilizers or freeze-dryers. In some embodiments, the lyophilization comprises the steps: (i) loading the liquid mixture as prepared above, and freezing; (ii) annealing; (iii) second freeze cycle; (iv) drying under vacuum; and (v) secondary drying. The temperatures and times for each step will depend on the lyophilizer or freeze-dryer that is employed.

In some embodiments, the resulting lyophilized powder has a residual moisture content of less than about 2%. In some other embodiments, the resulting lyophilized powder has a residual moisture content of less than about 1%.

In another aspect, the invention provides a method for the preparation of a pharmaceutical composition of the compound of formula (I) as a liquid pharmaceutical dosage form, said method comprising the step of reconstituting a lyophilized powder of the compound of formula (I) with an aqueous solvent suitable for pharmaceutical administration. Suitable reconstitution solvents include, but are not limited to, water, saline, phosphate buffered saline (PBS), and mixtures thereof. In some embodiments, the reconstitution solvent is water, water for injection, saline, and mixtures thereof. In some other embodiments, the reconstitution solvent is water for injection. Following reconstitution, the liquid pharmaceutical dosage form can contain concentrations of the compound of formula (I) as described herein.

In some embodiments, a method is provided for the preparation of a pharmaceutical composition of the compound (I-1) as a liquid pharmaceutical dosage form, said method comprising the step of reconstituting a lyophilized powder of the compound (I-1) as described herein with an aqueous solvent suitable for pharmaceutical administration. In some embodiments, a method is provided for the preparation of a pharmaceutical composition of the compound (I-1) as a liquid pharmaceutical dosage form, said method comprising the step of reconstituting a lyophilized powder of the compound (I-1) as described herein with water for injection, or normal saline. In some embodiments, a method is provided for the preparation of a pharmaceutical composition of the compound (I-1) as a liquid pharmaceutical dosage form, said method comprising the step of reconstituting a lyophilized powder of the compound (I-1) as described herein with water for injection.

In some embodiments, a method is provided for the preparation of a pharmaceutical composition of the compound (I-15) as a liquid pharmaceutical dosage form, said method comprising the step of reconstituting a lyophilized powder of the compound (I-15) as described herein with an aqueous solvent suitable for pharmaceutical administration. In some embodiments, a method is provided for the preparation of a pharmaceutical composition of the compound (I-15) as a liquid pharmaceutical dosage form, said method comprising the step of reconstituting a lyophilized powder of the compound (I-15) as described herein with water for injection, or normal saline. In some embodiments, a method is provided for the preparation of a pharmaceutical composition of the compound (I-15) as a liquid pharmaceutical dosage form, said method comprising the step of reconstituting a lyophilized powder of the compound (I-15) as described herein with water for injection.

Upon reconstitution in a reconstitution solvent, an equilibrium is established between the compound of formula (I) and the corresponding boronic acid of formula (VIII). Typically, equilibrium is reached quickly within about 10-15 minutes after the addition of the reconstitution solvent. The relative concentrations of the boronate ester and boronic acid present at equilibrium is dependent upon the pH of the solution, temperature, and the ratio of the alpha-hydroxy or beta-hydroxy acid compound to boronic acid compound.

In another aspect, the invention provides a liquid pharmaceutical composition comprising the compound of formula (I), and additional excipients described herein. In some embodiments, the liquid pharmaceutical composition is suitable for parenteral use. In some other embodiments, the liquid pharmaceutical composition is suitable for oral use.

In such embodiments, the liquid pharmaceutical composition comprises the compound of formula (I), a buffer, and optionally a tonicity modifier.

In some embodiments, the ratio of the buffer to the compound of formula (I) is from about 50:1 to about 10:1. In some other embodiments, the ratio of the buffer to the compound of formula (I) is from about 30:1 to about 10:1. In yet some other embodiments, the ratio of the buffer to the compound of formula (I) is about 20:1.

In some embodiments, the buffer is present in a concentration of about 45 mM to about 65 mM. In some other embodiments, the buffer is present in a concentration of about 50 mM to about 60 mM.

Suitable buffers include sodium citrate, citric acid, and mixtures thereof. In some embodiments, the buffer is sodium citrate, and citric acid.

Suitable tonicity modifiers include, but are not limited to, amino acids such as arginine, histidine, and glycine; salts such as sodium chloride, potassium chloride, sodium citrate, propylene glycol; and mixtures thereof. In some embodiments, the tonicity modifier is propylene glycol. In some other embodiments, the tonicity modifier is sodium chloride.

Upon dissolution in a aqueous solvent mixture, an equilibrium is established between the compound of formula (I) and the corresponding boronic acid of formula (VIII). Thus, either a compound of formula (I) or a compound of formula (VIII) may be used in the preparation of the liquid pharmaceutical composition. Typically, equilibrium is reached quickly within about 10-15 minutes after the addition of the aqueous solvent mixture. The relative concentrations of the boronate ester and boronic acid present at equilibrium is dependent upon the pH of the solution, temperature, and the ratio of the alpha-hydroxy or beta-hydroxy acid compound to boronic acid compound. In some embodiments, the excess alpha-hydroxy or beta-hydroxy acid may act as a stabilizer, which pushes the equilibrium towards the boronate ester. In some embodiments, the tonicity modifier may also act as a stabilizer.

In some embodiments, the liquid pharmaceutical composition optionally further comprises a preservative.

In some embodiments, the liquid pharmaceutical composition comprises the compound of formula (I), a buffer, and optionally a tonicity modifier; wherein:
  the alpha-hydroxy carboxylic acid or beta-hydroxy carboxylic acid is citric acid;
  A is 0;
  $R^a$ is isobutyl;
  $R^{a1}$ is hydrogen, $C_{1-6}$ aliphatic, $-(CH_2)_m-CH_2-R^B$, or $-(CH_2)_m-CH(R^{5a})-OR^{5b}$;
  P is $R^c-C(O)-$;
  $R^c$ is $-R^D$;
  m is 0 or 1;
  the buffer is sodium citrate and citric acid; and
  the tonicity modifier, when present, is sodium chloride.

In some embodiments, the liquid pharmaceutical composition comprises the compound of formula (I), a buffer, and optionally a tonicity modifier; wherein:
  the compound of formula (I) is represented by compounds (I-1), (I-15) or (I-18);
  the buffer is sodium citrate and citric acid; and
  the tonicity modifier, when present, is sodium chloride.

In some embodiments, wherein the alpha-hydroxy carboxylic acid or beta-hydroxy carboxylic acid is citric acid, the liquid pharmaceutical composition of the compound of formula (I) comprises the compound of formula (I), water, citric acid, sodium citrate, and sodium chloride. In some other embodiments, wherein the alpha-hydroxy carboxylic acid or beta-hydroxy carboxylic acid is citric acid, the liquid pharmaceutical composition comprises the compound of formula (I), water, citric acid, and propylene glycol. In yet some other embodiments, the liquid pharmaceutical composition comprises the compound of formula (I), wherein the compound of formula (I) is the compound (I-1), water, citric acid, sodium citrate and sodium chloride.

In such embodiments, wherein the alpha-hydroxy carboxylic acid or beta-hydroxy carboxylic acid is citric acid, the liquid pharmaceutical dosage form of the compound of formula (I) has a pH of between about pH 3 and about pH 7. In certain such embodiments, the pH is between about pH 4.9 and about pH 6.7. In other certain such embodiments, the pH is between about pH 5.5 and about pH 6.5.

In some embodiments, wherein the alpha-hydroxy carboxylic acid or beta-hydroxy carboxylic acid is citric acid, the liquid pharmaceutical composition of the compound of formula (I) is prepared in situ from a stock vehicle solution and the compound of formula (VIII). In some embodiments, the stock vehicle solution comprises water, citric acid, sodium citrate and propylene glycol. In such embodiments, the resulting solution can be further diluted with stock vehicle solution or with a sodium chloride solution to generate liquid pharmaceutical compositions of the compound of formula (I) of desired concentrations.

In another aspect the invention provides a unit dose liquid pharmaceutical composition, comprising the compound of formula (I), a buffer, and optionally a tonicity modifier. In some embodiments, the unit dose liquid pharmaceutical composition comprises the compound of formula (I), a buffer, and optionally a tonicity modifier, wherein the compound of formula (I) is the compound (I-1). In some embodiments, the compound of formula (I) is present in the unit dose liquid pharmaceutical composition at a concentration of about 0.5 mg/ml to about 3 mg/ml of the compound of formula (VIII). In some other embodiments, the compound of formula (I) is present in the unit dose liquid pharmaceutical composition at a concentration of about 1 mg/ml of the compound of formula (VIII). In some other embodiments, wherein the compound of formula (I) is compound (I-1), the compound (I-1) in the unit dose liquid pharmaceutical composition is present at a concentration of about 0.5 mg/ml to about 3 mg/ml of the compound of formula (VIII-1). In yet some other embodiments, wherein the compound of formula (I) is compound (I-1), the compound (I-1) in the unit dose liquid pharmaceutical composition is present at a concentration of about 1 mg/ml of the compound of formula (VIII-1). In still yet some other embodiments, wherein the compound of formula (I) is the compound (I-15), the compound (I-15) in the unit dose liquid pharmaceutical composition is present at a concentration of about 1 mg/ml of the compound of formula (VIII-15).

In some embodiments in the unit dose liquid pharmaceutical composition, the sodium citrate and citric acid are present in an amount equivalent to about 0.005 g to about 0.250 g of citrate ion. In some embodiments in the unit dose liquid pharmaceutical composition, the sodium citrate and citric acid are present in an amount equivalent to about 0.025 g to about 0.125 g of citrate ion.

In some embodiments in the unit dose liquid pharmaceutical composition, the sodium chloride is present in an amount of about 0.0045 g to about 0.09 g. In some embodiments in the unit dose liquid pharmaceutical composition, the sodium chloride is present in an amount of about 0.01 g to about 0.04 g.

In some embodiments in the unit dose liquid pharmaceutical composition, the pharmaceutical composition is stored frozen until use.

In another aspect the invention provides a method for preparing the compound of formula (I), as a unit dose liquid pharmaceutical composition; the method comprising the steps:
(h-1) dissolving the buffer in an aqueous solvent;
(h-2) dissolving the compound of formula (I), or a crystalline form thereof, in the mixture obtained in step (h-1);
(h-3) dissolving the toncity modifier in the mixture obtained in step (h-2);
(h-4) adding further aqueous solvent to the required batch volume; and
(h-5) filling vials with an amount of the mixture obtained in step (h-4).

In some embodiments, the vials are capped after step (h-5). In some other embodiments, nitrogen is bubbled through the mixture prior to step (h-5). In yet some other embodiments, after step (h-5), the liquid in the vials can be overlayed with nitrogen prior to capping.

In some embodiments, the compound of formula (I) is formed in situ from the compound of formula (VIII). In such embodiments, in step (h-2), the compound of formula (VIII), or a crystalline form thereof, is added to the mixture. In some embodiments, the alpha-hydroxy acid or beta-hydroxy acid is added in step (h-2). In some other embodiments, the alpha-hydroxy acid or beta-hydroxy acid is present in step (h-1) as the buffer.

The pharmaceutical compositions of the invention preferably are formulated for administration to a patient having, or at risk of developing or experiencing a recurrence of, a proteasome-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in proteasome activity or the severity of a proteasome-mediated disorder. The amount of proteasome inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a proteasome-mediated disorder. As used herein, the term "proteasome-mediated disorder" includes any disorder, disease or condition which is caused or characterized by an increase in proteasome expression or activity, or which requires proteasome activity. The term "proteasome-mediated disorder" also includes any disorder, disease or condition in which inhibition of proteasome activity is beneficial.

For example, compounds and pharmaceutical compositions of the invention are useful in treatment of disorders mediated via proteins (e.g., NFκB, p27$^{Kip}$, p21$^{WAF/CIP1}$, p53) which are regulated by proteasome activity. Relevant disorders include inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis)), vascular proliferative disorders (e.g., atherosclerosis, restenosis), proliferative ocular disorders (e.g., diabetic retinopathy), benign proliferative disorders (e.g., hemangiomas), autoimmune diseases (e.g., multiple sclerosis, tissue and organ rejection), as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors or pharmaceutical compositions include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors or pharmaceutical compositions include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or pharmaceutical compositions of the invention are used to treat a patient having or at risk of developing or experiencing a recurrence in a cancer selected from the group consisting of multiple myeloma and mantle cell lymphoma.

In some embodiments, the proteasome inhibitor or pharmaceutical compositions of the invention is administered in conjunction with another therapeutic agent. The other therapeutic agent may also inhibit the proteasome, or may operate by a different mechanism. In some embodiments, the other therapeutic agent is one that is normally administered to patients with the disease or condition being treated. The proteasome inhibitor of the invention may be administered with the other therapeutic agent in a single dosage form or as a separate dosage form. When administered as a separate dosage form, the other therapeutic agent may be administered prior to, at the same time as, or following administration of the proteasome inhibitor of the invention.

In some embodiments, a proteasome inhibitor of formula (I), or pharmaceutical composition of the compound of formula (I) is administered in conjunction with an anticancer agent. As used herein, the term "anticancer agent" refers to any agent that is administered to a subject with cancer for purposes of treating the cancer.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

Abbreviations

DCM methylene chloride
DIPEA N,N'-diisopropylethyl amine
DMF N,N'-dimethylformamide
EDCI N-(3-dimethylaminopropyl)-N'-ethylcarbodiimide hydrochloride
EtOAc ethyl acetate
h hours
HPLC high performance liquid chromatography
MIBK methyl isobutyl ketone
PES polyethersulfone
TBTU 0-benzotriazol-1-yl-N,N,N',N'-tetramethyluronium tetrafluoroborate
TFA trifluoroacetic acid
THF tetrahydrofuran
HOBt 1-hydroxybenztriazole
LCMS liquid chromatography mass spectrum
min minutes General Methods $^1$H NMR:

The spectra are acquired at ambient temperature on a JOEL ECX-400 NMR spectrometer operating at 400 MHz for $^1$H NMR. The resulting FID's are transferred to a PC and processed using NUTS NMR processing software from Acorn NMR Inc. Chemical shifts are referenced to DMSO solvent, 2.50 ppm. A solvent blank is prepared by adding 0.75 mL of DMSO-d6 to the NMR tube. After a $^1$H spectrum is acquired on the solvent blank, the sample is added and completely dissolved.

Mass Spectrometry:

Mass spectrometry studies are run on a Thermo-Finnigan LCQ Deca-XP ion trap mass spectrometer. The electrospray ion source was used in both positive and negative modes with a high voltage of 5 Icy, sheath gas flow rate of 35 arb, capillary temperature of 275° C., capillary voltage of 9 V and tube lens offset of 35 V. An analyte was dissolved in acetonitrile to generate a 0.5 mg/ml solution. An Agilent 1100 HPLC system was used for LC-Mass spectrometry flow analysis. The pump flow rate was 1.0 ml/minute. 10 μl of each sample solution was injected from the autosampler into a T-joint. About 2% of the solution from the T-joint was infused into the mass spectrometer.

X-Ray Powder Diffractometry (XRPD):

X-ray powder diffraction patterns are acquired on either:
i) a Bruker AXS D8 Advance diffractometer. The data is collected over an angular range of 2.9° to 29.6° 2θ in continuous scan mode using a step size of 0.05° 2θ and a step time of 2 seconds. The sample is run under ambient conditions and prepared as a flat plate specimen using powder as received without grinding; or
ii) a PANalytical X'Pert Pro diffractometer. Each specimen is analyzed using Cu radiation produced using an Optix long fine-focus source. An elliptically graded multilayer mirror is used to focus the Cu K α X-rays of the source through the specimen and onto the detector. The specimen is sandwiched between 3-micron thick films, analyzed in transmission geometry, and rotated to optimize orientation statistics. A beam-stop is used to minimize the background generated by air scattering. Helium and the anti-scatter extension are not used. Soller slits are used for the incident and diffracted beams to minimize axial divergence. The diffraction patterns are collected using a scanning position-minimize axial divergence. The diffraction patterns are collected using a scanning position-sensitive detector (X'Celerator) located 240 mm from the specimen. Prior to the analyses, a silicon specimen (NIST standard reference material 640c) is analyzed to verify the position of the silicon 111 peak.

Differential Scanning Calorimetry (DSC):

Differential scanning calorimetry (DSC) data are collected on either:
i) a TA Instruments Q100 differential scanning calorimeter equipped with a 50 position auto-sampler. The energy and temperature calibration standard is indium. Samples are heated at a rate of 10° C. per minute between 25° C. and 300° C. A nitrogen purge flowing at 50 mL per minute is maintained over the sample during a scan. Between 1 mg and 3 mg of sample is analyzed. All samples are crimped in a hermetically sealed aluminum pan with a pinhole to alleviate the pressure accumulated from the solvent vapor; or
ii) a TA Instruments differential scanning calorimeter 2920. The sample is placed into an aluminum DSC pan and the weight is accurately recorded. The open pan is covered with a lid and then crimped. The sample cell is equilibrated at 25° C., and heated under a nitrogen purge at a rate of 10° C./min. Indium metal was used as the calibration standard.

Thermal Gravimetric Analysis (TGA):

Thermal gravimetric analysis (TGA) data are collected on a TA Instruments Q500 thermal gravimetric analyzer, calibrated with Nickel/Alumel and running at a scan rate of 10° C. per minute. A nitrogen purge flowing at 60 mL per minute is maintained over the sample during measurements. Typically 5 mg to 15 mg of sample is loaded onto a pre-tared platinum crucible.

Example 1

Synthesis of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1)

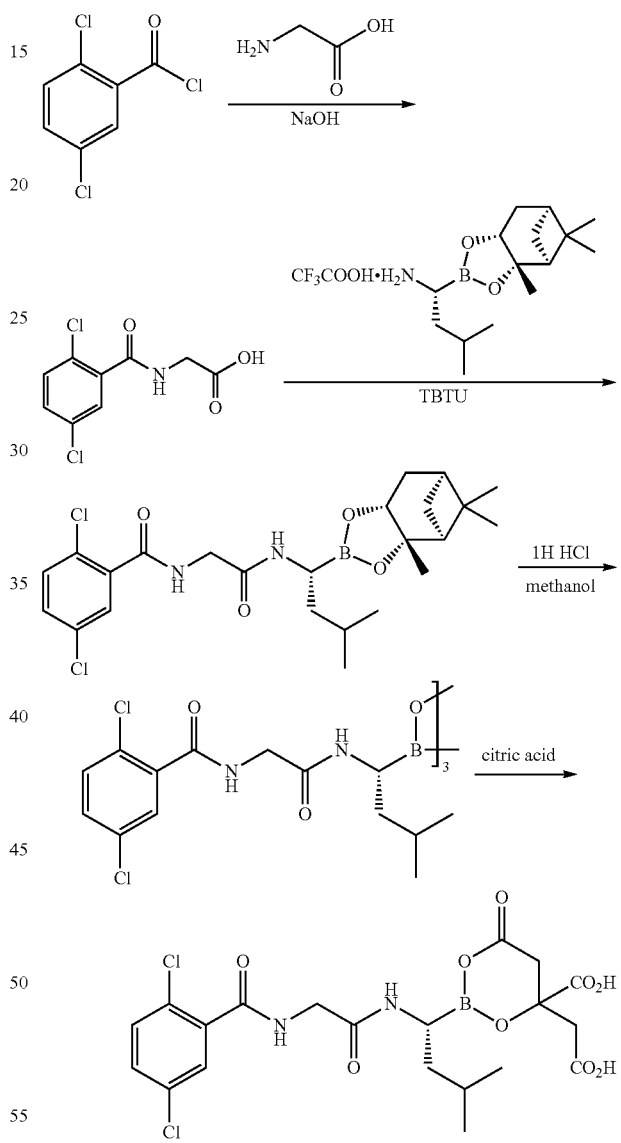

Step 1: 2,5-[(dichlorobenzoyl)amino]acetic acid

To a mixture of NaOH (12 g, 300 mmol) and glycine (18 g, 239 mmol) in water (120 mL) was added dropwise over 45 min a solution of 2,5-dichlorobenzoyl chloride (10 g, 48 mmol) in THF (15 mL) keeping the internal temperature below about 25° C. After 1 h, the mixture was acidified with 2.0 M HCl (125 mL) keeping the internal temperature below about 5° C. The resulting precipitate was collected by vacuum filtration. The crude product was recrystallized from water to give 2,5-[(dichlorobenzoyl)amino]acetic acid as a white, crystalline solid (6.1 g, 52%). mp 173.3° C. $^1$H NMR (300 MHz, DMSO-$d_6$, δ): 12.72 (bs, 1H), 8.89 (t, J=6.0 Hz, 1H), 7.54 (m, 2H), 7.48 (m, 1H), 3.93 (d, 0.1=6.0 Hz). $^{13}$C NMR (75 MHz, DMSO-$d_6$, δ): 41.6, 129.3, 129.6, 131.4, 132.2, 138.2, 171.4, 165.9. MS (m/z): [M+H] calculated for $C_9H_8Cl_2NO_3$, 248.0. found, 248.0; [M+Na] calculated for $C_9H_2Cl_2NNaO_3$, 270.0. found 270.2.

2,5-[(dichlorobenzoyl)amino]acetic acid was also be prepared via the following procedure: To a mixture of glycine (21.5 g, 286 mmol) in water (437 mL), was added 2.0 M NaOH (130 mL) and the resulting solution was cooled to 0° C. A solution of 2,5-dichlorobenzoyl chloride (50.0 g, 239 mmol) in THF (75 mL) was added dropwise at such a rate that the internal temperature was maintained at 0±1° C. During the addition, the pH was controlled at 11.0±0.2 using a pH controller titrated with 2.0 M NaOH. After complete addition, the mixture was stirred at 0±1° C. for an additional 2 h. The mixture was then acidified with 2.0 M HCl (176 mL) to a final pH of 2.5. The resulting precipitate was collected by filtration, washed with cold water (125 mL), and dried at 45° C. in a vacuum oven to afford 2,5-[(dichlorobenzoyl)amino]acetic acid as a white solid (57.6 g, 97.3%).

Step 2: 2,5-dichloro-N-[2-({(1R)-3-methyl-1-[(3aS, 4S,6S,7aR)-3a,5,5-trimethylhexahydro-4,6-methano-1,3,2-benzodioxaborol-2-yl]butyl}amino)-2-oxoethyl]benzamide To a solution of 2,5-[(dichlorobenzoyl)amino]acetic acid (6.10 g, 24.6 mmol) and TBTU (8.34 g, 26.0 mmol) in DMF (40 mL) with an internal temperature below about 5° C. was added (1R)-3-methyl-1-[(3aS,4 S,6S,7aR)-3a,5,5-trimethyl-hexahydro-4,6-methano-1,3,2-benzodioxaborol-2-yl]butan-1-amine.TFA (9.35 g, 24.7 mmol). DIPEA (13 mL, 75 mmol) was then added dropwise over 2 h keeping the internal temperature below about 5° C. After 40 min, the mixture was diluted with EtOAc (90 mL), washed with 5% NaCl (150 mL), twice with 10% NaCl (2×40 mL), once with 2% $K_2CO_3$ (1×40 mL), once with 1% $H_3PO_4$ (1×40 mL), and once with 10% NaCl (1×40 mL). The resulting organic layer was concentrated to a thick oil, diluted with heptane (40 mL) and evaporated to yield 2,5-dichloro-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide as a white solid which was used in the next step without purification.

Step 3: N,N',N''-{boroxin-2,4,6-triyltris[[(1R)-3-methylbutane-1,1-diyl]imino(2-oxoethane-2,1-diyl)]}tris(2,5-dichlorobenzamide)

To a solution of 2,5-dichloro-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide (12.2 g, 24.6 mmol) in methanol/hexane (1:1) (250 mL) were added 1N HCl (30 mL, 30 mmol) and (2-methylpropyl)boronic acid (6.5 g, 64 mmol). The reaction mixture was allowed to stir overnight. The phases were separated and the methanol layer was washed twice with additional heptane (2×55 mL). The resulting organic layer was concentrated to about 10 mL and partitioned between 2.0M NaOH (30 mL) and DCM (25 mL). The DCM layer was washed once with additional 2.0M NaOH (5 mL). The basic aqueous layers were then combined, washed twice with DCM (2×25 mL) and acidified with 1M HCl (60 mL). The resulting mixture was diluted with DCM (40 mL), the layers were separated, and the resulting aqueous layer was washed three times with DCM (3×10 mL). The combined DCM extracts were dried over MgSO4 (25 g) and evaporated to a thick oil. The product was precipitated with heptane (50 mL) and collected by filtration to yield N,N',N''-{boroxin-2,4,6-triyltris[[(1R)-3-methylbutane-1,1-diyl]imino(2-oxoethane-2,1-diyl)]}tris(2,5-dichlorobenzamide) as a white solid (6.6 g, 74%). $^1$H NMR (300 MHz, DMSO-$d_6$, δ): 8.93 (t, J=6.0 Hz, 1H), 8.68 (bs, 1H), 7.63 (m, 1H), 7.52 (m, 2H), 4.00 (d, J=6.0 Hz, 2H), 2.62 (m, 1H), 1.59 (m, 1H), 1.33 (m, 1H), 1.24 (m, 1H), 0.81 (d, J=5.9 Hz, 6H). $^{13}$C NMR (125 MHz, DMSO-$d_6$, δ): 23.2, 25.8, 40.1, 40.7, 43.0, 129.0, 130.0, 131.0, 137.5, 165.0, 172.5. MS (m/z) in $CH_3CN$: [M+H] calculated for $C_{42}H_{52}B_3Cl_6N_6O_9$, 1027.2. found, 1027.3; [M+Na] calculated for $C_{42}H_{51}B_3Cl_6N_6NaO_9$, 1049.2. found 1049.5.

Step 4: 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1)

Form 1:

To a solution of citric acid (2.75 g, 14.3 mmol) in EtOAc (85 mL) with an internal temperature of about 74° C. was added N,N',N''-{boroxin-2,4,6-triyltris[[(1R)-3-methylbutane-1,1-diyl]imino(2-oxoethane-2,1-diyl)]}tris(2,5-dichlorobenzamide) (5.00 g, 4.87 mmol) as a solid. The solution was cooled uncontrolled until the internal temperature was about 25° C. and the mixture was stirred overnight. The resulting precipitate was collected by filtration to yield 2,2'-{2-[(1R)-1-({[(2,5-dichlorobenzoyl)amino]acetyl}amino)-3-methylbutyl]-5-oxo-1,3,2-dioxaborolane-4,4-diyl}diacetic acid Form 1 as a crystalline solid (6.65 g, 88%). $^1$H NMR (500 MHz, DMSO-$d_6$, δ 110° C.): 10.08 (s, 1H), 8.69 (s, 1H), 7.61 (s, 1H), 7.52 (d, J=1.3 Hz, 2H), 4.26 (d, J=5.5 Hz, 2H), 2.70 (q, J=14.5 Hz, 4H), 2.70 (bs, 1H), 1.72 (sept, J=6.5 Hz, 1H), 1.42 (ddd, J=5.2 Hz, J=8.6 Hz, J=13.9 Hz, 1H), 1.28 (ddd, J=5.3, J=9.4 Hz, J=14.3 Hz, 1H), 0.91 (dd, J=3.3 Hz, J=6.6 Hz, 6H). MS (m/z) in $CH_3CN$: [M+Na] calculated for $C_{20}H_{23}BCl_2N_2NaO_9$, 539.1. found, 539.1.

The XRPD data for I-1 Form 1 is shown in FIG. 1 and in Table 1.

TABLE 1

| XRPD Data I-1 Form 1 | |
|---|---|
| Angle 2θ ° | Intensity % |
| 6.441 | 100 |
| 8.304 | 29.5 |
| 10.35 | 19 |
| 11.619 | 5.1 |
| 12.695 | 13.6 |
| 15.077 | 28.2 |
| 16.352 | 28.7 |
| 17.504 | 16.3 |
| 18.231 | 6 |
| 19.086 | 21.4 |
| 20.405 | 11.7 |
| 21.231 | 7.6 |
| 21.916 | 7.6 |
| 25.371 | 15.2 |
| 27.588 | 6.2 |

Figure 2:
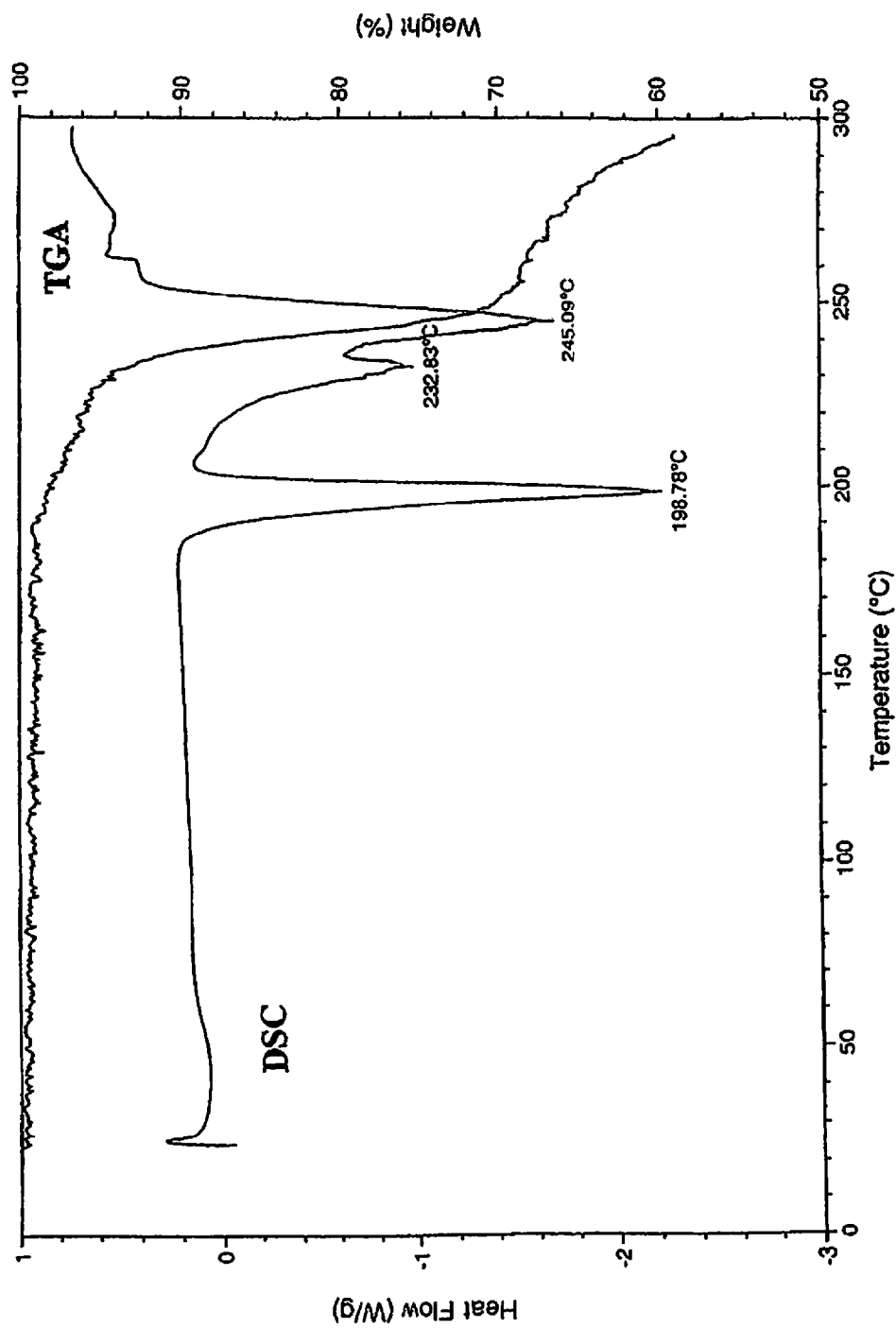
FIG. 2 is a differential scanning calorimetry (DSC)/thermal gravimetric analysis (TGA) profile for 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 1.

The Differential Scanning calorimetry (DSC) data for I-1 Form 1 is shown in FIG. 2. The profile is characterized by an endothermic transition with an onset temperature of 191.8° C. with a melt of 198.8° C. A second endothermic transition corresponding to decomposition has an onset temperature of 225° C. These temperatures have an error oft 5° C.

The Thermal Gravimetric Analysis (TGA) data for I-1 Form 1 is shown in FIG. 2. The profile graphs the percent loss of weight of the sample as a function of temperature, the temperature rate change being about 10° C./min. The weight loss represents a loss of about 0.72% of the weight of the sample as the temperature is changed from 50° C. to 200° C. These temperatures have an error of ±5° C.

Form 2: To a solution of citric acid (10.1 g, 52.6 mmol) in EtOAc (300 mL) with an internal temperature of about 74° C. was added a solution of N,N',N"-{boroxin-2,4,6-triyltris[[(1R)-3-methylbutane-1,1-diyl]imino(2-oxoethane-2,1-diyl)]}tris(2,5-dichlorobenzamide) (20.0 g, 19.5 mmol) in EtOAc (60 mL). The solution was cooled slowly (about 0.33° C./min) until the internal temperature was about 60° C. and the mixture was stirred for 3 h. The resulting slurry was cooled slowly (rate of about 0.12° C./min) until the internal temperature was about 25° C. and the mixture was stirred overnight. The resulting precipitate was collected by filtration to yield 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2 as a crystalline solid (26.7 g, 98%). $^1$H NMR (500 MHz, DMSO-d$_6$, δ 110° C.): 10.08 (s, 1H), 8.69 (s, 1H), 7.61 (s, 1H), 7.52 (d, J=1.3 Hz, 2H), 4.26 (d, J=5.5 Hz, 2H), 2.70 (q, J=14.5 Hz, 4H), 2.70 (bs, 1H), 1.72 (sept, J=6.5 Hz, 1H), 1.42 (ddd, J=5.2 Hz, J=8.6 Hz, J=13.9 Hz, 1H), 1.28 (ddd, J=5.3, J=9.4 Hz, J=14.3 Hz, 1H), 0.91 (dd, J=3.3 Hz, J=6.6 Hz, 6H). $^{13}$C NMR (100 MHz, DMSO-d$_6$, δ 100° C.): 21.65, 23.34, 25.09, 38.39, 38.98, 42.07, 76.25, 128.97, 129.14, 130.94, 131.48, 131.73, 137.05, 165.44, 170.23, 175.74, 177.43. MS (m/z) in CH$_3$CN: [M+Na] calculated for C$_{20}$H$_{23}$BCl$_2$N$_2$NaO$_9$, 539.1. found, 539.1.

4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2 was also prepared by adding a solution of citric acid (21 g, 0.11 mmol) in THF (80 mL) to a solution of N,N',N"-{boroxin-2,4,6-triyltris[[(1R)-3-methylbutane-1,1-diyl]imino(2-oxoethane-2,1-diyl)]}tris(2,5-dichlorobenzamide) (40 g, 0.11 mmol) in THF (80 mL) at 60° C. The solution was then seeded with Form 2 crystals (400 mg). After stirring for 30 min at 60° C., EtOAc (400 mL) was added over a period of 9 h. After complete addition of the EtOAc, the temperature was lowered to 20° C. over 5 h. The resulting suspension was filtered to collect 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2 as a crystalline solid (40 g, 70%).

4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2 was also prepared in the same general manner using the conditions described in Table 2.

TABLE 2

Additional conditions for preparation of I-1 Form 2

| Solvent | Initial Temperature | Seed Temperature | Isolated Yield I-1 Form 2 |
|---|---|---|---|
| acetonitrile | 80° C. | No seeding | 77% |
| MIBK | 80° C. | No seeding | 80% |
| 2-methyltetrahydrofuran | 80° C. | 60° C. | 72% |

4-(R,S)-(carboxymethyl)-2-((R)-1-(2-(2,5-dichlorobenzamido)acetamido)-3-methylbutyl)-6-oxo-1,3,2-dioxaborinane-4-carboxylic acid Form 2 was also prepared by dissolving in acetone followed by addition of EtOAc as an antisolvent.

Figure 3:
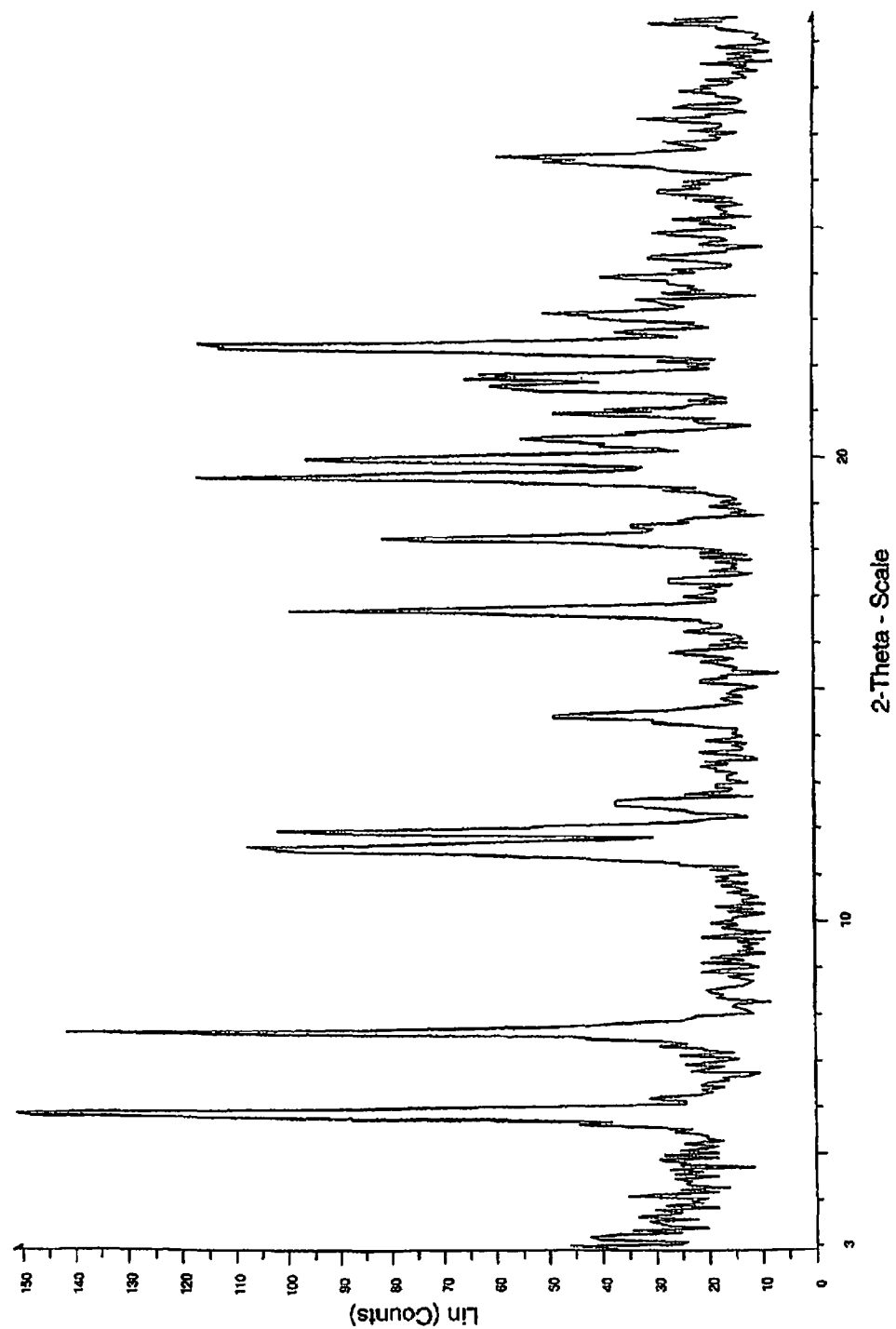
FIG. 3 is a powder X-ray diffractogram of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2.

The XRPD data for I-1 Form 2 is shown in FIG. 3 and in Table 3.

TABLE 3

XRPD Data I-1 Form 2

| Angle 2-θ ° | Intensity % |
|---|---|
| 5.817 | 100 |
| 7.614 | 93.4 |
| 11.575 | 71.1 |
| 11.896 | 67.1 |
| 12.571 | 24.3 |
| 14.43 | 32.2 |
| 16.689 | 65.8 |
| 17.362 | 17.8 |
| 18.232 | 53.9 |
| 19.596 | 77.6 |
| 19.959 | 63.8 |
| 20.376 | 36.2 |
| 20.998 | 32.2 |
| 21.5 | 40.1 |
| 21.764 | 43.4 |
| 22.407 | 77.6 |
| 23.12 | 33.6 |
| 23.901 | 26.3 |
| 24.402 | 20.4 |
| 24.882 | 19.7 |
| 25.764 | 19.1 |
| 26.464 | 39.5 |
| 27.347 | 21.7 |
| 27.65 | 17.1 |
| 27.979 | 16.4 |
| 29.41 | 20.4 |

Figure 4:
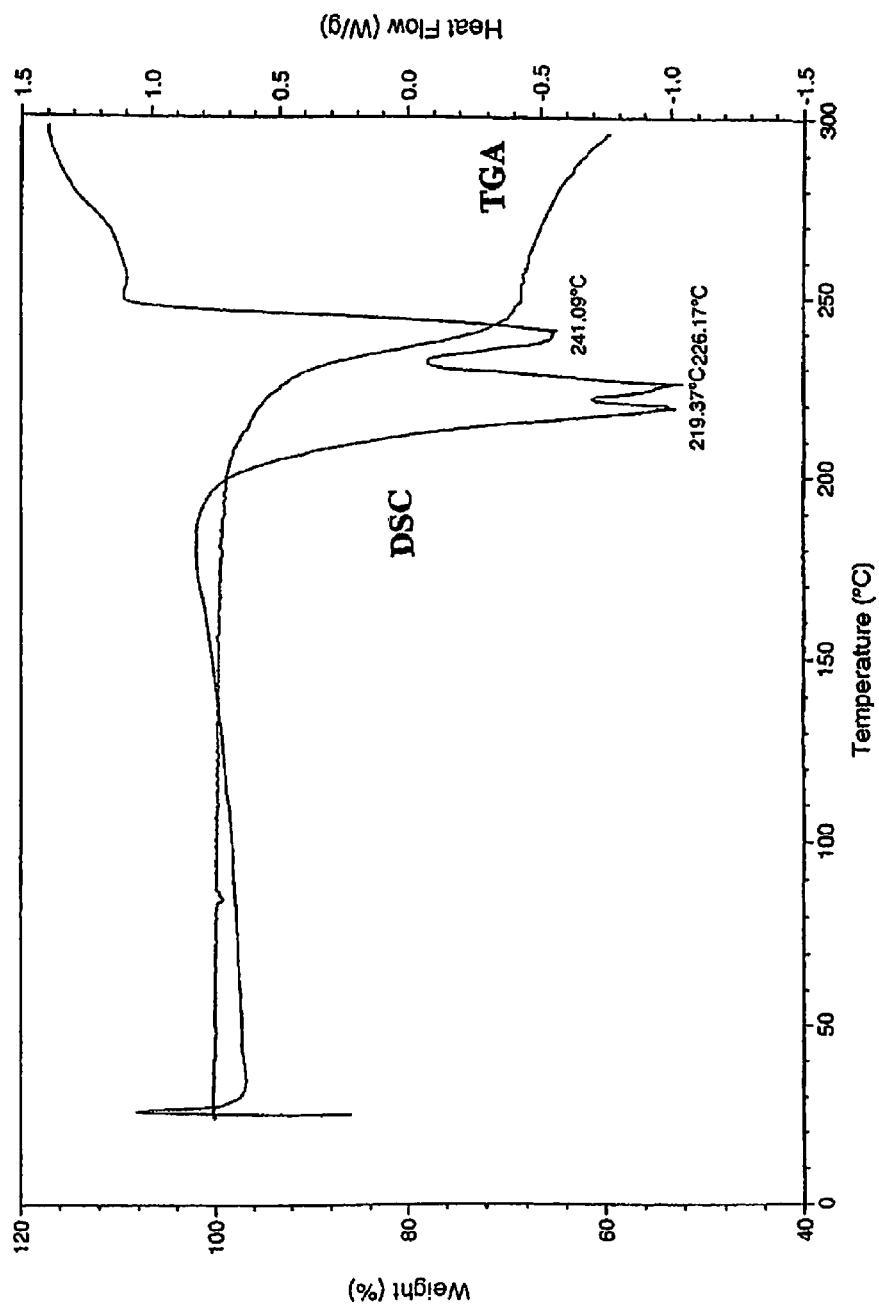
FIG. 4 is a differential scanning calorimetry (DSC)/thermal gravimetric analysis (TGA) profile for 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2.

The Differential Scanning calorimetry (DSC) data for I-1 Form 2 is shown in FIG. 4. The profile is characterized by an endothermic transition with an onset temperature of 206.5° C. with a melt of 219.9° C. A second endothermic transition corresponding to decomposition has an onset temperature of 225° C. These temperatures have an error oft 5° C.

The Thermal Gravimetric Analysis (TGA) data for I-1 Form 2 is shown in FIG. 4. The profile graphs the percent loss of weight of the sample as a function of temperature, the temperature rate change being about 10° C./min. The weight loss represents a loss of about 1.1% of the weight of the sample as the temperature is changed from 50° C. to 200° C. These temperatures have an error of ±5° C.

Example 1A

Alternate synthesis of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2

A 50-L glass reactor equipped with mechanical stirrer, dropping funnel, temperature indicator, and heating/cooling control unit (under nitrogen) was charged with 1.2 micron filtered EtOAc (18.9 kg) and anhydrous citric acid (0.561 kg, 2.9 mol). The mixture was heated to 71° C. and a solution resulted. N,N',N"-{boroxin-2,4,6-triyltris[[(1R)-3-methylbutane-1,1-diyl]imino(2-oxoethane-2,1-diyl)]}tris(2,5-dichlorobenzamide) (1.109 kg, 3.1 mol) dissolved in EtOAc (4.0 kg) was clarified using an in-line filter (1.2 micron), and the solution was added to the reaction mixture under stirring (193 rpm) over a period of 20 min while maintaining a temperature of 73° C. to 75° C. The stirring was reduced to 96 rpm and the mixture was cooled as follows: (1) The mixture was kept at 73° C. 75° C. for 25 min; (2) The mixture was stepwise cooled to 40° C. at the rate of approximately 5° C./30 min; (3) The mixture was allowed to cool uncontrolled overnight to ambient temperature with stirring. The product was then isolated by filtration, washed on the filter with 1.2 micron filtered EtOAc (2×1.2 kg), and dried under vacuum at 40-41° C. overnight (22 hours) to give 1.458 kg (92%) of the title compound. $^1$H NMR (400 MHz, DMSO-d$_6$, δ): 12.13 (s, 2H), 10.69 (s, 1H), 9.11 (t, J=5.6 Hz, 1H), 7.66 (t, J=1.2 Hz, 1H), 7.56 (d, J=1.2 Hz, 2H), 4.27 (bs, 2H), 2.9-2.55 (m, 5H), 1.67 (bs, 1H), 1.4-1.15 (bs, 2H), 0.86 (d, J=6.4 Hz, 6H).

Figure 7:
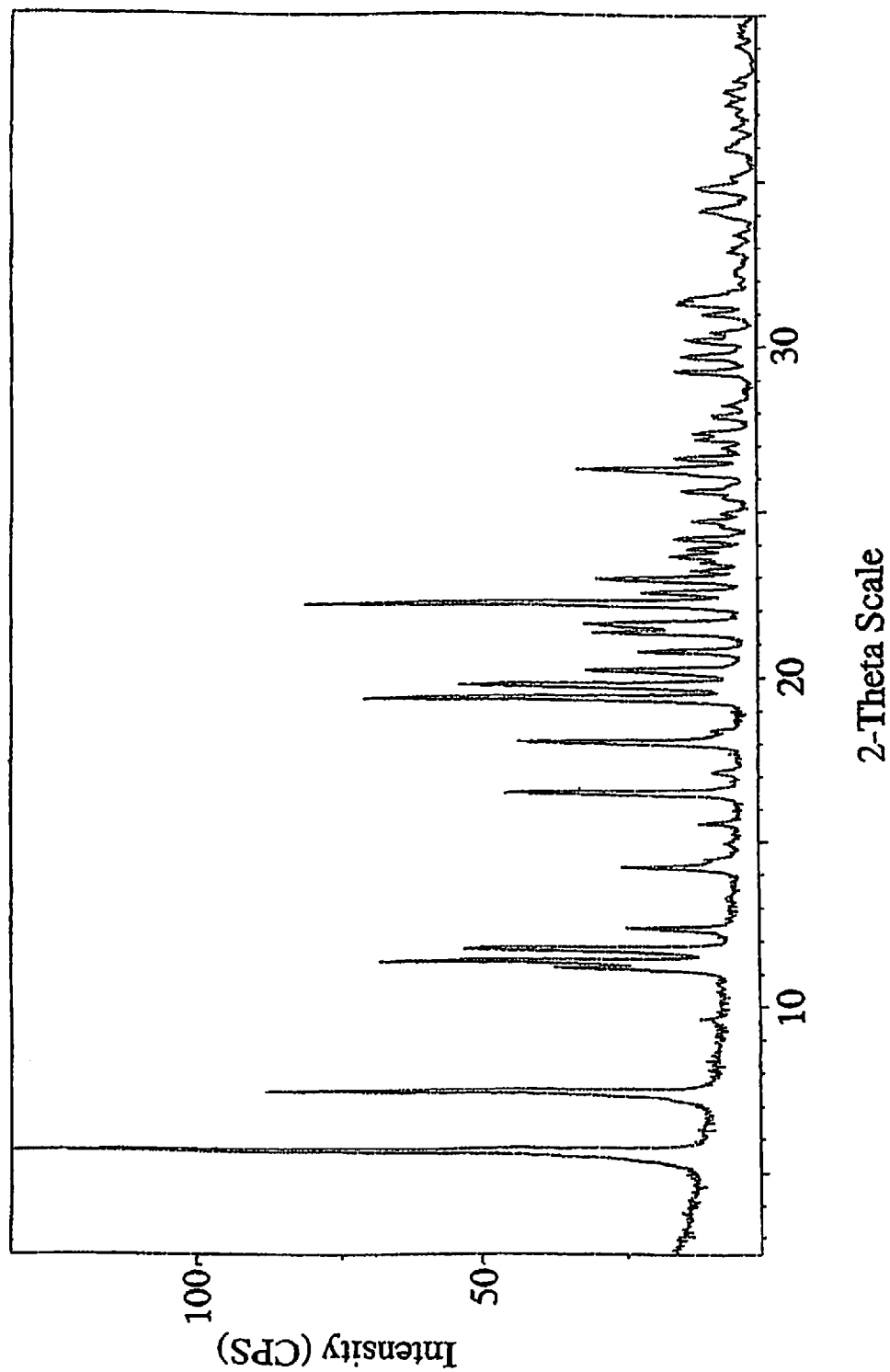
FIG. 7 is a powder X-ray diffractogram of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2.

The XRPD data for the compound (I-1) Form 2 is shown in FIG. 7 and in Table 6.

TABLE 6

| Angle 2-θ ° | Intensity % |
| --- | --- |
| 5.69 | 100 |
| 7.64 | 66 |
| 9.66 | 4 |
| 11.22 | 23 |
| 11.42 | 51 |
| 11.79 | 37 |
| 12.41 | 15 |
| 14.23 | 15 |
| 15.60 | 6 |
| 16.53 | 32 |
| 17.15 | 4 |
| 18.07 | 31 |
| 19.39 | 55 |
| 19.79 | 41 |
| 20.24 | 21 |
| 20.79 | 15 |
| 21.36 | 20 |
| 21.61 | 22 |
| 22.23 | 63 |
| 22.55 | 14 |
| 22.97 | 20 |
| 23.22 | 7 |
| 23.67 | 10 |
| 23.90 | 7 |
| 24.19 | 10 |
| 24.74 | 7 |
| 24.97 | 3 |
| 25.64 | 8 |
| 26.31 | 24 |
| 26.64 | 10 |
| 27.21 | 7 |
| 27.40 | 7 |
| 27.88 | 5 |
| 28.25 | 4 |
| 29.27 | 11 |
| 29.72 | 10 |

Figure 8:
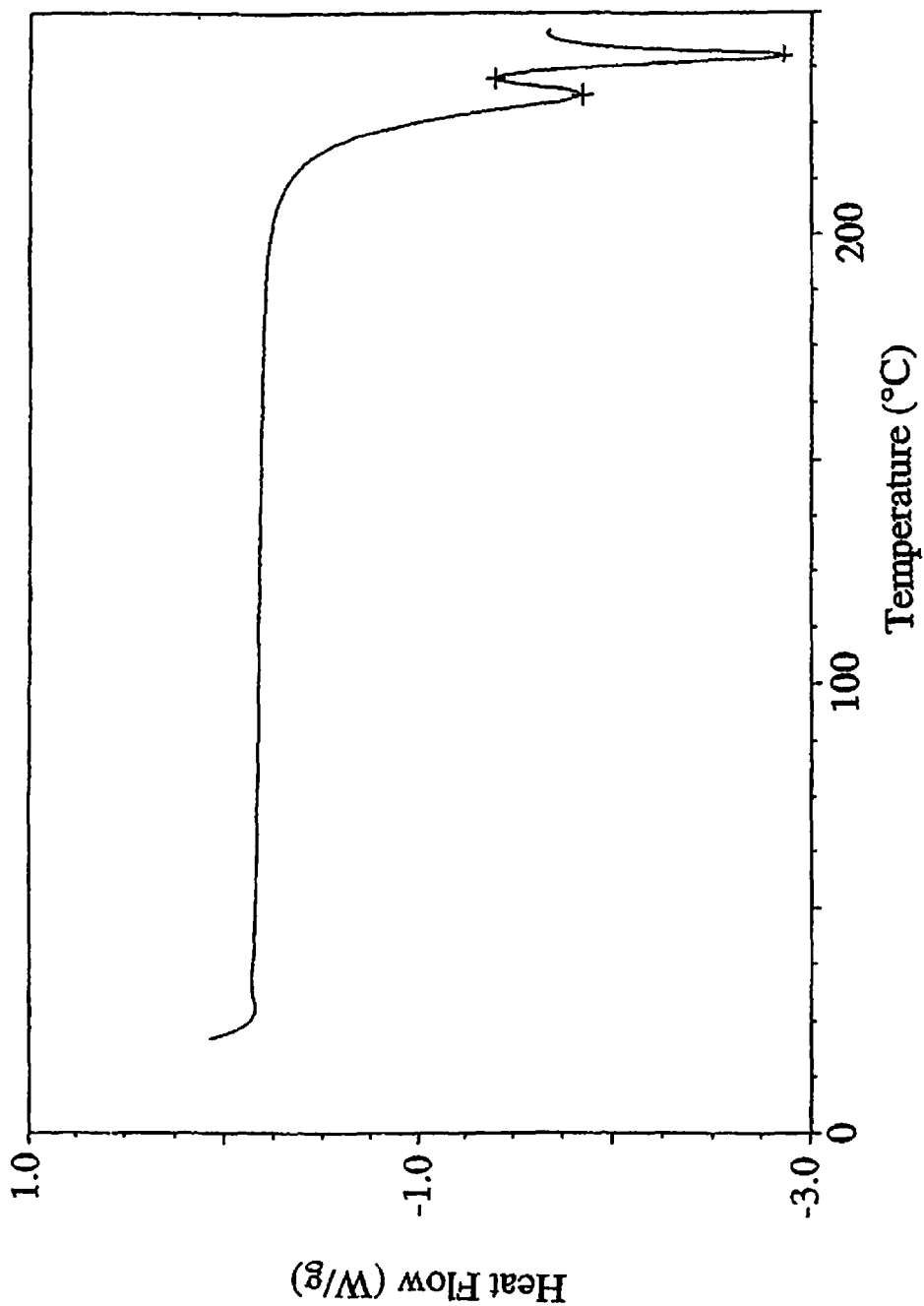
FIG. 8 is a differential scanning calorimetry (DSC) profile of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2.

The Differential Scanning calorimetry (DSC) data for the compound (I-1) Form 2 is shown in FIG. 8. The profile is characterized by two endothermic transitions; the first with a melt at about 231.3° C., and the second with a melt at about 239.9° C. These temperatures have an error off 5° C.

Example 2

Synthesis of 2,5-dichloro-N-(2-{[(1R)-3-methyl-1-(4-oxo-1,3,2-dioxaborolan-2-yl)butyl]amino}-2-oxoethyl)benzamide (I-2)

To a solution of glycolic acid (0.041 g, 0.54 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.199 g, 0.19 mmol) in EtOAc (1.0 mL). The solution was cooled uncontrolled until the internal temperature was about 25° C. and the solvent was removed by evaporation to yield 2,5-dichloro-N-(2-{[(1R)-3-methyl-1-(4-oxo-1,3,2-dioxaborolan-2-yl)butyl]amino}-2-oxoethyl)benzamide as a white solid (0.215 g, 95%). MS (m/z) in CH$_3$CN: [M+Et$_3$N+H] calculated for C$_{22}$H$_{35}$BCl$_2$N$_3$O$_5$, 502.2. found, 502.0. MS (m/z) in CH$_3$CN: [M−H] calculated for C$_{16}$H$_{18}$BCl$_2$N$_2$O$_5$, 399.1. found, 399.0.

Example 3

Synthesis of {(4S)-2-[(1R)-14{[(2,5-dichlorobenzoyl)amino]-acetyl}aminol-3-methylbutyl]-5-oxo-1,3,2-dioxaborolan-4-yl}acetic acid (I-3)

To a solution of L-malic acid (0.0958 g, 0.714 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.239 g, 0.233 mmol) in EtOAc (1.0 mL). The solution was cooled uncontrolled until the internal temperature was about 25° C. and the solvent was removed by evaporation to yield {(4S)-2-[(1R)-1-({[(2,5-dichlorobenzoyl)amino]-acetyl}amino)-3-methylbutyl]-5-oxo-1,3,2-dioxaborolan-4-yl}acetic acid as a white solid (0.307 g, 96%). MS (m/z) in CH$_3$CN: [M+Et$_3$N+H] calculated for C$_{24}$H$_{37}$BCl$_2$N$_3$O$_7$, 560.1. found, 560.1. MS (m/z) in CH$_3$CN: [M−H] calculated for C$_{18}$H$_{20}$BCl$_2$N$_2$O$_7$, 457.1. found, 457.1.

Example 4

Synthesis of 2,5-dichloro-N-[2-({(1R)-1-[(4S)-4-cyclohexyl-5-oxo-1,3,2-dioxaborolan-2-yl]-3-methylbutyl}amino)-2-oxoethyl]benzamide (I-4)

To a solution of (S)-hexahydromandelic acid (0.0881 g, 0.557 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-[2-({(1R)-1-[(4S)-4-cyclohexyl-5-oxo-1,3,2-dioxaborolan-2-yl]-3-methylbutyl}amino)-2-oxoethyl]benzamide as a white solid (0.251 g, 93%). MS (m/z) in CH$_3$CN: [M+Et$_3$N+H] calculated for C$_{28}$H$_{45}$BCl$_2$N$_3$O$_5$, 584.3. found, 584.1. MS (m/z) in CH$_3$CN: [M−H] calculated for C$_{22}$H$_{28}$BCl$_2$N$_2$O$_5$, 481.1. found 481.1.

Example 5

Synthesis of 2,5-dichloro-N-(2-{[(1R)-1-(4,4-dimethyl-5-oxo-1,3,2-dioxaborolan-2-yl)-3-methylbutyl]amino}-2-oxoethyl)benzamide (I-5)

To a solution of 2-hydroxyisobutyric acid (0.0567 g, 0.545 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-(2-{[(1R)-1-(4,4-dimethyl-5-oxo-1,3,2-dioxaborolan-2-yl)-3-methylbutyl]amino}-2-oxoethyl)benzamide as a white solid (0.225 g, 96%). MS (m/z) in CH₃CN: [M+Et₃N+H] calculated for $C_{24}H_{39}BCl_2N_3O_5$, 530.2. found, 530.0. MS (m/z) in CH₃CN: [M–H] calculated for $C_{18}H_{22}BCl_2N_2O_5$, 427.1. found, 427.0.

Example 6

Synthesis of 2,5-dichloro-N-[2-({(1R)-3-methyl-1-[(5R)-4-oxo-5-phenyl-1,3,2-dioxaborolan-2-yl]butyl}amino)-2-oxoethyl]benzamide (I-6)

To a solution of (R)-mandelic acid (0.168 g, 1.10 mmol) in EtOAc (2.0 mL) with an internal temperature of about 60° C. was added a solution of N,N',N"-{boroxin-2,4,6-triyltris[[(1R)-3-methylbutane-1,1-diyl]imino(2-oxoethane-2,1-diyl)]}tris(2,5-dichlorobenzamide) (0.382 g, 0.37 mmol) in EtOAc (1.0 mL). The solution was cooled uncontrolled until the internal temperature was about 25° C. and the resulting precipitate was collected by filtration to yield 2,5-dichloro-N-[2-({(1R)-3-methyl-1-[(5R)-4-oxo-5-phenyl-1,3,2-dioxaborolan-2-yl]butyl}amino)-2-oxoethyl]benzamide as a white solid (0.343 g, 65%). ¹H NMR (300 MHz, DMSO-d₆, δ): 10.88 (s, 1H), 9.22 (m, 1H), 7.68-7.27 (m, 8H), 5.15 (s, 1H), 4.33 (d, J=6.0 Hz, 2H), 2.8-2.76 (m, 1H), 1.71-1.62 (m, 1H), 1.50-1.28 (m, 2H), 0.89 (m, 6H). MS (m/z) in CH₃CN: [M+Et₃N+H] calculated for $C_{28}H_{39}BCl_2N_3O_5$, 578.2. found, 578.1. MS (m/z) in CH₃CN: [M–H] calculated for $C_{22}H_{22}BCl_2N_2O_5$, 475.1. found 475.1.

Example 7

Synthesis of 2,5-dichloro-N-[2-({(1R)-3-methyl-1-[(4S)-4-methyl-5-oxo-1,32-dioxaborolan-2-yl]butyl}amino)-2-oxoethyl]benzamide (I-7)

To a solution of L-lactic acid (0.675 g, 7.34 mmol) in EtOAc (3.0 mL) with an internal temperature of about 70° C. was added a solution of N,N',N"-{boroxin-2,4,6-triyltris[[(1R)-3-methylbutane-1,1-diyl]imino(2-oxoethane-2,1-diyl)]}tris(2,5-dichlorobenzamide) (2.50 g, 2.43 mmol) in EtOAc (7.5 mL). The solution was cooled uncontrolled until the internal temperature was about 60° C. After 30 min, heptane (11.5 mL) was added until the solution became turbid. The suspension was heated until the internal temperature was at or about 70° C., at which point a homogenous solution resulted. The solution was cooled at a rate of 0.17° C./min until the internal temperature was about 30° C., then cooled uncontrolled until until the internal temperature was about 0° C. The resulting precipitate was collected by filtration to yield 2,5-dichloro-N-[2-({(1R)-3-methyl-1-[(4S)-4-methyl-5-oxo-1,3,2-dioxaborolan-2-yl]butyl}amino)-2-oxoethyl]benzamide as a white, crystalline solid (2.32 g, 81%). MS (m/z) in CH₃CN: [M+Et₃N+H] calculated for $C_{23}H_{37}BCl_2N_3O_5$, 515.9. found, 516.0. MS (m/z) in CH₃CN: [M–H] calculated for $C_{17}H_{20}BCl_2N_2O_5$, 413.1. found 413.0.

Figure 5:
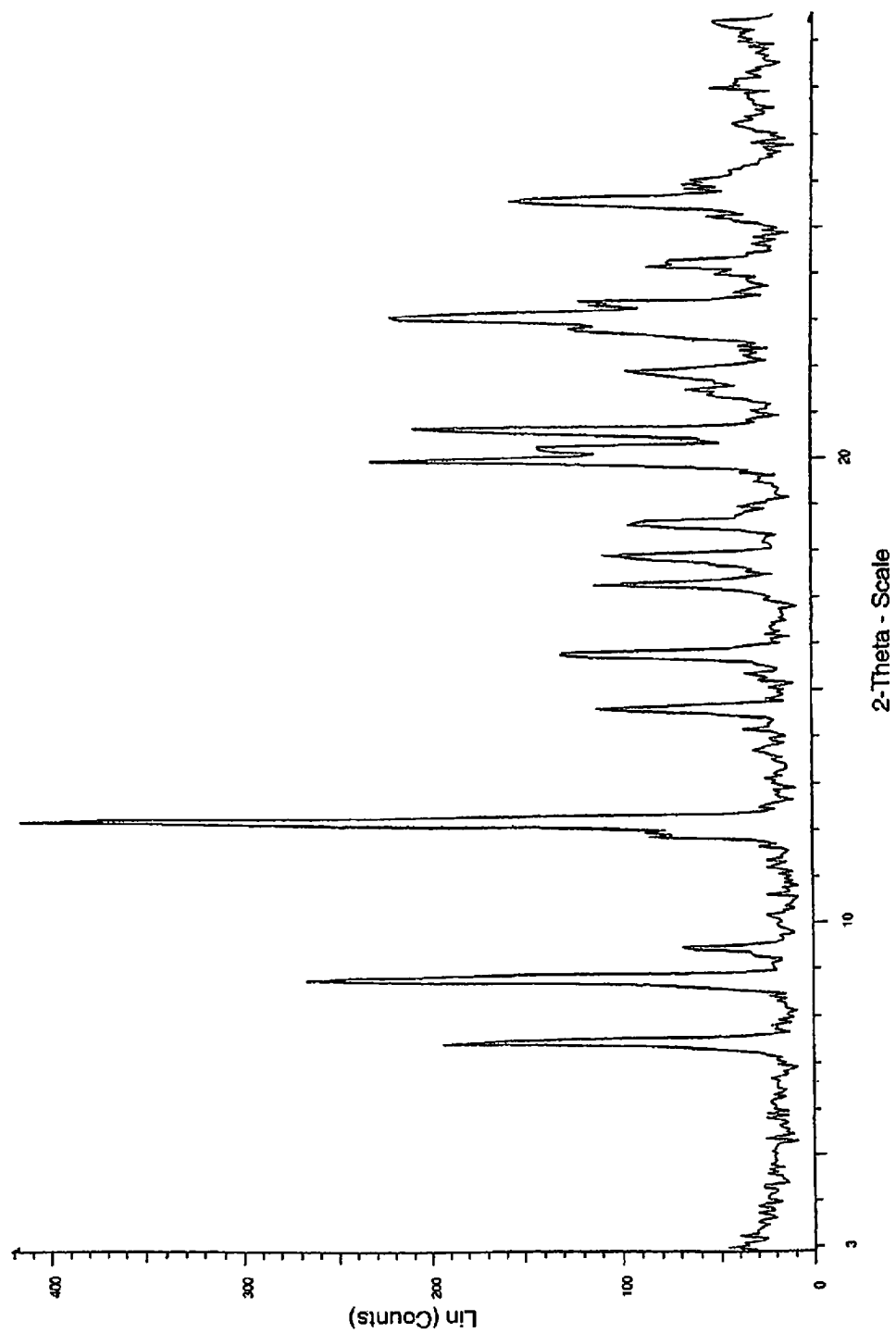
FIG. 5 is a powder X-ray diffractogram of 2,5-dichloro-N-[2-({(1R)-3-methyl-1-[(4S)-4-methyl-5-oxo-1,3,2-dioxaborolan-2-yl]butyl}amino)-2-oxoethyl]benzamide (I-7).

The XRPD data for I-7 is shown in FIG. 5 and in Table 4.

TABLE 4

| XRPD Data I-7 | |
|---|---|
| Angle 2-θ ° | Intensity % |
| 7.404 | 46 |
| 8.783 | 63.5 |
| 9.402 | 16.1 |
| 11.9 | 20.6 |

TABLE 4-continued

| XRPD Data I-7 | |
|---|---|
| Angle 2-θ ° | Intensity % |
| 12.195 | 100 |
| 13.71 | 7.3 |
| 14.594 | 26.5 |
| 15.302 | 8.3 |
| 15.772 | 31 |
| 17.299 | 26.8 |
| 17.859 | 25.8 |
| 18.549 | 22.7 |
| 19.943 | 55.5 |
| 20.214 | 33.9 |
| 20.606 | 50 |
| 21.48 | 15.6 |
| 21.887 | 23 |
| 22.75 | 30.1 |
| 23.028 | 53.1 |
| 23.334 | 28.9 |
| 24.243 | 18.2 |
| 25.2 | 13.3 |
| 25.566 | 37.7 |
| 27.221 | 10 |
| 29.103 | 9.2 |
| 29.383 | 12.6 |

Example 8

Synthesis of 2,5-dichloro-N-[2-({(1R)-3-methyl-1-[(4S)-4-methyl-6-oxo-1,3,2-dioxaborinan-2-yl]butyl}amino)-2-oxoethyl]benzamide (I-8)

To a solution of (S)-3-hydroxybutyric acid (0.0598 g, 0.566 mmol) in EtOAc (2.0 mL) with an internal temperature of about 60° C. was added a solution of N,N',N"-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-[2-({(1R)-3-methyl-1-[(4S)-4-methyl-6-oxo-1,3,2-dioxaborinan-2-yl]butyl}amino)-2-oxoethyl]benzamide as a white solid (0.225 g, 95%). ¹H NMR (300 MHz, DMSO-d₆, δ): 10.45 (s, 1H), 9.11 (t, J=6.0 Hz, 1H), 7.65 (m, 1H), 7.55 (m, 2H), 4.21 (d, J=6.0 Hz, 2H), 3.98-3.90 (m, 1H), 2.51 (m, 1H), 2.33 (dd, J₁=19.2 Hz, J=2.7 Hz, 1H), 2.24-2.21 (m, 1H), 1.61-1.52 (m, 1H), 1.33-1.19 (m, 2H), 1.07-1.04 (m, 3H), 0.84 (m, 6H). MS (m/z) in CH₃CN: [M+Et₃N+H] calculated for $C_{24}H39BCl_2N_3O_5$, 530.2. found, 530.0. MS (m/z) in CH₃CN: [M–H] calculated for $C_{18}H_{22}BCl_2N_2O_3$, 427.1. found, 427.1.

Example 9

Synthesis of 2,5-dichloro-N-(2-{[(1R)-1-(4,4-dimethyl-6-oxo-1,3,2-dioxaborinan-2-yl)-3-methylbutyl]amino}-2-oxoethyl)benzamide (I-9)

To a solution β-hydroxyisovaleric acid (0.0841 g, 0.712 mmol) in EtOAc (2.0 mL) with an internal temperature of about 60° C. was added a solution of N,N',N"-{boroxin-2,4,6-triyltris[[(1R)-3-methylbutane-1,1-diyl]imino(2-oxoethane-2,1-diyl)]}tris(2,5-dichlorobenzamide) (0.260 g, 0.253 mmol) in EtOAc (1.0 mL). The solution was cooled uncontrolled until the internal temperature was about 25° C. and the solvent was removed by evaporation to yield 2,5-dichloro-N-(2-{[(1R)-1-(4,4-dimethyl-6-oxo-1,3,2-dioxaborinan-2-yl)-

3-methylbutyl]amino}-2-oxoethyl)benzamide as a white solid (0.296 g, 95%). MS (m/z) in $CH_3CN$: [M+$Et_3$N+H] calculated for $C_{25}H_{41}BCl_2N_3O_5$, 544.3. found, 544.0. MS (m/z) in $CH_3CN$: [M–H] calculated for $C_{19}H_{24}BCl_2N_2O_5$, 441.1. found, 441.0.

Example 10

Synthesis of 2,5-dichloro-N-[2-({(1R)-1-[(4S)-4-tert-butyl-5-oxo-1,3,2-dioxaborolan-2-yl]-3-methylbutyl}amino)-2-oxoethyl]-2,5-dichlorobenzamide (I-10)

To a solution of (S)-2-hydroxy-3,3-dimethylbutyric acid (0.0712 g, 0.553 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-[2-({(1R)-1-[(4S)-4-tert-butyl-5-oxo-1,3,2-dioxaborolan-2-yl]-3-methylbutyl}amino)-2-oxoethyl]-2,5-dichlorobenzamide as a white solid (0.245 g, 97%). MS (m/z) in $CH_3CN$: [M+$Et_3$N+H] calculated for $C_{26}H_{43}BCl_2N_3O_5$, 558.3. found, 558.0. MS (m/z) in $CH_3CN$: [M–H] calculated for $C_{20}H_{26}BCl_2N_2O_5$, 455.1. found, 455.0.

Example 11

Synthesis of 2,5-dichloro-N-[2-({(1R)-1-[(4S)-4-isopropyl-5-oxo-1,3,2-dioxaborolan-2-yl]-3-methylbutyl}amino)-2-oxoethyl]benzamide (I-11)

To a solution of (S)-2-hydroxy-3-methylbutyric acid (0.0659 g, 0.558 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-[2-({(1R)-1-[(4S)-4-isopropyl-5-oxo-1,3,2-dioxaborolan-2-yl]-3-methylbutyl}amino)-2-oxoethyl]benzamide as a white solid (0.246 g, 99%). MS (m/z) in $CH_3CN$: [M+Na] calculated for $C_{19}H_{25}BCl_2N_2NaO_5$, 465.1. found, 465.1. MS (m/z) in $CH_3CN$: [M–H] calculated for $C_{19}H_{24}BCl_2N_2O_5$, 441.1. found, 441.0.

Example 12

Synthesis of 2,5-dichloro-N-[2-({(1R)-1-[(4S)-4-isobutyl-5-oxo-1,3,2-dioxaborolan-2-yl]-3-methylbutyl}amino)-2-oxoethyl]benzamide (I-12)

To a solution of 2-hydroxyisocaproic acid (0.0752 g, 0.569 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-[2-({(1R)-1-[(4S)-4-isobutyl-5-oxo-1,3,2-dioxaborolan-2-yl]-3-methylbutyl}amino)-2-oxoethyl]benzamide as a white solid (0.253 g, 95%). MS (m/z) in $CH_3CN$: [M+Na] calculated for $C_{20}H_{27}BCl_2N_2NaO_5$, 479.1. found, 479.1. MS (m/z) in $CH_3CN$: [M–H] calculated for $C_{20}H_{26}BCl_2N_2O_5$, 455.1. found 455.1.

Example 13

Synthesis of 2,5-dichloro-N-(2-{[(1R)-3-methyl-1-(4-oxo-4H-1,3,2-benzodioxaborinin-2-yl)butyl]amino}-2-oxoethyl)benzamide (I-13)

To a solution of salicylic acid (0.0758 g, 0.549 mmol) in EtOAc (2.0 mL) with an internal temperature of about 60° C. was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the resulting precipitate was collected by filtration to yield 2,5-dichloro-N-(2-{[(1R)-3-methyl-1-(4-oxo-4H-1,3,2-benzodioxaborinin-2-yl)butyl]amino}-2-oxoethyl)benzamide as a white solid (0.198 g, 78%). MS (m/z) in $CH_3CN$: [M+Na] calculated for $C_{21}H_{21}BCl_2N_2NaO_5$, 485.1. found, 485.1. MS (m/z) in $CH_3CN$: [M–H] calculated for $C_{21}H_{20}BCl_2N_2O_5$, 461.1. found, 461.0.

Figure 6:
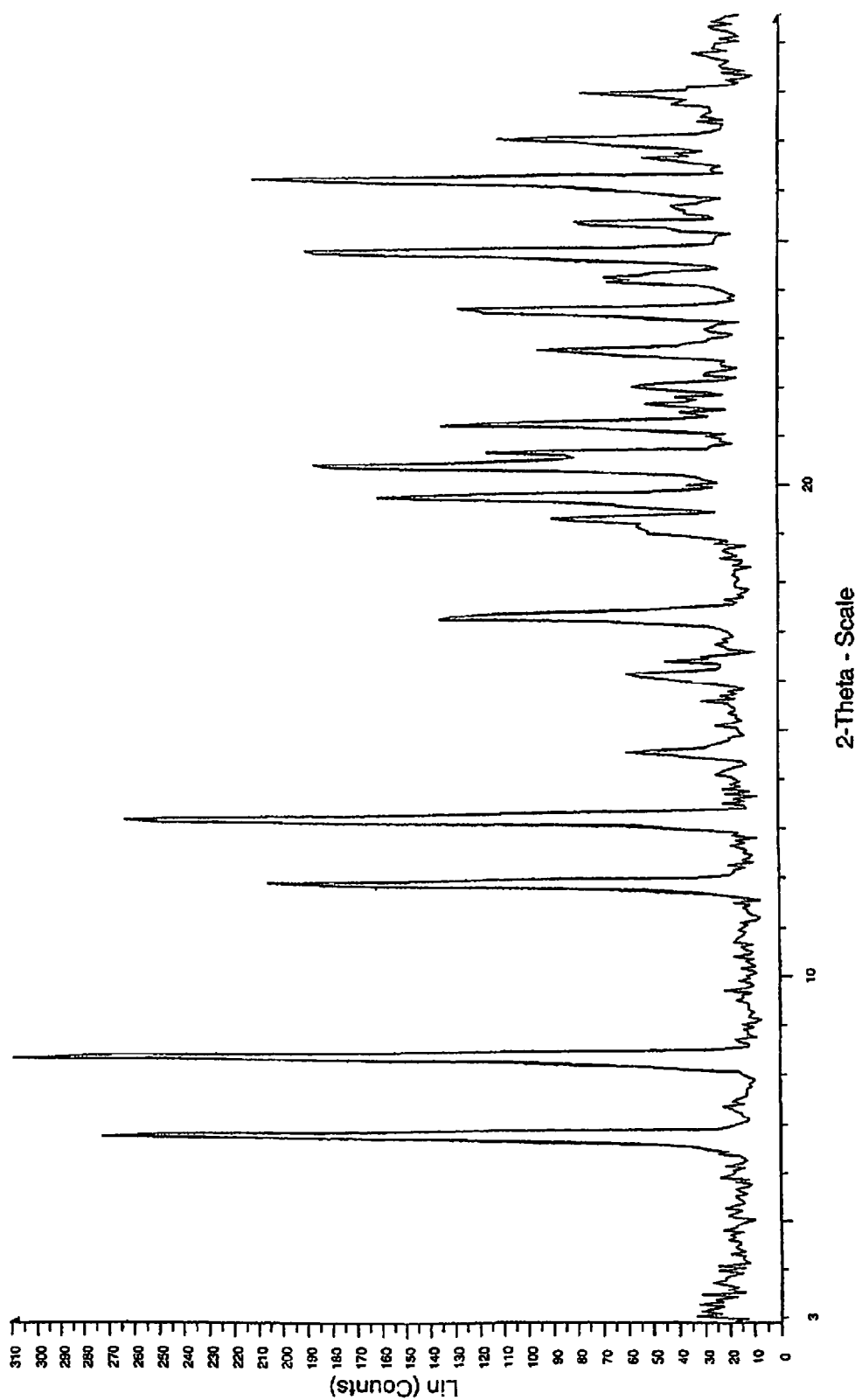
FIG. 6 is a powder X-ray diffractogram of 2,5-dichloro-N-(2-{[(1R)-3-methyl-1-(4-oxo-4H-1,3,2-benzodioxaborinin-2-yl)butyl]amino}-2-oxoethyl)benzamide (I-13).

The XRPD data for 1-13 is shown in FIG. 6 and in Table 5.

TABLE 5

| XRPD Data I-13 | |
|---|---|
| Angle 2-θ ° | Intensity % |
| 6.784 | 88.1 |
| 8.372 | 100 |
| 11.855 | 66.6 |
| 13.18 | 85.2 |
| 14.118 | 7.7 |
| 14.546 | 19.3 |
| 15.614 | 9.6 |
| 16.123 | 19.3 |
| 16.417 | 14.1 |
| 16.738 | 7.7 |
| 17.29 | 43.7 |
| 19.05 | 17.4 |
| 19.28 | 28.9 |
| 19.726 | 52.1 |
| 20.401 | 60.8 |
| 20.591 | 37.6 |
| 21.233 | 43.7 |
| 21.658 | 16.7 |
| 22.029 | 18.6 |
| 22.718 | 30.9 |
| 23.557 | 41.5 |
| 24.236 | 22.2 |
| 24.717 | 62.1 |
| 25.309 | 26 |
| 25.648 | 13.5 |
| 26.186 | 69.1 |
| 26.653 | 17.4 |
| 26.995 | 36.3 |
| 27.956 | 25.4 |
| 28.898 | 8.4 |
| 29.47 | 8.7 |

Example 14

Synthesis of 2,5-dichloro-N-(2-{[(1R)-3-methyl-1-(5-oxo-4,4-diphenyl-1,3,2-dioxaborolan-2-yl)butyl]amino}-2-oxoethyl)benzamide (I-14)

To a solution of benzilic acid (0.126 g, 0.552 mmol) in EtOAc (2.0 mL) with an internal temperature of about 60° C.

was added a solution of N,N',N''-{boroxin-2,4,6-triyltris[[(1R)-3-methylbutane-1,1-diyl]imino(2-oxoethane-2,1-diyl)]}tris(2,5-dichlorobenzamide) (0.200 g, 0.195 mmol) in EtOAc (1.0 mL). The solution was cooled uncontrolled until the internal temperature was about 25° C. and the solvent was removed by evaporation to yield 2,5-dichloro-N-(2-{[(1R)-3-methyl-1-(5-oxo-4,4-diphenyl-1,3,2-dioxaborolan-2-yl)butyl]amino}-2-oxoethyl)benzamide as a white solid (0.291 g, 95%). MS (m/z) in $CH_3CN$: [M+Na] calculated for $C_{28}H_{27}BCl_2N_2NaO_5$, 575.1. found, 575.2. MS (m/z) in $CH_3CN$: [M−H] calculated for $C_{28}H_{26}BCl_2N_2O_5$, 551.1. found, 551.1.

Example 15

Synthesis of 2,2'-{2-[(1R)-3-methyl-1-({(2S)-3-phenyl-2-[(pyrazin-2-ylcarbonyl)amino]propanoyl}amino)butyl]-5-oxo-1,3,2-dioxaborolane-4,4-diyl}diacetic acid (I-15)

To a solution of citric acid (0.257 g, 1.34 mmol) in EtOAc (7.4 mL) with an internal temperature of about 74° C. was added N,N',N''-(boroxin-2,4,6-triyltris{[(1R)-3-methylbutane-1,1-diyl]imino[(2S)-1-oxo-3-phenylpropane-1,2-diyl]})tripyrazine-2-carboxamide (0.500 g, 0.455 mmol) as a solid. The resulting solution was cooled uncontrolled until the internal temperature was about 25° C. and was evaporated to yield 2,2'-{2-[(1R)-3-methyl-1-({(2S)-3-phenyl-2-[(pyrazin-2-ylcarbonyl)amino]propanoyl}amino)butyl]-5-oxo-1,3,2-dioxaborolane-4,4-diyl}diacetic acid as a white solid (0.730 g, 99%). MS (m/z) in $CH_3CN$: [M+$Et_3N$+H] calcd for $C_{31}H_{45}BN_5O_9$, 642.3. found, 642.2. MS (m/z) in $CH_3CN$: [M−H] calcd for $C_{25}H_{28}BN_4O_9$, 539.2. found, 539.2.

Example 16

Synthesis of N-[(1S)-1-benzyl-2-({(1R)-3-methyl-1-[(5R)-4-oxo-5-phenyl-1,3,2-dioxaborolan-2-yl]butyl}amino)-2-oxoethyl]pyrazine-2-carboxamide (I-16)

To a solution of (R)-mandelic acid (0.0738 g, 0.485 mmol) in EtOAc (2.0 mL) with an internal temperature of about 60° C. was added N,N',N''-(boroxin-2,4,6-triyltris{[(1R)-3-methylbutane-1,1-diyl]imino[(2S)-1-oxo-3-phenylpropane-1,2-diyl]})tripyrazine-2-carboxamide (0.178 g, 0.162 mmol) as a solid. The solution was cooled uncontrolled until the internal temperature was about 25° C. and the resulting precipitate was collected by filtration to yield N-[(1S)-1-benzyl-2-({(1R)-3-methyl-1-[(5R)-4-oxo-5-phenyl-1,3,2-dioxaborolan-2-yl]butyl}amino)-2-oxoethyl]pyrazine-2-carboxamide as a white solid (0.195 g, 80%). MS (m/z) in $CH_3CN$: [M+Na] calculated for $C_{27}H_{29}BN_4NaO_5$, 523.2. found, 523.2. MS (m/z) in $CH_3CN$: [M−H] calculated for $C_{27}H_{28}BN_4O_5$, 499.2. found, 499.2.

Example 17

Synthesis of N-[(1S)-1-benzyl-2-({(1R)-3-methyl-1-[(5R)-4-oxo-5-phenyl-1,3,2-dioxaborolan-2-yl]butyl}amino)-2-oxoethyl]pyrazine-2-carboxamide (I-17)

To a solution of (S)-3-hydroxybutyric acid (0.0509 g, 0.489 mmol) in EtOAc (2.0 mL) with an internal temperature of about 60° C. was added N,N',N''-(boroxin-2,4,6-triyltris{[(1R)-3-methylbutane-1,1-diyl]imino[(2S)-1-oxo-3-phenylpropane-1,2-diyl]})tripyrazine-2-carboxamide (0.179 g, 0.163 mmol) as a solid. The solution was cooled uncontrolled until the internal temperature was about 25° C. and the solvent was removed by evaporation to yield N-[(1S)-1-benzyl-2-({(1R)-3-methyl-1-[(4S)-4-methyl-6-oxo-1,3,2-dioxaborinan-2-yl]butyl}amino)-2-oxoethyl]pyrazine-2-carboxamide as a white solid (0.213 g, 96%). MS (m/z) in $CH_3CN$: [M+Na] calculated for $C_{23}H_{29}BN_4NaO_5$, 475.2. found, 475.2. MS (m/z) in $CH_3CN$: [M−H] calculated for $C_{23}H_{28}BN_4O_5$, 451.2. found, 451.1.

Example 18

Preparation of formulations of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) for parenteral or oral administration Formulation A: A vessel was charged with 90 mL water and citric acid monohydrate (0.08 g) and sodium citrate dihydrate (1.5 g) were added and stirred until dissolved. To this solution, 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2 (0.142 g) was added, and the mixture was stirred until a solution was obtained. To this solution, sodium chloride (0.45 g) was added, and the pH was adjusted to pH 5.45 using 2N HCl. The final volume of the resulting solution was adjusted to 100 mL with water and filtered through a 0.2 μm PES membrane to yield Formulation A which was stored at −20° C.

Formulation B was prepared as for Formulation A, except that the pH was adjusted to pH 6.2 using 2N NaOH.

Formulation C: A vessel was charged with 90 mL water and citric acid monohydrate (0.08 g), sodium citrate dihydrate (1.5 g), and propylene glycol (1.0 g) were added and stirred until dissolved. To this solution, 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2 (0.142 g) was added, and the mixture was stirred until a solution was obtained. The pH was adjusted to 6.2 using 2N NaOH, and the final volume of the resulting solution was adjusted to 100 mL with water and filtered through a 0.2 μm PES membrane to yield Formulation C which was stored at −20° C.

Example 19

In situ preparation of formulations of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) for parenteral or oral administration Stock Formulation Vehicle: A vessel was charged with approximately 160 mL water and citric acid monohydrate (0.714 g) and sodium citrate dihydrate (2.24 g) were added and stirred until dissolved. To this solution, propylene glycol (2.0 g) was added, and the mixture was stirred until a homogeneous solution was obtained. The final pH was pH 5.14. The final weight of the resulting solution was adjusted to 200 g (assuming density of 1 g/mL) with water and filtered through a 0.2 μm PES membrane filter unit and stored at a temperature between about 2° C. and about 8° C.

Formulation Stock (1 mg/mL): To a vessel, 0.105 grams (approximately 95.4% purity) of N,N',N''-{boroxin-2,4,6- triyltris[[(1R)-3-methylbutane-1,1-diyl]imino(2-oxoethane-2,1-diyl)]}tris(2,5-dichlorobenzamide) was added. To this was added approximately 90 g of the Stock Formulation Vehicle, and the resulting mixture was stirred for 48 hours protected from light. The final pH was pH 5.12. The final weight of the resulting solution was adjusted to 100 g (assuming density of 1 g/mL) with Stock Formulation Vehicle and filtered through a 0.2 µm PES membrane filter unit and stored protected from light at a temperature between about 2° C. and about 8° C.

Formulation D: The Formulation Stock was diluted to concentrations of 0.05 mg/mL and 0.1 mg/mL with Stock Formulation Vehicle prior to use.

Formulation E: The Formulation Stock was diluted to concentrations of 0.05 mg/mL and 0.1 mg/mL with a 0.9% sodium chloride solution prior to use.

Example 20

20S Proteasome Assay

To 1 µL of test compound dissolved in DMSO in a 384-well black microtiter plate is added 25 µL of assay buffer at 37° C. containing human PA28 activator (Boston Biochem, 12 nM final) with Ac-WLA-AMC (β5 selective substrate) (15 µM final), followed by 25 µL of assay buffer at 37° C. containing human 20S proteasome (Boston Biochem, 0.25 nM final). Assay buffer is composed of 20 mM HEPES, 0.5 mM EDTA and 0.01% BSA, pH7.4. The reaction is followed on a BMG Galaxy plate reader (37° C., excitation 380 nm, emission 460 nm, gain 20). Percent inhibition is calculated relative to 0% inhibition (DMSO) and 100% inhibition (10 µM bortezomib) controls.

Example 21

Antiproliferation Assay

HCT-116 (1000) or other tumor cells in 100 µL of appropriate cell culture medium (McCoy's 5A for HCT-116, Invitrogen) supplemented with 10% fetal bovine serum (Invitrogen) are seeded in wells of a 96-well cell culture plate and incubated overnight at 37° C. Test compounds are added to the wells and the plates are incubated for 96 hours at 37° C. MTT or WST reagent (10 µL, Roche) are added to each well and incubated for 4 hours at 37° C. as described by the manufacturer. For MTT the metabolized dye is solubilized overnight according to manufacturer's instructions (Roche). The optical density for each well is read at 595 nm (primary) and 690 nm (reference) for the MTT and 450 nm for the WST using a spectrophotometer (Molecular Devices). For the MTT the reference optical density values are subtracted from the values of the primary wavelength. Percent inhibition is calculated using the values from a DMSO control set to 100%.

Example 22

In Vivo Tumor Efficacy Model

Freshly dissociated HCT-116 ($2-5\times10^6$) or other tumor cells in 100 µL of RPMI-1640 media (Sigma-Aldrich) are aseptically injected into the subcutaneous space in the right dorsal flank of female CD-1 nude mice (age 5-8 weeks, Charles River) using a 1 mL 26 ⅜-ga needle (Becton Dickinson Ref#309625). Alternatively, some xenograft models require the serial passaging of tumor fragments. In these cases, small fragments of tumor tissue (approximately 1 $mm^3$) are implanted subcutaneously in the right dorsal flank of anesthetized (3-5% isoflouraneoxygen mixture) C.B-17/SCID mice (age 5-8 weeks, Charles River) via a 13-ga trocar (Popper & Sons 7927). Beginning at day 7 after inoculation tumors are measured twice weekly using a vernier caliper. Tumor volumes are calculated using standard procedures ($0.5\times(length\times width^2)$). When the tumors reach a volume of approximately 200 $mm^3$ mice are randomized into treatment groups and begin receiving drug treatment. Dosing and schedules are determined for each experiment based on previous results obtained from pharmacokinetic/pharmacodynamic and maximum tolerated dose studies. The control group will receive vehicle without any drug. Typically, test compound (100-200 µL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 $mm^3$.

Example 23

Synthesis of N—((S)-1-((R)-3-methyl-1-(4-oxo-4H-benzo[d][1,3,2]dioxaborinin-2-yl)butylamino)-1-oxo-3-phenylpropan-2-yl)pyrazine-2-carboxamide (I-19)

A mixture of N,N',N"-(boroxin-2,4,6-triyltris{[(1R)-3-methylbutane-1,1-diyl]imino[(2S)-1-oxo-3-phenylpropane-1,2-diyl]})tripyrazine-2-carboxamide (0.250 g, 0.228 mmol) and salicyclic acid (269.6 mg, 0.68 mmol) were mixed in EtOAc (10 mL). The mixture was heated to form a solution. The solution was cooled uncontrolled until the internal temperature was about 25° C. Heptane (16 mL) was added. White solid precipitated out and the resultant slurry was agitated at ambient temperature for 3 h. The slurry was filtered to collect solid N-4S)-1-((R)-3-methyl-1-(4-oxo-4H-benzo[d][1,3,2]dioxaborinin-2-yl)butylamino)-1-oxo-3-phenylpropan-2-yl) pyrazine-2-carboxamide (0.249 g, 75%). MS (m/z) in $CH_3CN$: [M+H] calculated for $C_{26}H_{28}BN_4O_5$, 487.2153. found, 487.3.

Example 24

Synthesis of 2-((S)-2-((R)-3-methyl-1-((S)-3-phenyl-2-(pyrazine-2-carboxamido)propanamido)butyl)-5-oxo-1,3,2-dioxaborolan-4-yl)acetic acid (I-20)

A mixture of N,N',N"-(boroxin-2,4,6-triyltris{[(1R)-3-methylbutane-1,1-diyl]imino[(2S)-1-oxo-3-phenylpropane-1,2-diyl]})tripyrazine-2-carboxamide (0.500 g, 0.455 mmol) and L-malic acid (213.6 mg, 0.55 mmol) were mixed in THF (5 mL). The mixture was heated to form a solution. The solution was cooled uncontrolled until the internal temperature was about 25° C. White solid precipitated out and the resultant slurry was agitated at ambient temperature for 1 h. The slurry was filtered to collect solid 2-((S)-2-((R)-3-methyl-1-((S)-3-phenyl-2-(pyrazine-2-carboxamido)propanamido)butyl)-5-oxo-1,3,2-dioxaborolan-4-yl)acetic acid (0.625 g, 95%). MS (m/z) in $CH_3CN$: [M+H] calculated for $C_{23}H_{28}BN_4O_7$, 483.2051. found, 483.2.

Example 25

Synthesis of 2-((R)-2-((R)-3-methyl-1-((S)-3-phenyl-2-(pyrazine-2-carboxamido)propanamido)butyl)-5-oxo-1,3,2-dioxaborolan-4-yl)acetic acid (I-21)

A mixture of N,N',N"-(boroxin-2,4,6-triyltris{[(1R)-3-methylbutane-1,1-diyl]imino[(2S)-1-oxo-3-phenylpropane- 1,2-diyl]})tripyrazine-2-carboxamide (0.305 g, 0.278 mmol) and D-malic acid (130.3 mg, 0.33 mmol) were mixed in acetone (3 mL). The mixture was heated to form a solution. The solution was cooled uncontrolled until the internal temperature was about 25° C. White solid precipitated out and the resultant slurry was agitated at ambient temperature for 3 h. The slurry was filtered to collect solid 2-((R)-2((R)-3-methyl-1-((S)-3-phenyl-2-(pyrazine-2-carboxamido)propanamido) butyl)-5-oxo-1,3,2-dioxaborolan-4-yl)acetic acid (0.410 g, 100%). [M+H] calculated for $C_{23}H_{28}BN_4O_7$, 483.2051. found, 483.2.

Example 26

Synthesis of (R)-2-hydroxy-2-((R)-2-((R)-3-methyl-1-((S)-3-phenyl-2-(pyrazine-2-carboxamido)propanamido)butyl)-5-oxo-1,3,2-dioxaborolan-4-yl) acetic acid (I-22)

A mixture of N,N',N''-(boroxin-2,4,6-triyltris {[(1R)-3-methylbutane-1,1-diyl]imino[2S)-1-oxo-3-phenylpropane-1,2-diyl]})tripyrazine-2-carboxamide (0.270 g, 0.246 mmol) and L-tartaric acid (149.5 mg, 0.33 mmol) were mixed in acetone (3 mL). The mixture was heated to form a solution. The solution was cooled uncontrolled until the internal temperature was about 25° C. Heptane (2.5 mL) was added. White solid precipitated out and the resultant slurry was agitated at ambient temperature for 1.5 h. The slurry was filtered to collect solid (R)-2-hydroxy-2-((R)-2-((R)-3-methyl-1-((S)-3-phenyl-2-(pyrazine-2-carboxamido)propanamido)butyl)-5-oxo-1,3,2-dioxaborolan-4-yl)acetic acid (0.388 g) which also contained a dimeric species. MS (m/z) in $CH_3CN$: [M+H] calculated for $C_{23}H_{28}BN_4O_8$, 499.2000. found, 499.2.

Example 27

Synthesis of (S)-2-hydroxy-2-((S)-2-((R)-3-methyl-1-((S)-3-phenyl-2-(pyrazine-2-carboxamido)propanamido)butyl)-5-oxo-1,3,2-dioxaborolan-4-yl) acetic acid (I-23)

A mixture of N,N',N''-(boroxin-2,4,6-triyltris{[(1R)-3-methylbutane-1,1-diyl]imino[(2S)-1-oxo-3-phenylpropane-1,2-diyl]})tripyrazine-2-carboxamide (0.180 g, 0.164 mmol) and D-tartaric acid (147.5 mg, 0.33 mmol) were mixed in acetone (4 mL). The mixture was heated to form a solution. The solution was cooled uncontrolled until the internal temperature was about 25° C. Heptane (8 mL) was added. The mixture was evaporated to yield (S)-2-hydroxy-2-((S)-2-((R)-3-methyl-1-((S)-3-phenyl-2-(pyrazine-2-carboxamido) propanamido)butyl)-5-oxo-1,3,2-dioxaborolan-4-yl)acetic acid (0.447 g) which also contained a dimeric species. MS (m/z) in $CH_3CN$: [M+H] calculated for $C_{23}H_{28}BN_4O_8$, 499.2000. found, 499.2.

Example 28

Pharmaceutical Composition 1

The composition of the capsule is shown in Table 7 below.

TABLE 7

| Capsule composition | | |
| --- | --- | --- |
| Component | Function | mg/Capsule |
| Compound of formula (I-1) Form 2 | | 0.29 |
| Microcrystalline cellulose (low moisture) | Filler | 89.71 |
| Total capsule content weight, mg | | 90.00 |
| Size 4 white opaque gelatin capsules | | |

Example 29

Pharmaceutical Composition 2

The composition of the capsule is shown in Table 8 below.

TABLE 8

| Capsule composition | | |
| --- | --- | --- |
| Component | Function | mg/Capsule |
| Compound of formula (I-1) Form 2 | | 0.29 |
| Silicified microcrystalline cellulose | Filler | 109.71 |
| Total capsule content weight, mg | | 110.00 |
| Size 4 white opaque gelatin capsules | | |

Example 30

Pharmaceutical Composition 3

The composition of the capsule is shown in Table 9 below.

TABLE 9

| Capsule composition | | |
| --- | --- | --- |
| Component | Function | mg/Capsule |
| Compound of formula (I-1) Form 2 | | 0.29 |
| Microcrystalline cellulose (low moisture) | Filler | 88.81 |
| Magnesium stearate | Lubricant | 0.90 |
| Total capsule content weight, mg | | 90.00 |
| Size 4 white opaque gelatin capsule | | |

Example 31

Pharmaceutical Composition 4

The composition of the capsule is shown in Table 10 below.

TABLE 10

| Capsule composition | | |
| --- | --- | --- |
| Component | Function | mg/Capsule |
| Compound of formula (I-1) Form 2 | | 0.29 |
| Microcrystalline cellulose | Filler | 78.91 |
| Magnesium stearate | Lubricant | 0.80 |
| Total capsule content weight, mg | | 80.00 |
| Size 4 white opaque gelatin capsule | | |

Example 32

Pharmaceutical Composition 5

The composition of the capsule is shown in Table 11 below.

TABLE 11

| Capsule composition | | |
| --- | --- | --- |
| Component | Function | mg/Capsule |
| Compound of formula (I-1) Form 2 | | 0.29 |
| Microcrystalline cellulose (low moisture) | Filler | 84.71 |
| Total capsule contents weight, mg | | 85.00 |
| Size 4 white opaque gelatin capsule | | |

Example 33

Pharmaceutical Composition 6

The composition of the capsule is shown in Table 12 below.

TABLE 12

| Capsule composition | | |
| --- | --- | --- |
| Component | Function | mg/Capsule |
| Compound of formula (I-1) Form 2 | | 0.72 |
| Microcrystalline cellulose (low moisture) | Filler | 119.28 |
| Total capsule content weight, mg | | 120.00 |
| Size 3 dark green gelatin capsule | | |

Example 34

Pharmaceutical Composition 7

The composition of the capsule is shown in Table 13 below.

TABLE 13

| Capsule composition | | |
| --- | --- | --- |
| Component | Function | mg/Capsule |
| Compound of formula (I-1) Form 2 | | 2.89 |
| Microcrystalline cellulose (low moisture) | Filler | 147.11 |
| Total capsule content weight, mg | | 150.00 |
| Size 2 Swedish orange gelatin capsule | | |

Example 35

Pharmaceutical Composition 8

The composition is shown in Table 14 below.

TABLE 14

| Batch composition | | | |
| --- | --- | --- | --- |
| Item Number | Component | g/Batch | mg/Capsule |
| 1 | Compound of formula (I-1) Form 2 | 7.06 | 0.30 |
| 2 | Microcrystalline cellulose, NF (Emcocel ® XLM90; low moisture) | 100 | 4.25 |
| 3 | Microcrystalline cellulose, NF (Emcocel ® XLM90; low moisture) | 192.9 | 8.20 |
| 4 | Microcrystalline cellulose, NF (Emcocel ® XLM90; low moisture) | 300 | 12.75 |
| 5 | Microcrystalline cellulose, NF (Emcocel ® XLM90; low moisture) | 500 | 21.25 |
| 6 | Microcrystalline cellulose, NF (Emcocel ® XLM90; low moisture) | 900 | 38.25 |
| | Total weight | 2000.0 | 85.00 |
| | Size 4 white opaque gelatin capsules | | |

The batch was prepared according to the following process:

1) Microcrystalline cellulose, NF (Emcocel® XLM90; low moisture) (Item #2) was screened through a 40 micron mesh screen.
2) The screened material from step 1) was added to the PK blender and was blended for 2 minutes.
3) Compound of formula (I-1) Form 2 that had been screened through a 60 micron mesh screen, was weighed out (Item #1).
4) The compound of formula (I-1) Form 2 from step 3), and the microcrystalline cellulose, NF (Emcocel® XLM90; low moisture) (Item #3) were combined in a polyethylene bag, and the polyethylene bag was shaken; then the contents of the polyethylene bag were passed through the same 40 micron screen as was used in step 1).
5) The material from step 4) was added to the PK blender and blended for 15 minutes.
6) Microcrystalline cellulose, NF (Emcocel® XLM90; low moisture) (Item #4) was screened through the same 40 micron mesh screen, transferred to the same polyethylene bag used in step 4) and shaken in the polyethylene bag.
7) The material from step 6) was added to the PK blender, which still contained the material from step 5) and blended for 10 minutes.
8) Microcrystalline cellulose, NF (Emcocel® XLM90; low moisture) (Item #5) was screened through the same 40 micron mesh screen, transferred to the same polyethylene bag used in steps 4) and 6), and shaken in the polyethylene bag.
9) The material from step 8) was added to the PK blender, which still contained the material from steps 5) and 7), and blended for 10 minutes.
10) Microcrystalline cellulose, NF (Emcocel® XLM90; low moisture) (Item #6) was screened through the same 40 micron mesh screen, transferred to the same polyethylene bag used in steps 4), 6), and 8), and shaken in the polyethylene bag.
11) The material from step 10) was added to the PK blender, which still contained the material from steps 5), 7), and 9), and blended for 10 minutes.
12) The material from the blender was encapsulated in size 4 white opaque gelatin capsules using the In-Cap system.
13) The capsules were de-dusted, and weight-sorted.

Example 36

Pharmaceutical Composition 9

The composition of the capsules is shown in Table 15 below.

TABLE 15

| Capsule composition | | |
| --- | --- | --- |
| Component | Function | mg/Capsule |
| Compound of formula (I-1) Form 2 | | 0.3 |
| Pregeletanized Starch (Starch 1500) | Filler | 122.825 |
| Talc | Flow-aid | 1.25 |
| Magnesium Stearate | Lubricant | 0.625 |
| Total capsule content weight, mg | | 125.00 |
| Size 4 white opaque gelatin capsule | | |

Example 37

Pharmaceutical Composition 10

The composition of the capsules is shown in Table 16 below.

TABLE 16

| Capsule composition | | |
| --- | --- | --- |
| Component | Function | mg/Capsule |
| Compound of formula (I-1) Form 2 | | 0.3 |
| Pregeletanized Starch (Starch 1500) | Filler | 124.7 |
| Total capsule content weight, mg | | 125.00 |
| Size 4 white opaque gelatin capsule | | |

Example 38

Pharmaceutical Composition 11

The composition of the capsule is shown in Table 17 below.

TABLE 17

| Capsule composition | | |
| --- | --- | --- |
| Component | Function | mg/Capsule |
| Compound of formula (I-1) Form 2 | | 0.3 |
| Microcrystalline cellulose (Emcocel ® XLM90; low moisture) | Filler | 124.7 |
| Talc | Flow-aid | 1.25 |
| Total capsule content weight, mg | | 125.00 |
| Size 4 white opaque gelatin capsule | | |

Example 39

Pharmaceutical Composition 12

The composition of the capsule is shown in Table 18 below.

TABLE 18

| Capsule composition | | |
| --- | --- | --- |
| Component | Function | mg/Capsule |
| Compound of formula (I-1) Form 2 | | 0.3 |
| Microcrystalline cellulose (Emcocel ® XLM90; low moisture) | Filler | 89.25 |
| Magnesium Stearate | Lubricant | 0.45 |
| Total capsule content weight, mg | | 90.00 |
| Size 4 white opaque gelatin capsule | | |

Example 40

Pharmaceutical Composition 13

The composition of the capsule is shown in Table 19 below.

TABLE 19

| Capsule composition | | |
| --- | --- | --- |
| Component | Function | mg/Capsule |
| Compound of formula (I-1) Form 2 | | 0.3 |
| Microcrystalline cellulose (Emcocel ® XLM90; low moisture) | Filler | 88.35 |
| Talc | Flow-aid | 0.9 |
| Magnesium Stearate | Lubricant | 0.45 |
| Total capsule content weight, mg | | 90.00 |
| Size 4 white opaque gelatin capsule | | |

Example 41

Pharmaceutical Composition 14

The composition of the capsule is shown in Table 20 below.

TABLE 20

| Capsule composition | | |
| --- | --- | --- |
| Component | Function | mg/Capsule |
| Compound of formula (I-1) Form 2 | | 0.3 |
| Microcrystalline cellulose (Emcocel ® XLM90; low moisture) | Filler | 51.15 |
| Talc | Flow-aid | 0.98 |
| Magnesium Stearate | Lubricant | 0.49 |
| Pregeletanized Starch (Starcap) | | 45.08 |
| Total capsule content weight, mg | | 98.00 |
| Size 4 white opaque gelatin capsule | | |

Example 42

Pharmaceutical Composition 15

The composition of the capsule is shown in Table 21 below.

TABLE 21

| Capsule composition | | |
| --- | --- | --- |
| Component | Function | mg/Capsule |
| Compound of formula (I-1) Form 2 | | 0.3 |
| Microcrystalline cellulose (Emcocel ® XLM90; low moisture) | Filler | 61.65 |

TABLE 21-continued

Capsule composition

| Component | Function | mg/Capsule |
|---|---|---|
| Talc | Flow-aid | 1.18 |
| Magnesium Stearate | Lubricant | 0.59 |
| Sodium Starch Glycolate (Explotab) | | 54.28 |
| Total capsule content weight, mg | | 118.00 |
| Size 4 white opaque gelatin capsule | | |

Example 43

Pharmaceutical Composition 16

The composition of the batch is shown in Table 22 below.

TABLE 22

Batch composition

| Item Number | Component | g/Batch | mg/Capsule |
|---|---|---|---|
| 1 | Compound of formula (I-1) Form 2 | 0.33 | 0.30 |
| 2 | Microcrystalline cellulose, NF (Emcocel ® XLM90; low moisture) | 5.00 | 4.50 |
| 3 | Microcrystalline cellulose, NF (Emcocel ® XLM90; low moisture) | 8.17 | 7.35 |
| 4 | Microcrystalline cellulose, NF (Emcocel ® XLM90; low moisture) | 14.00 | 12.60 |
| 5 | Microcrystalline cellulose, NF (Emcocel ® XLM90; low moisture) | 25.00 | 22.50 |
| 6 | Microcrystalline cellulose, NF (Emcocel ® XLM90; low moisture) | 44.00 | 39.60 |
| 7 | Talc | 1.00 | 0.90 |
| 8 | Sodium Citrate | 2.00 | 1.80 |
| 9 | Magnesium Stearate | 0.50 | 0.45 |
| | Total weight | 100.00 | 90.00 |
| | Size 4 white opaque gelatin capsules | | |

The batch was prepared according to the following process:

1) Microcrystalline cellulose, NF (Emcocel® XLM90; low moisture) (Item #2) was screened through a 40 micron mesh screen.
2) The screened material from step 1) was added to the PK blender and was blended for 2 minutes.
3) Compound of formula (I-1) Form 2 that had been screened through a 60 micron mesh screen, was weighed out (Item #1).
4) The compound of formula (I-1) Form 2 from step 3), and the microcrystalline cellulose, NF (Emcocel® XLM90; low moisture) (Item #3) were combined in a polyethylene bag, and the polyethylene bag was shaken; then the contents of the polyethylene bag were passed through the same 40 micron screen as was used in step 1).
5) The material from step 4) was added to the PK blender and blended for 15 minutes.
6) Microcrystalline cellulose, NF (Emcocel® XLM90; low moisture) (Item #4) was screened through the same 40 micron mesh screen, transferred to the same polyethylene bag used in step 4) and shaken in the polyethylene bag.
7) Talc (Item #7), and Sodium Citrate (Item #8) were screened through the same 40 micron mesh screen.
8) The materials from step 6) and 7) were added to the PK blender, which still contained the material from step 5) and blended for 10 minutes.
9) Microcrystalline cellulose, NF (Emcocel® XLM90; low moisture) (Item #5) was screened through the same 40 micron mesh screen, transferred to the same polyethylene bag used in steps 4) and 6), and shaken in the polyethylene bag.
10) The material from step 9) was added to the PK blender, which still contained the material from steps 5) and 8), and blended for 10 minutes.
11) Microcrystalline cellulose, NF (Emcocel® XLM90; low moisture) (Item #6) was screened through the same 40 micron mesh screen, transferred to the same polyethylene bag used in steps 4), 6), and 9), and shaken in the polyethylene bag.
12) The material from step 11) was added to the PK blender, which still contained the material from steps 5), 8), and 10), and blended for 10 minutes.
13) Magnesium Stearate (Item #9) was screened through the same 40 micron mesh screen.
14) The material from step 13) was added to the PK blender, which still contained the material from steps 5), 8), 10), and 12) and blended for 5 minutes.
15) The material from the blender was encapsulated in size 4 white opaque gelatin capsules using the Profill system.
16) The capsules were de-dusted, and weight-sorted.

Example 44

Pharmaceutical Composition 17

The composition of the batch is shown in Table 23 below.

TABLE 23

Batch composition

| Item Number | Component | g/Batch | mg/Capsule |
|---|---|---|---|
| 1 | Compound of formula (I-1) Form 2 | 7.06 | 0.30 |
| 2 | Microcrystalline cellulose, NF (Emcocel ® XLM90; low moisture) | 4.94 | 0.21 |
| 3 | Microcrystalline cellulose, NF (Emcocel ® XLM90; low moisture) | 25.00 | 1.06 |
| 4 | Microcrystalline cellulose, NF (Emcocel ® XLM90; low moisture) | 53.00 | 2.25 |
| 5 | Talc | 10.00 | 0.43 |
| 6 | Microcrystalline cellulose, NF (Emcocel ® XLM90; low moisture) | 90 | 3.83 |
| 7 | Talc | 30 | 1.28 |
| 8 | Microcrystalline cellulose, NF (Emcocel ® XLM90; low moisture) | 170 | 7.23 |
| 9 | Microcrystalline cellulose, NF (Emcocel ® XLM90; low moisture) | 300 | 12.75 |
| 10 | Microcrystalline cellulose, NF (Emcocel ® XLM90; low moisture) | 500 | 21.25 |
| 11 | Microcrystalline cellulose, NF (Emcocel ® XLM90; low moisture) | 800 | 34 |
| 12 | Magnesium Stearate | 10 | 0.43 |
| | Total weight | 2000 | 85 |
| | Size 4 white opaque gelatin capsules | | |

The batch was prepared according to the following process:

1) Microcrystalline cellulose, NF (Emcocel® XLM90; low moisture) (Item #2) was screened through a 40 micron mesh screen.
2) The screened material from step 1) was added to the small PK blender and blended for 2 minutes.
3) Compound of formula (I-1) Form 2 that had been screened through a 60 micron mesh screen was weighed out (Item #1).
4) The compound of formula (I-1) Form 2 from step 3), and the microcrystalline cellulose, NF (Emcocel® XLM90; low moisture) (Item #3) were combined, and then passed through the same 40 micron screen as was used in step 1).
5) The material from step 4) was added to the small PK blender and blended for 30 minutes.
6) Microcrystalline cellulose, NF (Emcocel® XLM90; low moisture) (Item #4) and Talc (Item #5) were screened through the same 40 micron mesh screen.
7) The material from step 6) was added to the small PK blender, which still contained the material from step 5) and blended for 15 minutes.
8) Microcrystalline cellulose, NF (Emcocel® XLM90; low moisture) (Item #6) was screened through the same 40 micron mesh screen, transferred to a second larger PK blender, and blended for 2 minutes.
9) The contents of the small PK blender from steps 5) and 7) were emptied into a polyethylene bag, and then transferred to the larger PK blender from step 8).
10) Talc (Item #7) and Microcrystalline cellulose, NF (Emcocel® XLM90; low moisture) (Item #8) were screened through the same 40 micron mesh screen.
11) Half the material from step 10) was added to the small PK blender from steps 5) and 7), blended for 3 minutes, transferred to the same polyethylene bag used in step 9), and shaken in the polyethylene bag.
12) The material from step 11) was added to the larger PK blender, which still contained the material from steps 8) and 9).
13) The second half of material from step 10) was added to the small PK blender from steps 5) and 7), and 11), blended for 3 minutes, transferred to the same polyethylene bag used in steps 9) and 11), and shaken in the polyethylene bag.
14) The material from step 13) was added to the larger PK blender, which still contained the material from steps 8), 9), and 12), and blended for 10 minutes.
15) Microcrystalline cellulose, NF (Emcocel® XLM90; low moisture) (Item #9) was screened through the same 40 micron mesh screen, transferred to the same polyethylene bag used in steps 9), 11), and 13), and shaken in the polyethylene bag.
16) The material from step 15) was added to the same larger PK blender, which still contained material from steps 8), 9), 12), and 14), and blended for 10 minutes.
17) Microcrystalline cellulose, NF (Emcocel® XLM90; low moisture) (Item #10) was screened through the same 40 micron mesh screen.
18) The material from step 17) was added to the same larger PK blender, which still contained material from steps 8), 9), 12), 14), and 16), and blended for 10 minutes.
19) Microcrystalline cellulose, NF (Emcocel® XLM90; low moisture) (Item #11) was screened through the same 40 micron mesh screen.
20) The material from step 19) was added to the same larger PK blender, which still contained material from steps 8), 9), 12), 14), 16), and 18), and blended for 10 minutes.
21) Magnesium Stearate (Item #12) was screened through the same 40 micron mesh screen.
22) The material from step 21) was added to the same larger PK blender, which still contained material from steps 8), 9), 12), 14), 16), 18), and 20), and blended for 5 minutes.
23) The material from the blender was encapsulated in size 4 white opaque gelatin capsules using the Incap system.
24) The capsules were de-dusted, and weight-sorted.

Example 45

Pharmaceutical Composition 18

The composition of the batch is shown in Table 24 below.

TABLE 24

Batch composition

| Item Number | Component | g/Batch | mg/Capsule |
|---|---|---|---|
| 1 | Compound of formula (I-1) Form 2 | 3.53 | 0.30 |
| 2 | Microcrystalline cellulose, NF (Emcocel ® XLM90; low moisture) | 496.5 | 4.50 |
| 3 | Microcrystalline cellulose, NF (Emcocel ® XLM90; low moisture) | 500 | 7.35 |
| | Total weight | 1000 | 85 |
| | Size 4 white opaque gelatin capsules | | |

The batch is prepared according to the following process:
1) Microcrystalline cellulose, NF (Emcocel® XLM90; low moisture) (Item #2) is screened through a 40 micron mesh screen and added to a high shear mixer.
2) Compound of formula (I-1) Form 2 is screened through a 60 micron mesh screen and weighed out (Item #1) and added to the same high shear mixer from step 1).
3) Microcrystalline cellulose, NF (Emcocel® XLM90; low moisture) (Item #3) is screened through the same 40 micron mesh screen, and added to the same high shear mixer from steps 1) and 2).
4) The high shear mixer from steps 1), 2), and 3) is run for 4 minutes.
5) The material from the high shear mixer is encapsulated in size 4 white opaque gelatin capsules using the Incap system.
6) The capsules are de-dusted, and weight-sorted.

Example 46

Lyophilized Powder 1

In a clean container, a solution of 40% tert-butyl alcohol 60% water for injection was prepared by warming the required amount of tert-butyl alcohol to 35° C. and adding water for injection. The solution was cooled to 15-30° C. A portion of the required amount (60% of the total batch) of tert-butyl alcohol/water solution was added to a pre-compounding container. Approximately 40% of the solution was reserved for use in rinsing. Citric acid (30% of the batch amount) was added to the pre-compounding container with stirring. The container was rinsed with the reserved tert-butyl alcohol/water solution, and the rinses were added to the pre-compounding container. The mixture was stirred until the citric acid was completely dissolved. Sodium citrate (30% of the batch amount) was added to the pre-compounding container with stirring. The container was rinsed with the reserved tert-butyl alcohol/water solution, and the rinses were added to the pre-compounding container. The mixture was stirred until the sodium citrate was completely dissolved. N-(2-pyrazine)carbonyl-L-phenyl-L-leucine boronic acid (VIII-15) was added to the pre-compounding container with stirring. The container was rinsed with the reserved tert-butyl alcohol/water solution, and the rinses were added to the pre-compounding container. The mixture was stirred until the boronic acid was completely dissolved. The citric acid, sodium citrate, and boronic acid mixture from the pre-compounding container was transferred to the main compounding vessel. The pre-compounding container was rinsed with water for injection and the rinses were added to the main compounding vessel. Citric acid (70% of the batch amount) was added to the main vessel with stirring. The container was rinsed with the water, and the rinses were added to the main vessel. The mixture was stirred until the citric acid was completely dissolved. Sodium citrate (70% of the batch amount) was added to the main vessel with stirring. The container was rinsed with water, and the rinses were added to the pre-compounding container. The mixture was stirred until the sodium citrate was completely dissolved. Glycine was added to the main vessel and the residual glycine was rinsed with water, and the rinses were added to the main vessel. The mixture was stirred until the glycine was completely dissolved. Sufficient water was added to reduce the total alcohol content to 4.7% v/v. The mixture was filtered through a 0.22 μm filter. Aliquots of the filtered solution were placed into vials. The vials were sealed with lyophilization stoppers and were placed on lyophilizer chamber shelves maintained at 20° C. The lyophilization chamber shelves were cooled to −45° C. using the appropriate ramp rate and held at that temperature for 200 minutes. The shelf was warmed to −20° C. using an appropriate ramp rate and maintained at that temperature for 480 minutes. The shelf was re-cooled to −45° C. using an appropriate ramp rate and maintained at that temperature. After 200 minutes, the lyophililization chamber was evacuated, and the chamber pressure was adjusted to 150 microns with nitrogen. The chamber shelves were warmed up to −25° C. using an appropriate ramp rate, and held at that temperature for 3000 minutes. After each of the product thermocouples read −25° C. or warmer, the shelf was warmed to 27° C. and maintained at that temperature for 600 minutes. At the end of the terminal drying phase, the chamber pressure was restored using nitrogen, and vials were sealed and removed. Pre lyophilized solution contained: 52 mM citrate, 3% glycine, 4.7% tert-butyl alcohol (as shown in Table 25 below).

TABLE 25

Batch composition

| No. | Component | Amount/mL | mM | Batch | Amount per vial |
|---|---|---|---|---|---|
| 1. | Compound (VIII-15) | 0.001 g | 2.6 | 0.300 g | 3.5 mg |
| 2. | Citric Acid Monohydrate, USP/EP | 0.00382 g | 18.2 | 1.147 g | 13.37 mg |
| 3. | Sodium Citrate Dihydrate, USP/EP | 0.00994 g | 33.8 | 2.982 g | 34.79 mg |
| 4. | Glycine, USP/EP | 0.03 g | 399.6 | 9.0 g | 105 mg |
| 5. | Tert-butyl alcohol, ACS grade | n/a | n/a | 14.1 mL | 0.1645 mL |
| 6. | Water for Injection, USP/EP | n/a | n/a | Fill to batch volume | n/a |
| 7. | Total volume | n/a | n/a | 300 mL | 3.5 mL |
| 8. | Final measured pH | n/a | n/a | 5.08 | n/a |

Example 47

Lyophilized Powder 2

Prepared as described in Example 46. Pre-lyophilized solution contained: 52 mM citrate; 3% glycine; and 4.7% tert-butyl alcohol (as shown in Table 26 below).

TABLE 26

Batch composition

| No. | Component | Amount/mL | mM | Batch | Amount per vial |
|---|---|---|---|---|---|
| 1. | Compound (VIII-15) | 0.001 g | 2.6 | 0.300 g | 3.5 mg |
| 2. | Citric Acid Monohydrate, USP/EP | 0.00168 g | 8.0 | 0.504 g | 5.88 mg |
| 3. | Sodium Citrate Dihydrate, USP/EP | 0.0129 g | 44.0 | 3.882 g | 45.15 mg |
| 4. | Glycine, USP/EP | 0.03 g | 399.6 | 9.0 g | 105 mg |
| 5. | Tert-butyl alcohol, ACS grade | n/a | n/a | 14.1 mL | 0.1645 mL |
| 6. | Water for Injection, USP/EP | n/a | n/a | Fill to batch volume | n/a |
| 7. | Total volume | n/a | n/a | 300 mL | 3.5 mL |
| 8. | Final measured pH | n/a | n/a | 5.84 | n/a |

Example 48

Lyophilized Powder 3

The formulation was prepared as described in Example 46, except that the lyophilization cycle was modified. The vials were sealed with lyophilization stoppers and placed on lyophilizer chamber shelves maintained at 20° C. The lyophilization chamber shelves were cooled to −45° C. using the appropriate ramp rate and held at that temperature for 200 minutes. The shelf was warmed to −20° C. using an appropriate ramp rate and maintained at that temperature for 480 minutes. The shelf was re-cooled to −45° C. using an appropriate ramp rate and maintained at that temperature. After 200 minutes, the lyophilization chamber was evacuated, and the chamber pressure was adjusted to 150 microns with nitrogen. The chamber shelves was warmed up to −15° C. using an appropriate ramp rate, and held at that temperature for 2700 minutes. After each of the product thermocouples read −15° C. or warmer, the shelf was warmed to 37° C. and maintained at that temperature for 300 minutes. At the end of the terminal drying phase, the chamber pressure was restored using nitrogen, and the vials were sealed and removed. Pre-lyophilized solution contained: 52 mM citrate; 3% glycine; and 4.7% tert-butyl alcohol (as shown in Table 27 below).

TABLE 27

Batch composition

| No. | Component | Amount/mL | mM | Batch | Amount per vial |
|---|---|---|---|---|---|
| 1. | Compound (VIII-15) | 0.001 g | 2.6 | 1.0 g | 3.5 mg |
| 2. | Citric Acid Monohydrate, USP/EP | 0.00382 g | 18.2 | 3.82 g | 13.37 mg |
| 3. | Sodium Citrate Dihydrate, USP/EP | 0.00994 g | 33.8 | 9.94 g | 34.79 mg |
| 4. | Glycine, USP/EP | 0.03 g | 399.6 | 30.0 g | 105 mg |
| 5. | Tert-butyl alcohol, ACS grade | n/a | n/a | 47.0 mL | 0.1645 mL |
| 6. | Water for Injection, USP/EP | n/a | n/a | Fill to batch volume | n/a |
| 7. | Total volume | n/a | n/a | 1000 mL | 3.5 mL |
| 8. | Final measured pH | n/a | n/a | 5.05 | n/a |

Example 49

Lyophilized Powder 4

A clean vessel was charged with water for injection. Citric acid and sodium citrate were added and stirred until dissolved. To this solution, N-(2-pyrazine)carbonyl-L-phenyl-L-leucine boronic acid (VIII-15) was added and stirred until dissolved. Glycine was added to the vessel and the residual glycine was rinsed with water, and the rinses were added to the main vessel. The mixture was stirred until the glycine was completely dissolved. Sufficient water was added to batch volume. The mixture was filtered through a 0.22 μm filter. Aliquots of the filtered solution were placed into vials. The vials were sealed with lyophilization stoppers and were placed on lyophilizer chamber shelves maintained at 20° C. The lyophilization chamber shelves were cooled to −45° C. using the appropriate ramp rate and held at that temperature for 200 minutes. The shelf was warmed to −20° C. using an appropriate ramp rate and maintained at that temperature for 480 minutes. The shelf was re-cooled to −45° C. using an appropriate ramp rate and maintained at that temperature. After 200 minutes, the lyophilization chamber was evacuated with and the chamber pressure was adjusted to 150 microns with nitrogen. The chamber shelves were warmed up to −25° C. using an appropriate ramp rate, and held at that temperature for 3000 minutes. After each of the product thermocouples read −25° C. or warmer, the shelf was warmed to 27° C. and maintained at that temperature for 600 minutes. At the end of the terminal drying phase, the chamber pressure was restored using nitrogen, and vials were sealed and removed. Pre-lyophilized solution contained: 52 mM citrate; and 3% glycine (as shown in Table 28 below).

TABLE 28

Batch composition

| | Component | Amount/mL | mM | Batch | Amount per vial |
|---|---|---|---|---|---|
| 1. | Compound (VIII-15) | 0.001 g | 2.6 | 0.30 g | 3.5 mg |
| 2. | Citric Acid Monohydrate, USP/EP | 0.004097 g | 19.5 | 1.229 g | 14.34 mg |
| 3. | Sodium Citrate Dihydrate, USP/EP | 0.009557 g | 32.5 | 2.867 g | 33.45 mg |
| 4. | Glycine, USP/EP | 0.03 g | 399.6 | 9.0 g | 105 mg |
| 5. | Water for Injection, USP/EP | n/a | n/a | Fill to batch volume | n/a |
| 6. | Total volume | n/a | n/a | 300 mL | 3.5 mL |
| 7. | Final measured pH | n/a | n/a | 4.90 | n/a |

Example 50

Lyophilized Powder 5

Prepared as described in Example 49. Pre-lyophilized solution contained: 52 mM citrate; and 3% glycine (as shown in Table 29 below). In this example, the pH of the pre-lyophilized solution was adjusted to the final measured pH by the addition of 2N HCl.

TABLE 29

Batch composition

| No. | Component | Amount/mL | mM | Batch | Amount per vial |
|---|---|---|---|---|---|
| 1. | Compound (VIII-15) | 0.001 g | 2.6 | 0.30 g | 3.5 mg |
| 2. | Citric Acid Monohydrate, USP/EP | 0.00168 g | 8.0 | 0.504 g | 5.88 mg |
| 3. | Sodium Citrate Dihydrate, USP/EP | 0.01294 g | 44.0 | 3.882 g | 45.29 mg |
| 4. | Glycine, USP/EP | 0.03 g | 399.6 | 9.0 g | 105 mg |
| 5. | Water for Injection, USP/EP | n/a | n/a | Fill to batch volume | n/a |
| 6. | Total batch volume | n/a | n/a | 300 mL | 3.5 mL |
| 7. | Final measured pH | n/a | n/a | 5.84 | n/a |

Example 50

Lyophilized Powder 6

A clean vessel is charged with water for injection. Citric acid and sodium citrate are added and stirred until dissolved. To this solution, 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) is added and stirred until dissolved. Glycine is added to the vessel and the residual glycine is rinsed with water, and the rinses are added to the main vessel. The mixture is stirred until the glycine is completely dissolved. Sufficient water is added to batch volume. The mixture is filtered through a 0.22 μm filter. Aliquots of the filtered solution are placed into sterilized vials. The vials are sealed with lyophilization stoppers and are placed on lyophilizer chamber shelves maintained at 20° C. The lyophilization chamber shelves are cooled to −45° C. using an appropriate ramp rate, and then are held at that temperature for 200 minutes. The shelf is warmed to −20° C. using an appropriate ramp rate and then is maintained at that temperature for 480 minutes. The shelf is re-cooled to −45° C. using an appropriate ramp rate and is maintained at that temperature. After 200 minutes, the lyophilization chamber is evacuated, and the chamber pressure is adjusted to 150 microns with nitrogen. The chamber shelves are warmed up to −25° C. using an appropriate ramp rate, and held at that temperature for 3000 minutes. After each of the product thermocouples reads −25° C. or warmer, the shelf is warmed to 27° C. and is maintained at that temperature for 600 minutes. At the end of the terminal drying phase, the chamber pressure is restored using nitrogen, and vials are sealed and removed. The composition of the pre-lyophilized solution is 55 mM citrate; and 3% glycine (as shown in Table 30 below).

TABLE 30

| | | Batch composition | | | |
|---|---|---|---|---|---|
| No. | Component | Amount/mL | mM | Batch | Amount per vial |
| 1. | Compound (I-1) [expressed as amount of compound (VIII-1)] | 0.001 g | 2.75 | 0.50 g | 3.5 mg |
| 2. | Citric Acid Monohydrate, USP/EP | 0.0012 g | 5.5 | 0.578 g | 4.2 mg |
| 3. | Sodium Citrate Dihydrate, USP/EP | 0.0147 g | 49.5 | 7.279 g | 51.45 mg |
| 4. | Glycine, USP/EP | 0.03 g | 399.6 | 15.0 g | 105 mg |
| 5. | Water for Injection, USP/EP | n/a | n/a | Fill to batch volume | n/a |
| 6. | Total volume | n/a | n/a | 500 mL | 3.5 mL |

Example 51

Reconstitution of Lyophilized Powders

The lyophilized powders (e.g. as prepared in Examples 46-50) are analyzed using XRPD, DSC, gas chromatography, and Karl Fisher for cake structure, cake stability, residual solvent, and residual moisture, respectively. The lyophilized powders are reconstituted with the appropriate amount of sterile water for injection or with sterile 0.9% sodium chloride solution for injection. The reconstituted solutions are analyzed using HPLC, and NMR, for purity, and percentage ester.

Example 52

Preparation of formulation of 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2 for parenteral or oral administration A vessel was charged with water and citric acid monohydrate and sodium citrate dihydrate were added and stirred until dissolved. To this solution, 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid (I-1) Form 2 was added, and the mixture was stirred until a solution was obtained. To this solution, sodium chloride was added and stirred until dissolved. Sufficient water was added to batch volume and the solution was filtered through a 0.2 μm PES membrane. Aliquots of the filtered solution were placed into vials. The vials were sealed with stoppers and stored at −20° C. The batch and vial composition is as described below in Table 31.

Example 53

Analytical Test Method 1

Reversed-phase HPLC using a C8 column at 25° C. with ultraviolet (UV) detection at 225 nm.

Mobile phase: The gradient system starts at 85% mobile phase A (0.01% trifluoroacetic acid in water) and 15% mobile phase B (0.01% trifluoroacetic acid in acetonitrile) and ends at 75% mobile phase B after 40 minutes.

The test sample is prepared by dissolving the content of the capsules in diluent which is 15:85 (v/v) acetonitrile:20 mM citrate buffer. Under these aqueous conditions, the compound of formula (I-1) completely hydrolyzes the citrate ester portion of the molecule to give the compound of formula (VIII-1) in a 1:1 molecular ratio. The presence of the compound of formula in the test sample is confirmed by comparison of the sample retention time to that of the reference standard. The amount of the compound of formula (VIII-1) present in a sample is calculated from the area under the peak, on a weight-to-weight comparison including molecular weight conversion, with the area under the peak of the reference standard. The reference standard employed is a known amount of the compound of formula (I-1), of known purity, which is prepared under the same hydrolyzing conditions as the test sample. The limit of quantitation for the method is 0.05% and the calculated limit of detection is 0.02%.

Example 54

Analytical Test Method 2

Normal-phase HPLC using isocratic elution with a mobile phase of 40/60/0.1 (v/v/v) THF/n-Hexane/TFA on a cyano HPLC column at 25° C. for 8 minutes, with UV detection at 230 nm.

TABLE 31

| | | Batch composition | | | |
|---|---|---|---|---|---|
| No. | Component | Amount/mL | mM | Batch | Amount per vial |
| 1. | Compound (I-1) [expressed as amount of compound (VIII-1)] | 0.001 g | 2.75 | 20 g | 3.3 mg |
| 2. | Citric Acid Monohydrate, USP/EP | 0.0012 g | 5.5 | 23.198 g | 3.282 mg |
| 3. | Sodium Citrate Dihydrate, USP/EP | 0.0147 g | 49.5 | 291.183 g | 48.05 mg |
| 4. | Sodium Chloride, USP/EP | 0.0045 g | 77 | 89.991 g | 14.85 mg |
| 5. | Water for Injection, USP/EP | n/a | n/a | Fill to batch volume | n/a |
| 6. | Total volume | n/a | n/a | 20 L | 3.3 mL |
| 7. | Final measured pH | n/a | n/a | 5.72 | n/a |

The test sample is prepared by dissolving the content of the capsules in 40/60 (v/v) THF/n-Hexane. Under these conditions, the compound of formula (I-1) is not hydrolyzed to the compound of formula (VIII-1). The amount of the compound of formula (VIII-1) present in the test sample is calculated from the area under the peak, on a weight to weight comparison, with the area under the peak of the reference standard. The reference standard employed is a known amount of the compound of formula (VIII-1), of known purity, which is prepared under the same conditions as the test sample. The limit of quantitation for detection of the compound of formula (I-1) is 0.2%.

To calculate the amount of compound of formula (I-1) present in a test sample, both Analytical Test Method 1 and Analytical Test Method 2 are used. Analytical Test Method 1 is used to calculate the amount on a weight basis of the compound of formula (VIII-1) that is present in a test sample, containing the compound of formula (I-1). Analytical Test Method 2 is also used to calculate the amount of the compound of formula (VIII-1) present in the sample of the compound of formula (I-1) obtained without induced hydrolysis.

The amount of the compound of formula (VIII-1) obtained from Analytical Test Method 1 minus the amount of the compound of formula (VIII-1) obtained from Analytical Test Method 2 gives the measured amount of the compound of formula (VIII-1) that is produced by the induced hydrolysis of the compound of formula (I-1) present in the test sample. Based on a 1:1 molecular ratio, a molecular weight calculation gives the amount of the compound of formula (I-1) present in the test sample.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A process for generating a compound of Formula (II)

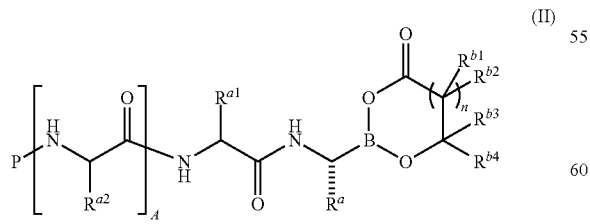

(II)

or a pharmaceutically acceptable salt thereof, wherein
A is 0, 1, or 2;
P is $R^c$—C(O)—; $R^c$ is $R^D$; $R^D$ is substituted or unsubstituted mono- or bicyclic ring system selected from the group consisting of phenyl, pyridinyl, pyrimidinyl, naphthyl, benzimidazolyl, quinolinyl, isoquinolinyl, quinoxalinyl, tetrahydroquinolinyl, tetrahydroisoquinolinyl, tetrahydroquinoxalinyl, and dihydrobenzoxazinyl;

$R^a$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=$NR^4$)NH—Y, —$(CH_2)_m$—$CH_2$—CON$(R^4)_2$, —$(CH_2)_m$—$CH_2$—N$(R^4)$CON$(R^4)_2$, —$(CH_2)_m$—CH$(R^6)$N$(R^4)_2$, —$(CH_2)_m$—CH$(R^{5a})$—$OR^{5b}$, or —$(CH_2)_m$—CH$(R^5)$—$SR^5$;

$R^{a1}$ is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=$NR^4$)NH—Y, —$(CH_2)_m$—$CH_2$—CON$(R^4)_2$, —$(CH_2)_m$—$CH_2$—N$(R^4)$CON$(R^4)_2$, —$(CH_2)_m$—CH$(R^6)$N$(R^4)_2$, —$(CH_2)_m$—CH$(R^{5a})$—$OR^{5b}$, or —$(CH_2)_m$—CH$(R^5)$—$SR^5$;

each $R^{a2}$ independently is hydrogen, $C_{1-6}$ aliphatic, $C_{1-6}$ fluoroaliphatic, —$(CH_2)_m$—$CH_2$—$R^B$, —$(CH_2)_m$—$CH_2$—NHC(=$NR^4$)NH—Y, —$(CH_2)_m$—$CH_2$—CON$(R^4)_2$, —$(CH_2)_m$—$CH_2$—N$(R^4)$CON$(R^4)_2$, —$(CH_2)_m$—CH$(R^6)$N$(R^4)_2$, —$(CH_2)_m$—CH$(R^{5a})$—$OR^{5b}$, or —$(CH_2)_m$—CH$(R^5)$—$SR^5$;

each $R^B$ independently is a substituted or unsubstituted mono- or bicyclic ring system;

each $R^4$ independently is hydrogen or a substituted or unsubstituted aliphatic, aryl, heteroaryl, or heterocyclyl group; or two $R^4$ on the same nitrogen atom, taken together with the nitrogen atom, form a substituted or unsubstituted 4- to 8-membered heterocyclyl ring having, in addition to the nitrogen atom, 0-2 ring heteroatoms independently selected from N, O, and S;

each $R^5$ independently is hydrogen or a substituted or unsubstituted aliphatic, aryl, heteroaryl, or heterocyclyl group;

each $R^{5a}$ independently is hydrogen or a substituted or unsubstituted aliphatic, aryl, heteroaryl, or heterocyclyl group;

each $R^{5b}$ independently is hydrogen or a substituted or unsubstituted aliphatic, aryl, heteroaryl, or heterocyclyl group;

each $R^6$ independently is a substituted or unsubstituted aliphatic, aryl, or heteroaryl group;

Y is hydrogen, —CN, or —$NO_2$;

m is 0, 1, or 2;

each of $R^{b1}$ and $R^{b2}$ independently is hydrogen, —$CO_2H$, —OH, or a substituted or unsubstituted aliphatic, aryl, heteroaryl, or heterocyclyl group;

each of $R^{b3}$ and $R^{b4}$ independently is hydrogen, —$CO_2H$, or a substituted or unsubstituted aliphatic, aryl, heteroaryl, or heterocyclyl group;

or $R^{b2}$ and $R^{b4}$ are each independently hydrogen, and $R^{b1}$ and $R^{b3}$, taken together with the carbon atoms to which they are attached, form an unsubstituted or substituted fused 4- to 8-membered non-aromatic ring having 0-3 ring heteroatoms selected from the group consisting of O, N, and S, wherein said ring may be optionally fused to an unsubstituted or substituted 4- to 8-membered non-aromatic ring, or 5- to 6-membered aromatic ring having 0-3 ring heteroatoms selected from the group consisting of O, N, and S;

or $R^{b2}$ and $R^{b4}$ are absent, and $R^{b1}$ and $R^{b3}$, taken together with the carbon atoms to which they are attached, form an unsubstituted or substituted fused 5- to 6-membered aromatic ring having 0-3 ring heteroatoms selected from the group consisting of O, N, and S, wherein said ring may be optionally fused to an unsubstituted or substituted 4- to 8-membered non-aromatic ring, or 5- to 6-membered aromatic ring having 0-3 ring heteroatoms selected from the group consisting of O, N, and S; and n is 0 or 1;

the process comprising:

(1a) coupling a compound of Formula (vi) with a compound, P-LG, to form a compound of Formula (vii)

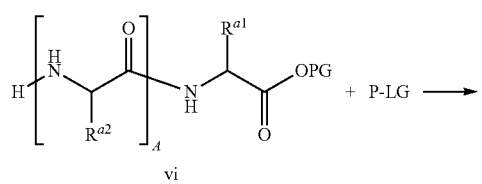

vi wherein PG is hydrogen or a protecting group; and LG is a leaving group;

(2a) deprotecting the compound of Formula (vii) to form a compound of Formula (viia)

(3a) coupling the compound of Formula (viia) with a compound of Formula (i) to form a compound of Formula (iv)

wherein $X^-$ is a counter anion;

(4) deprotecting the compound of Formula (iv) to form a compound of Formula (v)

and (5) reacting the compound of Formula (v) with an alpha hydroxy carboxylic acid or a beta hydroxy carboxylic acid to form a compound of Formula (II).

2. The process of claim 1, wherein the reaction of step (1a) or step (3a) or both is conducted in the presence of a peptide coupling reagent.

3. The process of claim 2, wherein the peptide coupling reagent is selected from the group consisting of a carbodiimide reagent, phosphonium reagent, and uronium reagent.

4. The process of claim 3, wherein the peptide coupling reagent is selected from one or more of the group consisting of dicyclohexylcarbodiimide (DCC), 1-(3-dimethylaminopropyl)-3-ethylcarbodiimide (EDC), benzotriazol-1-yloxy-tris(dimethylamino)phosphonium hexafluorophosphate (BOP), and O-(1H-benzotriazol-1-yl)-N,N,N',N'-tetramethyluronium tetrafluoroborate (TBTU).

5. The process of claim 1, further comprising converting the carboxylic acid moiety of compound (viia) to an activated ester or acid halide prior to the reaction of step (3a).

6. The process of claim 5, wherein said activated ester or acid halide is an O—(N-hydroxysuccinnimide) ester.

7. The process of claim 1, wherein the reaction of step (1a) is conducted in the presence of a solvent.

8. The process of claim 7, wherein the solvent is tetrahydrofuran.

9. The process of claim 1, wherein the reaction of step (4) is conducted in the presence of an aqueous mineral acid.

10. The process of claim 9, wherein the mineral acid is hydrochloric acid.

11. The process of claim 1, wherein the reaction of step (4) is conducted in the presence of an organic boronic acid acceptor.

12. The process of claim 11, wherein the organic boronic acid acceptor is i-BuB(OH)$_2$.

13. The process of claim 1, wherein the reaction of step (5) is conducted in the presence of a solvent selected from the group consisting of ethyl acetate, methyl isobutyl ketone, acetone, acetonitrile, 2-methyltetrahydrofuran, anisole, isopropyl acetate, dimethoxyethane, tetrahydrofuran, dioxane, dichloromethane, toluene, heptane, methyl-cyclohexane, tert-butylmethyl ether, and any combination thereof.

14. The process of claim 1, wherein the reaction of step (5) is conducted in the presence of a catalyst, wherein the catalyst is an organic amine base.

15. The process of claim 14, wherein the catalyst is selected from the group consisting of triethylamine, triethylenediamine, pyridine, collidine, 2,6-lutidine, 4-dimethylaminopyridine, di-tertbutylpyridine, N-methylmorpholine, N-methylpiperidine, tetramethylguanidine, diazabicyclo[5.4.0]undec-7-ene (DBU), 1,4-diazabicyclo[2.2.2]octane, 1,5-diazabicycle[4.3.0]non-5-ene, N,N'diisopropylethylamine, or any combination thereof.

16. The process of claim 1, wherein step (5) further comprises cooling the solution.

17. The process of claim 16, wherein the cooling comprises cooling the solution uncontrolled until the internal temperature is about 25° C.

18. The process of claim 16, wherein the cooling is conducted in the presence of a co-solvent.

19. The process of claim 18, wherein the co-solvent is selected from the group consisting of heptane, methylcyclohexane, toluene, tert-butylmethyl ether, ethyl acetate, or any combination thereof.

20. The process of claim 1, further comprising
(6) isolating the compound of Formula (II) as a crystalline solid.

21. The process of claim 1, wherein PG is a protecting group selected from the group consisting of an acyl protecting group and a urethane protecting group.

22. The process of claim 21, wherein PG is a protecting group selected from the group consisting of formyl, acetyl, succinyl, methoxysuccinyl, tert-butoxycarbonyl (Boc), benzyloxycarbonyl (Cbz), and fluorenylmethoxycarbonyl (Fmoc).

23. The process of claim 1, wherein LG is —Cl.

24. The process of claim 1, wherein X$^-$ is CF$_3$CO$_2^-$.

25. The process of claim 1, wherein R$^c$ is selected from the group consisting of 2,5-dichlorophenyl.

26. The process of claim 1, wherein
A is 0;
R$^a$ is C$_{1-6}$ aliphatic;
R$^{a1}$ is hydrogen, C$_{1-6}$ aliphatic, —(CH$_2$)$_m$—CH$_2$—R$^B$, or —(CH$_2$)$_m$—CH(R$^{5a}$)—OR$^{5b}$;
each of R$^{b1}$ and R$^{b2}$ independently is hydrogen, —CO$_2$H, —OH, or a substituted or unsubstituted aliphatic;
each of R$^{b3}$ and R$^{b4}$ independently is hydrogen, C$_{1-6}$ aliphatic, or —(CH$_2$)$_p$CO$_2$H; and
p is 0 or 1.

27. The process of claim 1, wherein
A is 0;
R$^D$ is 2,5-dichlorophenyl;
R$^a$ is isobutyl;
R$^{a1}$ is hydrogen;
each R$^{b1}$ and R$^{b2}$ independently is hydrogen;
each R$^{b3}$ and R$^{b4}$ independently is —(CH$_2$)$_p$—CO$_2$H; p is 0 or 1; and n is 0 or 1.

28. The process of claim 1, wherein the alpha hydroxy carboxylic acid or a beta hydroxy carboxylic acid is citric acid.

29. The process of claim 1, wherein the compound of Formula (II) is 4-(R,S)-(carboxymethyl)-2-((R)-1-(2-(2,5-dichlorobenzamido)acetamido)-3-methylbutyl)-6-oxo-1,3,2-dioxaborinane-4-carboxylic acid.

30. The process of claim 1, wherein the compound of Formula (II) is 2,2'-{2-[(1R)-1-({[(2,5-dichlorobenzoyl)amino]acetyl}amino)-3-methylbutyl]-5-oxo-1,3,2-dioxaborolane-4,4-diyl}diacetic acid.

31. A process for generating a compound, Form-1,

Form-1 the process comprising the steps of
(1) reacting a compound, int-1, with glycine to form a compound, int-2

(2) reacting the compound, int-2, with a compound, int-3, to form a compound, int-4

-continued

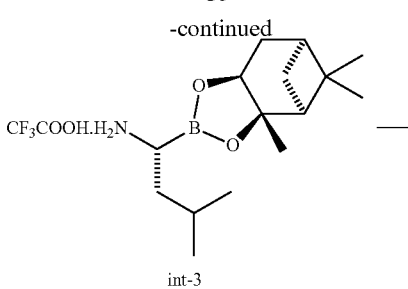
int-3

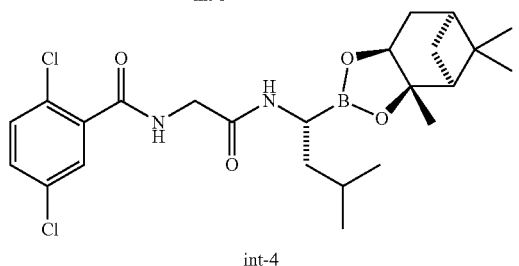
int-4

(3) reacting the compound, int-4, with HCl to form a compound, int-5

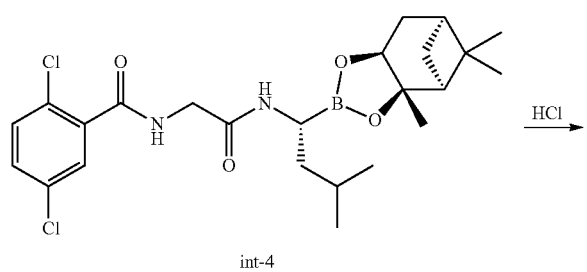
int-4

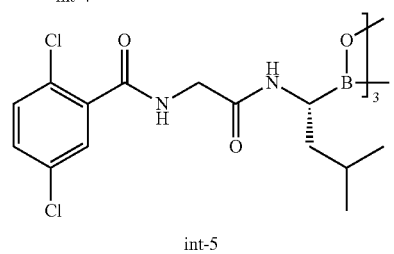
int-5

(4) reacting the compound, int-5, with citric acid to form the compound, Form-1

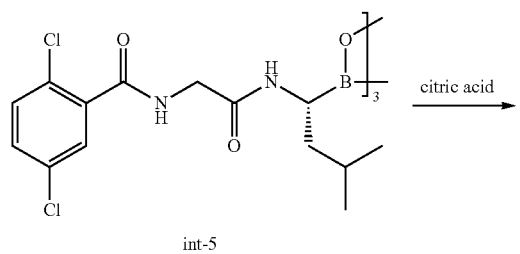
int-5

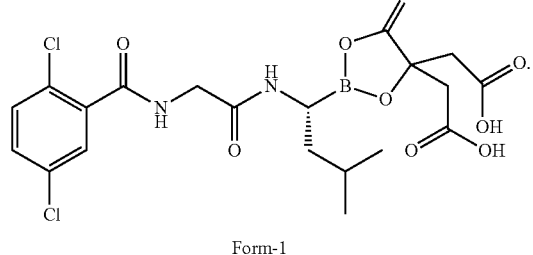
Form-1

32. The process of claim 31, wherein the reaction of step (1) is conducted in the presence of NaOH.

33. The process of claim 31, wherein the reaction of step (2) is conducted in the presence of TBTU.

34. The process of claim 31, wherein the reaction of step (2) is conducted in the presence of DIPEA.

35. The process of claim 31, wherein the reaction of step (3) is conducted in the presence of methanol and hexane.

36. The process of claim 31, wherein the reaction of step (4) is conducted in the presence of ethyl acetate.

37. The process of claim 31, wherein the reaction of step (4) comprises cooling the solution uncontrolled until the internal temperature is about 25° C.

38. A process for generating a compound, Form-1,

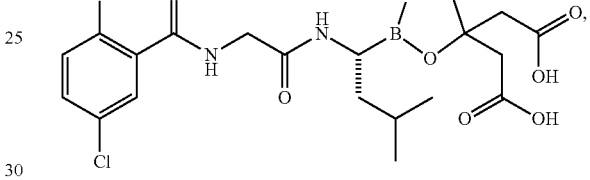
Form-1 the process comprising reacting a compound, int-5, with citric acid to form the compound, Form-1

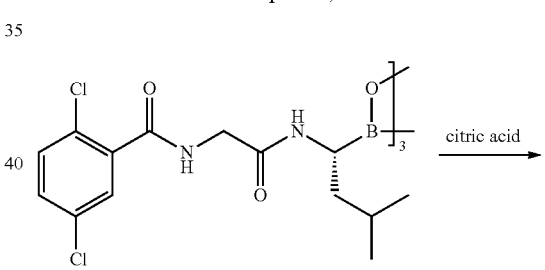
int-5

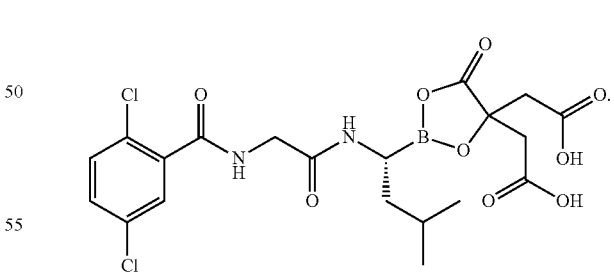
Form-1

39. The process of claim 38, wherein the reaction is conducted in the presence of ethyl acetate.

40. The process of claim 38, wherein the reaction further comprises cooling the solution uncontrolled until the internal temperature is about 25° C.

* * * * *